United States Patent
Yadav et al.

(10) Patent No.: US 7,238,854 B2
(45) Date of Patent: Jul. 3, 2007

(54) METHOD OF CONTROLLING SITE-SPECIFIC RECOMBINATION

(75) Inventors: Narendra S. Yadav, Chadds Ford, PA (US); Jianjun Yang, Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 507 days.

(21) Appl. No.: 10/353,454

(22) Filed: Jan. 29, 2003

(65) Prior Publication Data

US 2003/0194809 A1 Oct. 16, 2003

Related U.S. Application Data

(60) Provisional application No. 60/352,798, filed on Apr. 11, 2002.

(51) Int. Cl.
| | |
|---|---|
| C12N 15/82 | (2006.01) |
| C12N 15/31 | (2006.01) |
| C12N 15/52 | (2006.01) |
| C12N 15/62 | (2006.01) |
| A01H 1/00 | (2006.01) |

(52) U.S. Cl. ............ 800/278; 800/260; 800/287; 800/288; 800/306; 435/69.7; 435/462; 435/468; 536/23.2; 536/23.4; 536/23.7

(58) Field of Classification Search ............ 800/278, 800/287, 260, 288, 285, 317.4, 320.1; 435/462, 435/69.7; 536/23.4, 23.7

See application file for complete search history.

(56) References Cited

U.S. PATENT DOCUMENTS

| | | | | |
|---|---|---|---|---|
| 5,550,038 | A | * | 8/1996 | Goodman et al. ......... 435/70.1 |
| 6,077,992 | A | | 6/2000 | Yadav |
| 6,110,736 | A | | 8/2000 | Hodges et al. |
| 6,365,377 | B1 | * | 4/2002 | Patten et al. ............. 435/91.1 |
| 2002/0007500 | A1 | | 1/2002 | Kurshinov |

FOREIGN PATENT DOCUMENTS

| | | |
|---|---|---|
| WO | WO 9109957 A1 | 7/1991 |
| WO | WO 9301283 A1 | 1/1993 |
| WO | WO 9737012 A1 | 10/1997 |
| WO | WO 00/17365 A2 | 3/2000 |
| WO | WO 01/36595 A2 | 5/2001 |

OTHER PUBLICATIONS

Zhang et al. Theoretical and Applied Genetics 107(7): 1157-1168 (Nov. 2003).*
Cantor et al. Protein Expression and Purification 22(1): 135-140 (Jun. 2001).*
Stam et al. Annals of Botany 79: 3-12 (1997).*
Colliver et al. Plant Molecular Biology 35: 509-522 (1997).*
Dale et al. Proc. Natl. Acad. Sci. USA 88(23): 10558-10562 (Dec. 1991).*
Gleave et al. Plant Molecular Biology 40(2): 223-235 (May 1999).*
Perler. F. B., Cell, Protein Splicing of Inteins and Hedgehog Autoproteolysis: Structure, Function, and Envolution, vol. 92: pp. 1-4, 1998.
Perler. F. B., Nucl. Acids. Res. , InBase, The Intein Database, vol. 28: pp. 344-345 ,2000.
Noren. C. J. et al., Agnew. Chem. Int. Ed. Dissecting the Chemistry of Protein Splicing and Its Applications, vol. 39: pp. 450-466, 2000.
Perler, F. B. and Adam, E. Curr. Opin. Biol. Protein splicing and its applications. vol. 11: pp. 377-383, 2000.
Mills, K. V. Proc. Natl. Acad. Sci. , Protein splicing in trans by purified N- and C-terminal fragments of the *Mycobacterium tuberculosis* RecA intein, . vol. 95: pp. 3543-3548, 1998, No. 7.
Southworth. M. W. et al., EMBO., Control of protein splicing by intein fragment reassembly, vol. 17: pp. 918-926, 1998, No. 4.
Wu et al., Biochimica et Biophysica Acta, Protein trans-splicing and functional mini-inteins of a cyanobacterial dnaB intein, vol. 187: pp. 422-432, 1998.
Yamazaki, T. et al., Am. Chem. Soc., Segmental Isotope Labeling for Protein NMR Using Peptide Splicing, vol. 120: 5591-5592, 1998, No. 2, June.
Wu et al., Proc. Natl. Acad. Sci. , Protein trans-splicing by a split intein encoded in a split DnaE gene of Synechocystis sp. PCC6803, USA. 95: pp. 9226-9231, 1998, No. 16.
Martin, D. D. et al., Biochemistry, Characterization of a Naturally Occurring Trans-Splicing Intein from Synechocystis sp. PCC6803, vol. 40: pp. 1393-1402, 2001, No. 15.
Sun, L. et al., Appl. Envir. Micro. Protein trans-Splicing to Produce Herbicide-Resistant Acetolactate Synthase. vol. 67: pp. 1025-1029, 2001, (No. 3, March).
Chen et al., Gene, Herbicide resistance from a divided EPSPS protein: the split synechocystis DnaE Intein as an in vivo affinity domain, vol. 263: pp. 39-48, 2001, (No. 1-2, January).
Odell et al., Plant Physiol. , Seed-Specific Gene Activation Mediated by the Cre/lox Site Specific Recombination System, vol. 106: pp. 447-458, 1994.
Russel et al., Directed excision of a transgene from the plant genome, Mol. Gen. Genet. 234: pp. 49-59, 1992.
Schmidt et al., PNAS, Illegitimate Cre-dependent chromosome rearrangements in transgenic mouse spermatids, vol. 97: pp. 13702-13707, 2000, No. 25.
Evans et al., Protein trans-Splicing and Cyclization by a Naturally Split Intein from the dnaE Gene of Synechocystis Species PCC6803, The Journal of Biological Chemistry, vol. 275, No. 13, pp. 9091-9094, (2000).

* cited by examiner

*Primary Examiner*—David T. Fox

(57) ABSTRACT

The present invention provides methods for the conditional or regulated expression of a site-specific recombinase using split intein-mediated protein splicing. This enhances the temporal and tissue-specificity of trait gene expression and allows for fine tuning of expression specificity.

32 Claims, 4 Drawing Sheets

METHOD OF CONTROLLING SITE-SPECIFIC RECOMBINATION

This application claims the benefit of U.S. provisional application No. 60/352,798 filed 11 Apr. 2002.

FIELD OF INVENTION

The present invention relates to the field of molecular biology and the genetic transformation of organisms with foreign gene fragments. More particularly, the invention relates to methods of controlling site-specific recombination using intein-mediated protein splicing.

BACKGROUND OF THE INVENTION

Inteins (internal protein fragments) are in-frame intervening sequences that disrupt the coding region of a host gene. These internal protein elements mediate the post-translational protein splicing process, catalyzing a series of reactions to remove the intein from the protein precursor and to ligate the flanking external protein fragments, known as exteins, into a mature protein (Perler, F. B. *Cell* 92:1-4 (1998)). A typical intein element consists of 400 to 500 amino acid residues and contains four conserved protein splicing motifs, although mini-inteins approximately 150 amino acids in size have been identified (Perler, F. B. *Nucl. Acids. Res.* 28:344-345 (2000)). Over all, nearly 140 putative inteins have been found from prokaryotes (archaea and eubacteria) and single cell eukaryotes such as algae and yeast, mostly through genome sequencing projects (Perler, F. B. (2000), supra). The majority of these inteins mediate maturation of enzymes involved in replication, DNA repair, transcription, or translation. Protein splicing has yet to be observed in a multicellular organism.

Since the discovery of inteins, much has been done to elucidate their functional mechanisms and potential applications. The complete splicing mechanism, consisting of four coupled nucleophilic displacements between three conserved amino acid residues at intein-extein junctions, is reviewed by Noren, C. J. et al. (*Angew. Chem. Int. Ed.* 39:450-466 (2000)). This protein splicing mechanism has been reconstituted in vivo and in vitro, demonstrating that inteins could be used as powerful tools for protein modification and engineering (Perler, F. B. and Adam, E. *Curr. Opin. Biol.* 11:377-383 (2000)). Additionally, both trans-splicing and cis-splicing have been studied.

Protein trans-splicing is a reaction that ligates separate proteins into a hybrid molecule, mediated by a pair of split inteins. Therefore, protein trans-splicing offers great advantages over cis-splicing. For example, trans-splicing can permit the synthesis of highly toxic proteins, when a strategy is applied such that single cells only contain a portion of the toxic protein, while the entire toxic protein is synthesized in vitro. Additionally, it may permit expression of a gene from two different loci of a genome or two cellular compartments. To study protein trans-splicing, artificial split inteins have been generated, in which the N-terminal half intein (Int-n) usually contains the critical A and B splicing motifs and the C-terminal half intein (Int-c) contains the C and F motifs. When the half inteins are fused, each half intein being associated with a partial protein, the two partial proteins can be spliced to form a hybrid product both in vitro and in vivo (Mills, K. V. *Proc. Nat. Acad. Sci. USA.* 95: 3543-3548 (1998); Southworth, M. W. et al. *EMBO.* 17:918-926 (1998); Wu, H. et al. *Biochimica et Biophysica Acta* 187:422-432 (1998); Yamazaki, T. et al. *J. Am. Chem. Soc.* 120:5591-5592 (1998)). The general utility of these artificial inteins, however, is hindered by a strict requirement for urea treatment to denature and renature the proteins.

The Ssp DnaE inteins are the only known natural split inteins. This intein class was identified from the split DnaE genes of *Synechocystis* sp. PCC6803, which encode the catalytic subunit α of DNA polymerase III (Wu, H. et al. *Proc. Natl. Acad. Sci. USA.* 95:9226-9231 (1998)). The N-terminal half of the DnaE protein containing 774 amino acid residues is fused to the N-terminal 123 amino acid Ssp DnaE intein sequence. The remaining 36 amino acid residues of the C-terminal half of the Ssp DnaE intein are fused separately to the C-terminal half of the DnaE protein, containing 423 amino acids. These two genes are located 745 kB apart on opposite strands of the Ssp PCC6803 genome, although their protein product is an intact catalytic subunit of 1197 amino acid residues lacking any intein sequence due to the intein-mediated protein trans-splicing. In general, efficiency of the protein trans-splicing is usually higher when using Ssp DnaE natural split inteins instead of artificial split inteins (Martin, D. D. et al. *Biochemistry.* 40:1393-1402 (2001)).

The split Ssp DnaE inteins are also unique in their ability to catalyze the trans-splicing reaction even when two halves of the exteins are foreign proteins. For example, using two compatible plasmids each with an unlinked gene fragment, *E. coli* was found to be able to: (1) express the two gene fragments containing halves of a herbicide-resistant form of bacterial acetolactate synthase II (ALAS II) gene each fused to the split intein sequences; and (2) form a herbicide-insensitive enzyme in vivo (Sun, L. et al. *Appl. Envir. Micro.* 67:1025-1029 (2001)). When a wild type corn ALS gene was similarly used, the expected size of the reconstituted enzyme was formed in vivo (in *E. coli*) but no evidence was presented as to whether it was functional or whether intein-mediated splicing can occur in plant cells. A similar study was performed, again in *E. coli*, whereby it was determined that an artificially split bacterial 5-enolpyruvylshikimate-3-phosphate synthase (EPSPS) gene could be reassembled as a functional enzyme via intein trans-splicing (Chen et al. *Gene* 263:39-48 (2001)).

In both Sun et al., supra, and Chen et al., supra, it is suggested that the split Ssp DnaE inteins may be used in agriculture where plants may be genetically modified by utilizing trans-splicing technology to contain herbicide resistant transgenes in crops. In theory, this could be accomplished by expressing inactive gene fragments in separate DNA locations, and only allowing protein activity to be generated following trans-splicing. However, the art is silent concerning the methodology that would be necessary for one skilled in the art of plant transgene expression to practice this concept, and no demonstration of the intein-mediated protein splicing technique exists in eukaryotes. Further, there has been no demonstration that inteins are able to function in higher organisms, such as plants.

The advent of genetically modified crops holds the promise of improving crop yield and quality. These benefits are conferred via the transformation of crop plants with new transgenes encoding desirable traits. Plants are increasingly being looked to as platforms for the production of materials, foreign to plant systems. As the art of genetic engineering advances, it will be possible to engineer plants for the production of a multiplicity of monomers and polymers, currently only available by chemical synthetic means. The accumulation of these materials in various plant tissues will be toxic at some level and it will be useful to tightly regulate the relevant genes to prevent expression in inappropriate plant tissues.

Currently, few methods exist that provide for tightly regulated transgene expression. Non-specific expression of transgenes in non-target cells, tissues, or generations hinders plant transgenic work. This is important where the goal is to produce such high levels of materials in transgenic plants that may be phytotoxic or adversely affect normal plant development. Conditional transgene expression would enable economic production of desired chemicals, monomers, and polymers at levels likely to be phytotoxic to growing plants by restricting their production to transgenic crop biomass (production tissue) either just prior to or after its harvest for extracting the desired product. Therefore, the development of transgene expression in plants is limited both by the lack of a commercially usable conditional expression system and the difficulty in attaining reliable, high-level expression.

Transgenic trait expression often requires temporal and tissue-specific control of a transgene. Thus, binary expression systems are utilized such that traits are not expressed in the hybrid parents but are expressed in F1 hybrid progeny of parents each carrying an element of the binary system. A good example of this binary system is site-specific recombination (SSR), where one parent carries a site-specific recombinase and the other carries the inactive trait. The expression of this trait gene (TG) is blocked by the presence of a 'blocking' or 'STOP' fragment, flanked by the cognate SSR sites, which blocks transcription and/or translation of the TG (Yadav et al., WO 01/36595 A2; WO 00/17365 A2; U.S. Pat. No. 6,077,992).

Recombinase expression in the progeny leads to SSR and removal of the 'blocking' DNA fragment, thereby permitting transgene activation. Similarly, when generational control of removal of a TG flanked by SSR sites is required, one can cross one line carrying the TG and another expressing the recombinase gene.

Site-specific recombination [Odell et al., *Plant Physiol.* 106:447-458 (1994); Odell et al., PCT Int. Appl. WO 9109957 (1991); Surin et al., PCT Int. Appl WO 9737012 (1997); Ow et al., PCT Int. Appl. WO 9301283 A1 (1992); Russel et al., *Mol. Gen. Genet.* 234:49-59 (1992); and Hodges et al. (U.S. Pat. No. 6,110,736)] in plants has been demonstrated. Furthermore, regulated SSR in plants and the use of mutant sites to enhance the specificity of Cre-mediated recombination in conjunction with chimeric Cre genes under the control of available regulated promoters has also been demonstrated in plants (Yadav et al., WO 01/36595 A2; WO 00/17365 A2; EP1115870 A2). Further, directed excision of a transgene from the plant genome has been reported using recombinase specific-sites and a recombinase (Russel et al., *Mol. Gen. Genet.* 234:49-59 (1992); Ow et al., PCT Int. Appl. WO 9301283 A1 (1992)).

One limitation of the above-mentioned approach, however, is that only one parent can carry the recombinase and the other its substrate containing the cognate SSR sites. As a result, the trait locus is heterologous in F1 hybrid progeny. Another limitation of the existing SSR techniques is that the site-specific recombinase may show toxicity through chromosomal rearrangements in plants and animals. For example, the Cre transgene under some plant promoters (e.g., the Bcp 1 gene) show Cre phytotoxicity in some transformants, even when they have the required regulation specificity. This results in pollen sterility with Bcp1:Cre and unwanted spread of active Cre recombinase in future generations. Such toxicity has also been reported in animal cells (see Schmidt et. al. *PNAS, U.S.A.* 97:13702-13707 (2000)). One solution to such toxicity, when the threshold of recombinase concentration for toxicity is higher than for recombination, is to contain the recombinase within the floxed DNA element such that upon SSR the recombinase gene is autoexcised; and thus, build up of recombinase is prevented. However, maintainence of these lines will be unlikely when the recombinase is under the control of a developmentally regulated promoter.

The problem to be solved therefore is to develop a system for conditionally regulating transgene expression through the implementation of site-specific recombinase systems such that the potential toxicity of the recombinase is minimized.

Applicant has solved the stated problem in the present invention through the development of a site-specific recombinase system based on intein-mediated protein splicing, comprising an inactive recombinase element and a trait expression construct containing an expressible transgene. The organization of the inactive recombinase element results in the splitting the site-specific recombinase into two inactive components that are unable to catalyze the SSR when present individually. However, when both inactive split recombinases are brought together, say, by a cross, the recombinase activity is restored through a split intein-mediated trans-protein splicing reaction. Once restored, the recombinase may act on the trait expression construct to regulate transgene expression.

SUMMARY OF THE INVENTION

The present invention provides methods for the conditional or regulated expression of a site-specific recombinase that enhances temporal and tissue-specific trait or phenotype expression. This allows F1 progeny to be homozygous for the trait locus. In addition, it prevents Cre potential toxicity, when the threshold of Cre concentration for SSR is lower than that for its potential toxicity. It also provides for improved specificity for recombination. Accordingly the invention provides an inactive recombinase element selected from the group consisting of:

a) a DNA construct having the general structure in a 5' to 3' orientation comprising: P1-ssrN-IntN, wherein;
   (i) P1 is a promoter;
   (ii) ssrN is the N-terminal portion of a site-specific recombinase; and
   (iii) IntN is the N-terminal portion of a split intein;

wherein each of P1, ssrN, and IntN are operably linked such that activation of the promoter results in the expression of the ssrN-IntN fusion protein lacking recombinase activity; and b) a DNA construct having the general structure in a 5' to 3' orientation comprising: P2-IntC-ssrC, wherein;
   (i) P2 is a promoter;
   (ii) ssrC is the C-terminal portion of a site-specific recombinase; and
   (iii) IntC is the C-terminal portion of a split intein;

wherein each of P2, ssrC, and IntC are operably linked such that activation of the promoter results in the expression of the IntC-ssrC fusion protein lacking recombinase activity, and wherein the inactive recombinase elements of (a) and (b) when present together in a cell will form an active recombinase protein by intein-mediated trans-protein splicing. In a preferred embodiment at least a portion of the IntN or IntC polypeptide has been modified to contain plant preferred codons.

Promoters of the invention may be selected from any source, including: constitutive promoters, tissue-specific promoters, developmental stage-specific promoters, inducible promoters, viral promoters, male germline promoters, female germline promoters, common germline promoters, chemically inducible promoters, plant floral common germline promoters, plant vegetative shoot apical meristem promoters, and plant floral shoot apical meristem promoters.

Additionally the invention provides an intein-mediated site-specific recombination system comprising:
 a) an inactive recombinase element selected from the group consisting of:
  1) a DNA construct having the general structure in a 5' to 3' orientation comprising: P1-ssrN-IntN, wherein:
   (i) P1 is a promoter;
   (ii) ssrN is the N-terminal portion of a site-specific recombinase; and
   (iii) IntN is the N-terminal portion of a split intein;
  wherein each of P1, ssrN, and IntN are operably linked such that activation of the promoter results in the expression of the ssrN-IntN fusion protein lacking recombinase activity; and
  2) a DNA construct having the general structure in a 5' to 3' orientation comprising: P2-IntC-ssrC, wherein:
   (i) P2 is a promoter;
   (ii) ssrC is the C-terminal portion of a site-specific recombinase; and
   (iii) IntC is the C-terminal portion of a split intein;
 wherein each of P2, ssrC, and IntC are operably linked such that activation of the promoter results in the expression of the IntC-ssrC fusion protein lacking recombinase activity, and wherein the inactive recombinase elements of (a) and (b), when present together in a cell, will form an active recombinase protein by intein-mediated trans-protein splicing; and
 b) a site-specific recombinase DNA substrate, wherein said substrate undergoes site-specific recombination in the presence of the active recombinase.

In a preferred embodiment the site-specific recombinase DNA substrate will have the general structure in a 5' to 3' orientation: P3-RS-X-RS-TG, wherein:
 (i) P3 is a trait gene promoter;
 (ii) TG is a trait gene;
 (iii) RS are directly repeated recombinase sites responsive to the recombinase;
 (iv) X is a DNA fragment containing a stop fragment and optionally either:
  A) a DNA fragment encoding the N-terminal portion of a split intein; or
  B) a DNA fragment encoding the C-terminal portion of a split intein; and
  C) a transgene promoter capable of driving the transgene.

In one preferred embodiment the trait expression construct may additionally comprise an inactive recombinase element flanked by directly repeated recombinase sites responsive to the recombinase. In another preferred embodiment the trait expression construct may contain a DNA fragment containing a trait gene and (optionally either or both of a stop fragment and a promoter capable of driving a gene outside the repeated recombinase sites, which are responsive to the recombinase).

In all aspects of the invention the inactive recombinase elements and the trait expression construct may be genetically linked or unlinked.

The invention additionally provides a method for regulating the expression of a trait gene in a cell or organism comprising:
 a) providing a cell or organism comprising an intein-mediated protein splicing site-specific recombination system of the present invention; and
 b) growing the cell or organism under conditions whereby site-specific recombination in the presence of the active recombinase results in activation or removal of the trait gene(s).

In a specific embodiment the invention provides a method for conditionally activating a trait gene in a hybrid plant comprising:
 a) providing an intein-mediated site-specific recombination system comprising:
  1) an inactive recombinase element having the general structure P1-ssrN-IntN, wherein:
   (i) P1 is a promoter;
   (ii) ssrN is the N-terminal portion of a site-specific recombinase; and
   (iii) IntN is the N-terminal portion of a split intein;
  2) an inactive recombinase element having the general structure P2-IntC-ssrC, wherein:
   (i) P2 is a promoter that may be the same or different than P1;
   (ii) ssrC is the C-terminal portion of a site-specific recombinase; and
   (iii) IntC is the C-terminal portion of a split intein;
  3) a trait expression construct having the general structure in a 5' to 3' orientation: P3-RS-STP-RS-TG, wherein:
   (i) P3 is a promoter;
   (ii) TG is a trait gene;
   (iii) RS is a recombinase site responsive to the recombinase; and
   (iv) STP is a stop fragment;
 b) providing a first transgenic plant comprising the inactive recombinase element of (a)(1) and the trait expression construct of (a)(3);
 c) providing a second transgenic plant comprising the inactive recombinase element of (a)(2) and the trait expression construct of (a)(3);
 d) crossing the first and second plants such that:
  (i) co-expression of ssrN-intN and IntC-ssrC fusion proteins in the first generation results in intein-mediated protein splicing to generate a functional active recombinase; and
  (ii) excision of the stop fragment by the action of the active recombinase on the recombinase sites operably links P3 and the trait gene resulting in the expression of the trait gene, in the first or second generation plant.

In an alternate embodiment the invention provides a method for conditionally removing a trait gene in a hybrid plant comprising:
 a) providing an intein-mediated site-specific recombination system comprising:
  1) an inactive recombinase element having the general structure P1-ssrN-IntN, wherein:
   (i) P1 is a promoter;
   (ii) ssrN is the N-terminal portion of a site-specific recombinase; and
   (iii) IntN is the N-terminal portion of a split intein;
  2) an inactive recombinase element having the general structure P1-IntC-ssrC, wherein:
   (i) P2 is a promoter that may be the same or different than P1;

(ii) ssrC is the C-terminal portion of a site-specific recombinase; and (iii) IntC is the C-terminal portion of a split intein; and 3) a trait expression construct having a floxed trait gene: RS-TG-RS, wherein:

(i) TG is a trait gene; and (ii) RS are directly repeated recombinase sites responsive to the recombinase;

b) providing a first transgenic plant comprising the inactive recombinase element of (a)(1) and the trait expression construct of (a)(3);

c) providing a second transgenic plant comprising the inactive recombinase element of (a)(2) and the trait expression construct of (a)(3);

d) crossing the first and second plants such that:

(i) co-expression of ssrN-intN and IntC-ssrC fusion proteins in the first generation results in intein-mediated protein splicing to generate a functional active recombinase; and (ii) excision of the trait gene by the action of the active recombinase.

BRIEF DESCRIPTION OF FIGURES AND SEQUENCE DESCRIPTIONS

Figure 1:
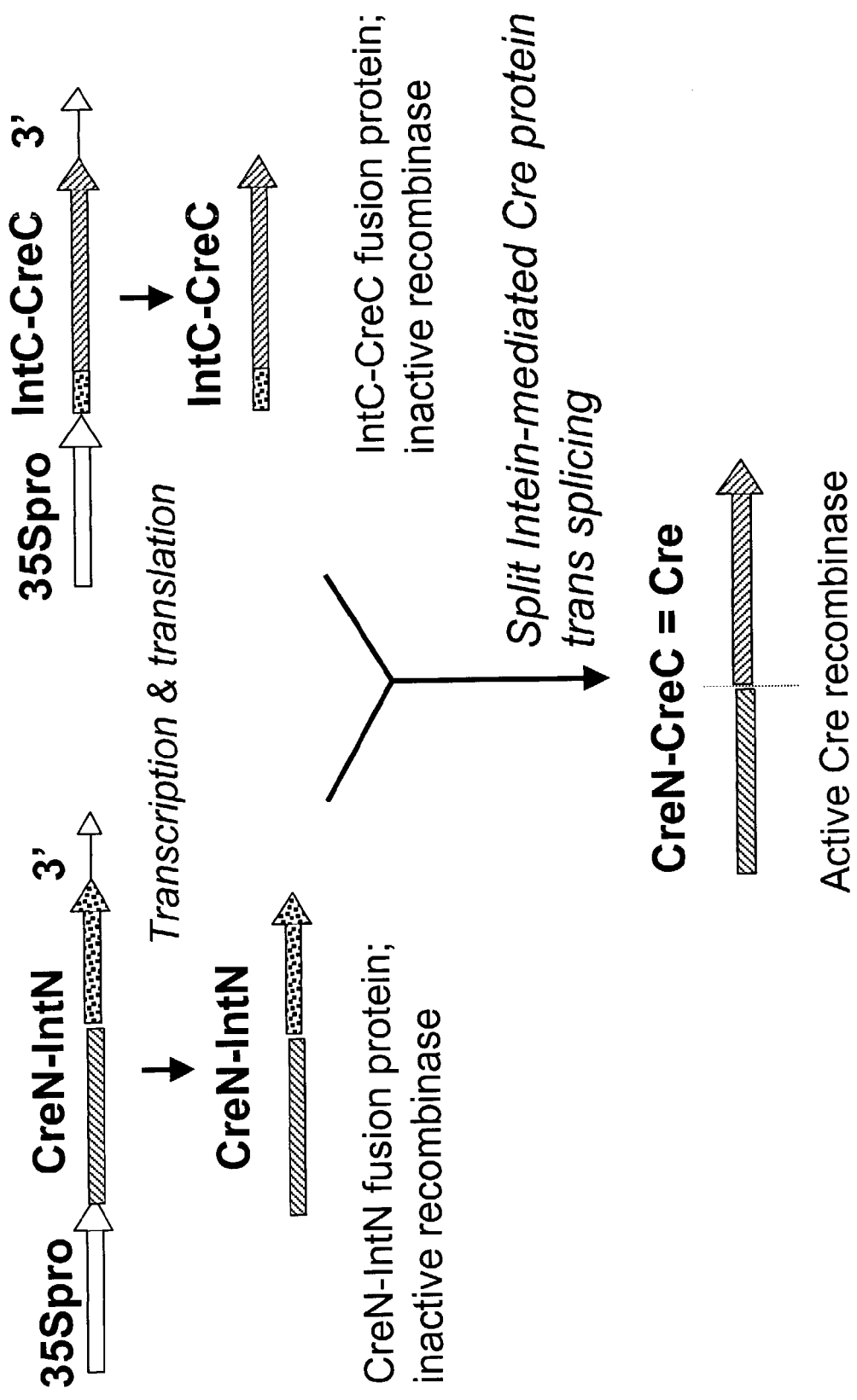
FIG. 1 shows the intein-mediated trans-protein splicing reaction of a split Cre recombinase, which produces an active Cre protein.

The following sequence descriptions and sequences listings attached hereto comply with the rules governing nucleotide and/or amino acid sequence disclosures in patent applications as set forth in 37 C.F.R. §1.821-1.825. The Sequence Descriptions contain the one letter code for nucleotide sequence characters and the three letter codes for amino acids as defined in conformity with the IUPAC-IYUB standards described in *Nucleic Acids Research* 13:3021-3030 (1985) and in the *Biochemical Journal* 219 (No. 2):345-373 (1984) which are herein incorporated by reference. The symbols and format used for nucleotide and amino acid sequence data comply with the rules set forth in 37 C.F.R. §1.822.

SEQ ID NOs:1 and 2 are the native amino acid sequence of the split intein DnaE from *Synechocystis* sp. PCC6803.

SEQ ID NOs:3-21 represent overlapping oligomers, containing plant preferred codons, used for synthesis of the split intein DnaE from *Synechocystis* sp. PCC6803.

SEQ ID NO:22 is the nucleotide sequence for the split intein Ssp DnaE Int-n, containing plant preferred codons. The sequence is referred to as the Plnt-n coding region.

SEQ ID NO:23 is the amino acid sequence encoding Plnt-n.

SEQ ID NO:24 is the nucleotide sequence for the split intein Ssp DnaE Int-c, containing plant preferred codons. The sequence is referred to as the Plnt-c coding region.

SEQ ID NO:25 is the amino acid sequence encoding Plnt-c.

SEQ ID NOs:26, 32, 33, 39, 41, 43, 44, 46 are various linker sequences used in vector design.

SEQ ID NOs:27-30 are the primers used as PH820, PH821, PH824, and PH825, respectively.

SEQ ID NO:31 is a 3034 bp Asp718 fragment containing a 35S-CreN-IntN ocs gene in plasmid pGV947.

SEQ ID NOs:34-37 are the primers used as PH826, PH827, PH822, and PH823, respectively.

SEQ ID NO:38 is the 2873 bp Asp718 bp fragment containing 35S:IntC-CreC:3'ocs in plasmid pGV951.

SEQ ID NO:40 is the 5449 bp Sal I-Hind III fragment containing the blocked GUS reporter gene for Cre-Lox excision in plasmid pGV801.

SEQ ID NO:42 is the Lox P sequence.

SEQ ID NO:45 is a 2189 bp Bgl II-Hind III fragment containing the SCP:Flp:3'pin gene in plasmid pPH12891.

SEQ ID NO:47 is a 76 bp sequence containing a 5'UTR.

SEQ ID NOs:48-51 are the primers used as FlpN-UP, FlpN-LP, IntN-UP, and IntN-LP, respectively.

SEQ ID NO:52 is a 1933 bp Bgl II-Eco RI fragment containing the SCP:FlpN-IntN:3'pin gene in plasmid pSCP:FlpN-IntN:3'pin.

SEQ ID NOs:53-56 are the primers used as IntC-UP, IntC-LP, FlpC-UP and FlpC-LP, respectively.

SEQ ID NO:57 is a 3002 bp Asp718 fragment containing 35S:IntC-FlpC:3'ocs gene in plasmid p35S:IntC-FlpCP:3'ocs.

SEQ ID NO:58 is a 12-amino acid N-terminal amino acid extension to the GUS ORF.

SEQ ID NO:59 is a 13 N-terminal amino acid extension to the GUS ORF.

DETAILED DESCRIPTION OF THE INVENTION

The present invention provides constructs and methods for the conditional or regulated expression of a site-specific recombinase system using intein-mediated trans-protein splicing. A variety of constitutive, inducible, tissue-specific and/or development-specific promoters are utilized to control expression of intein-site-specific recombinase fusion proteins. This permits regulated expression of site-specific recombinase systems for enhanced temporal and tissue-specific trait or phenotype expression. Advantages of these methods permit both parents and F1 to be homozygous for a trait locus, Cre potential toxicity can be prevented when the threshold of Cre concentration for SSR is lower than that for its potential toxicity, and containment of an active recombinase and improved regulation specificity for recombination are achieved. These characteristics are especially important for plant breeding and agronomic applications, where SSR is used for controlling trait activation or trans-gene/marker removal from germline (pollen and/or seed) to obtain trait or marker transgene-free transgenic plants, respectively.

Abbreviations and Definitions

The following abbreviations will be used herein:

"PCR" is the abbreviation for Polymerase-Chain Reaction.

"SSR" is the abbreviation for site-specific recombination.

"rol C" is the abbreviation for the root locus C gene that causes root formation (see Constantino et al. *Genetics* 94:203 (1994)).

"IPT" is the abbreviation for the isopentyl transferase gene (Ebumina et al. *Proc. Natl. Acad. Sci. USA* 94:2117-2121 (1997)).

"KNAT" is the abbreviation for the Knox class of genes (see Reiser et al. *Plant Mol. Biol.* 42:151-166 (2000)).

"Lecl" is the abbreviation for *Arabidopsis* Leafy Cotyledon 1 (Lotan et al., *Cell* 93: 1195-1205 (1998)) gene.

"OSHI" is the abbreviation for a rice homeobox gene (Sentoku et al. *Developmental Biology* 220:358-364 (2000)).

"Kn1" is the abbreviation for corn Knotted 1 gene (Vollbrecht, E. et al. *Nature* 350:241-243 (1991)).

"Gmf" is the abbreviation for gametophytic male fertile.

"Gms" is the abbreviation for gametophytic male sterile.

"TG" is the abbreviation for trait gene.

"SAM" is the abbreviation for shoot apical meristem. SAM can be vegetative or floral.

"SAP" is the abbreviation for Synthetic anther promoter, as described in U.S. Pat. Nos. 5,470,359 and 5,837,850.

The following terms and definitions shall be used to fully understand the specification and claims.

The terms "split intein-mediated protein splicing" or "trans-protein splicing" refer to the process whereby a pair of split inteins catalyze their removal from protein precursors, resulting in the synthesis of a mature, active protein from two separate protein precursors.

A "split intein" is comprised of two distinct polypeptide proteins, referred to as the "N-terminal" or "N-intein" (abbreviated as IntN or Int-n) and the "C-terminal" or "C-intein" (abbreviated as IntC or Int-c) because of their homology to the N-terminal and C-terminal regions of non-split inteins, respectively. Together IntN and IntC polypeptides, when fused to foreign polypeptides, possess all necessary functionality to complete a trans-protein splicing reaction, whereby the two foreign "extein" fragments are ligated together by formation of a peptide bond.

The terms "ExtN" and "ExtC" refer to polypeptides derived from the N-terminal and C-terminal regions of a protein. ExtN and ExtC are inactive unless they undergo split-intein-mediated trans-protein splicing to reconstitute a functional protein. In the present application, ExtN and ExtC are derived from splitting a site-specific recombinase (SSR) enzyme into two portions. The particular location of the split within the recombinase can be at any site that allows the trans-protein splicing reaction to occur. These extein fragments so produced from the SSR enzyme will hereinafter be referred to as "ssrN" and "ssrC", respectively.

"ExtN-IntN" and "IntC-ExtC" refer to precursor fusion polypeptides in which the ExtN protein is fused at its C-terminus to the N-terminus of IntN protein and the IntC protein is fused at its C-terminus to the N-terminus of ExtC protein, respectively. When the fusion proteins are present together, they undergo trans-protein splicing such that the ExtN and ExtC polypeptides are ligated together by a peptide bond to form a mature, active ExtN-ExtC protein. In the present invention, ExtN and ExtC are the N-terminal and C-terminal regions, respectively, of a site-specific recombinase (i.e., ssrN and ssrC). Therefore, ExtN-IntN is encoded by an ORF made by an in-frame fusion of ssrN and IntN ORFs. Similarly, IntC-ExtC is encoded by an ORF made by an in-frame fusion of IntC and ssrC ORFs.

The term "recombinase" or "site-specific recombinase" refers to an enzyme(s) that carry out SSR that alters the DNA structure and includes transposases and lambda integration/excision enzymes, as well as site-specific recombinases. Well-known examples of recombinases can be found in Cre-lox, FLP/FRT, R/RS, Gin/gix, a pSR1 system, a cer system, and a fim system (for example, N. L. Craig, *Annu Rev. Genet.*, 22:17 (1988); Odell et al., *Use of site-specific recombination systems in plants. Homologous Recomb. Gene Silencing Plants* (1994), pp 219-70. Paszkowski, J., Ed. Kluwer: Dordrecht, Germany). Additionally, SSR systems have been identified in microorganisms such as phage, bacterium (e.g., *E. coli*), yeast and the like. This includes the *E. coli* lambda att P system (Zubko et al. *Nature Biotechnology* 18:442 (2000)) for integration and excision and the *Streptomyces* phage C31 integrase (Groth et al. *Proc. Natl Acad. Sci. USA* 97:5995 (2000)). When the SSR system separated from these microorganisms with the use of a Cre/lox system derived from P1 phage (WO 93/01283) is introduced into organisms (including plants) different from the organism from which this system had been derived, it behaves in the same way as in the original organism. The SSR system of yeast (*Zygosaccharomyces rouxii*) [pSR1 system (H. Matsuzaki et al., *J. Bacteriology*, 172:610 (1990))] can also be used in accordance with the present invention. This pSR1 system also maintains its inherent function in higher plants (H. Onouchi et al., *Nucleic Acid Res.*, 19:6373 (1991)).

"Recombinase site" or "site-specific recombination sequence" means a DNA sequence that a recombinase will recognize and bind to. It will be appreciated that this may be a wild type or mutant recombinase site, as long as functionality is maintained and the recombinase enzyme may still recognize the site, bind to the DNA sequence, and catalyze the recombination between two adjacent recombinase sites.

The term "floxed" will refer to the flanking of a genetic element with tandemly (i.e., directly repeated) site-specific sequences. The floxed element may be a trait expression construct or any other genetic element.

An "intein-mediated site-specific recombination system" means a system comprising two classes of genetic constructs, an inactive recombinase element containing a split intein-recombinase fusion and a trait expression construct that is a site-specific recombination (SSR) substrate comprising a trait gene to be expressed.

"Site-specific recombination substrate" or "SSR substrate" refers to any DNA that is a substrate of site-specific recombination resulting from the action of the site-specific recombinase on recombinase sites. It includes DNA elements flanked by recombinase sites that are either directly (in the case of floxed DNA elements) or indirectly repeated with respect to each other, such that the DNA element is removed or inverted, respectively, upon site-specific recombination.

The term "trait gene" means a gene introduced or re-introduced into an organism, the expression of which alters the phenotype of that organism.

"Trait expression construct" is defined herein as a genetic construct comprising a trait transgene to be expressed downstream of a trait gene promoter, where at least one site-specific recombinase site is placed between the trait gene promoter and the trait gene. The trait expression construct is a substrate for site-specific recombination that regulates the transgene's expression or removal. The site-specific recombination may involve directly repeated or inverted site-specific sequences. For example, in the case of transgene removal, the TG is flanked by directly repeated site-specific recombination sites. In the case of TG activation, removal of a blocking fragment flanked by directly repeated recombinase sites via SSR results in transcriptional and/or translation expression of the TG.

An "inactive recombinase element" refers to a DNA fragment encoding the ExtN-IntN or IntC-ExtC fusion protein. This encompasses constructs which have the structure: P-ssrN-IntN and P-IntC-ssrC-3', wherein: P is a promoter suitable for driving the expression of the fusion proteins ssrN-IntN or IntC-ssrC; and 3' is a 3' UTR regulatory sequence.

P-ssrN-IntN and P-ssrN-IntN-3' both refer to a P-ssrN-IntN-3' UTR gene in which the promoter, fusion protein, and the 3' UTR regions are operably linked. P-IntC-ssrC and P-IntC-ssrC-3' both refer to a P-IntC-ssrC-3' UTR gene in which the promoter, fusion protein, and the 3' UTR regions are operably linked.

An "N-inactive recombinase element" hereinafter refers to an inactive recombinase element that encodes the ssrN-IntN fusion protein.

A "C-inactive recombinase element" hereinafter refers to an inactive recombinase element that encodes the IntC-ssrC fusion protein.

An "N-recombinase protein fusion" refers to a protein precursor that is produced from an N-inactive recombinase element, while a "C-recombinase protein fusion" refers to a protein precursor that is produced from a C-inactive recombinase element.

An "N-plant host" refers to a plant that has been transformed with an N-inactive recombinase element. In like manner, a "C-plant host" refers to a plant that has been transformed with a C-inactive recombinase element.

"Trait locus" or "locus" means a gene whose expression results in a trait or phenotype either through the expression of a polypeptide or of a RNA construct that leads to transcriptional or post-transcriptional gene silencing. It includes transgenes that may be blocked or unblocked with respect to trait expression via site-specific recombination.

"Gene" refers to a nucleic acid fragment that expresses mRNA, functional RNA, or specific protein, including regulatory sequences. The term "native gene" refers to a gene as found in nature. The term "chimeric gene" refers to any gene that contains: 1) DNA sequences, including regulatory and coding sequences, that are not found together in nature; or 2) sequences encoding parts of proteins not naturally adjoined; or 3) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature. A "transgene" refers to a gene that has been introduced into the genome by transformation and is stably maintained. Transgenes may include, for example, genes that are either heterologous or homologous to the genes of a particular plant to be transformed. Additionally, transgenes may comprise native genes inserted into a non-native organism, or chimeric genes. The term "endogenous gene" refers to a native gene in its natural location in the genome of an organism.

"Coding sequence" refers to a DNA or RNA sequence that codes for a specific amino acid sequence and excludes the non-coding sequences. The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences, as well as sequences which may be a combination of synthetic and natural sequences. As is noted above, the term "suitable regulatory sequences" is not limited to promoters; however, some suitable regulatory sequences useful in the present invention will include, but are not limited to: constitutive plant promoters, plant tissue-specific promoters, plant developmental stage-specific promoters, inducible plant promoters and viral promoters.

The "3' region" or "3' UTR" means the 3' non-coding regulatory sequences located downstream of a coding sequence. This DNA can influence the transcription, RNA processing or stability, or translation of the associated coding sequence (e.g. for a recombinase, a transgene, etc.).

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that are capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue-specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions.

"Conditionally activating" refers to activating a recombinase that is normally not expressed. In the context of this invention, it refers to expression of recombinase either by a genetic cross and/or by an inducer, if it is inducible.

"Constitutive expression" refers to expression using a constitutive or regulated promoter. "Conditional" and "regulated expression" refer to expression controlled by a regulated promoter. "Transient" expression in the context of this invention refers to expression only in specific developmental stages or tissue in one or two generations.

"Constitutive promoter" refers to promoters that direct gene expression in all tissues and at all times. "Regulated promoter" refers to promoters that direct gene expression not constitutively but in a temporally- and/or spatially-regulated manner and include tissue-specific, developmental stage-specific, and inducible promoters. It includes natural and synthetic sequences as well as sequences which may be a combination of synthetic and natural sequences. Different promoters may direct the expression of a gene in different tissues or cell types, or at different stages of development, or in response to different environmental conditions. New promoters of various types useful in plant cells are constantly being discovered; numerous examples may be found in the compilation by Okamuro et al. (*Biochemistry of Plants* 15:1-82 (1989)). Since in most cases the exact boundaries of regulatory sequences have not been completely defined, DNA fragments of different lengths may have identical promoter activity. Typical regulated promoters useful in plants include, but are not limited to: safener-inducible promoters, promoters derived from the tetracycline-inducible system, promoters derived from salicylate-inducible systems, promoters derived from alcohol-inducible systems, promoters derived from glucocorticoid-inducible systems, promoters derived from pathogen-inducible systems, and promoters derived from ecdysome-inducible systems.

"Tissue-specific promoter" refers to regulated promoters that are not expressed in all plant cells, but only in one or more cell types in specific organs (e.g., leaves, shoot apical meristem, flower, or seeds), specific tissues (e.g., embryo or cotyledon), or specific cell types (e.g., leaf parenchyma, pollen, egg cell, microspore- or megaspore mother cells, or seed storage cells). These also include "developmental-stage specific promoters" that are temporally regulated, such as in early or late embryogenesis, during fruit ripening in developing seeds or fruit, in fully differentiated leaf, or at the onset of senescence. It is understood that the developmental specificity of the activation of a promoter and, hence, of the expression of the coding sequence under its control, in a transgene may be altered with respect to its endogenous expression. For example, when a transgene under the control of a floral promoter is transformed into a plant, even when it is the same species from which the promoter was isolated, the expression specificity of the transgene will vary in different transgenic lines due to its insertion in different locations of the chromosomes.

"Inducible promoter" refers to those regulated promoters that can be turned on in one or more cell types by a stimulus external to the plant, such as a chemical, light, hormone, stress, or a pathogen.

"Promoter activation" means that the promoter has become activated (or turned "on") so that it functions to drive the expression of a downstream genetic element. Constitutive promoters are continually activated. A regulated promoter may be activated by virtue of its responsiveness to various external stimuli (inducible promoter), or developmental signals during plant growth and differentiation, such as tissue specificity (floral-specific, anther-specific, pollen-specific, seed-specific, etc.) and development-stage specificity (vegetative-specific or floral-, shoot-, or apical meristem-specific, male germline-specific, female germline-specific etc).

"Operably-linked" refers to the association of nucleic acid sequences on a single nucleic acid fragment so that the function of one is affected by the other. For example, a promoter is operably-linked with a coding sequence or functional RNA when it is capable of affecting the expression of that coding sequence or functional RNA (i.e., that the coding sequence or functional RNA is under the transcriptional control of the promoter). Coding sequences can be operably-linked to regulatory sequences in sense or anti-sense orientation. "Unlinked" means that the associated genetic elements are not closely associated with one another and the function of one does not affect the other.

"Expression" refers to the transcription and stable accumulation of sense (mRNA) or functional RNA. Expression may also refer to the production of protein. "Overexpression" refers to levels of expression in transgenic organisms that exceeds levels of expression in normal or untransformed organisms.

"Non-specific expression" refers to constitutive expression or low level, basal ('leaky') expression in nondesired cells, tissues, or generations.

"Altered levels" refers to levels of expression in transgenic organisms that differs from that of normal or untransformed organisms.

The term "altered plant trait" means any phenotypic or genotypic change in a transgenic plant relative to the wild-type or non-transgenic plant host.

"Transcription Stop Fragment" refers to nucleotide sequences that contain one or more regulatory signals, such as polyadenylation signal sequences, capable of terminating transcription. Examples include the 3' non-regulatory regions of genes encoding nopaline synthase and the small subunit of ribulose bisphosphate carboxylase.

"Translation Stop Fragment" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. Excision of the translation stop fragment by SSR will leave a site-specific sequence in the coding sequence that does not interfere with proper translation using the initiation codon.

"Stop fragment" or "Blocking fragment" refers to a DNA fragment that is flanked by site-specific sequences that can block the transcription and/or the proper translation of a coding sequence resulting in an inactive transgene. When the blocking fragment contains polyadenylation signal sequences and other sequences encoding regulatory signals capable of terminating transcription, it can block the transcription of a coding sequence when placed in the 5' non-translated region, i.e., between the transcription start site and the ORF. When inserted in the coding sequence, a blocking fragment can block proper translation by disrupting the open reading frame of the coding sequence. DNA rearrangement by SSR can restore transcription and/or proper translatability. For example, excision of the blocking fragment by SSR leaves behind a site-specific sequence that allows transcription and/or proper translatability. A Transcription or Translational Stop Fragment will be considered a blocking fragment. A "stop fragment" can also block transcription by disrupting the gene in the non-transcribed region, for example, by its presence and/or orientation in promoter sequences either between the upstream promoter elements and the "TATA" box or between the TATA box and the transcription start site.

This process of excision of the stop fragment or blocking fragment will be referred to herein as "unblocking". When the blocking fragment is removed from the DNA by SSR, it will be appreciated by one skilled in the art that a site-specific sequence remains which can be transcribed and/or translated properly.

"Priming" or "enabling" refers to the removal of blocking sequences upstream of a promoter and/or gene, such that the gene can become activated in response to the appropriate environmental cue, stage of development, or its presence in a specific tissue/cell type. When a genetic element is enabled or primed by the removal of a blocking fragment, the promoter element may or may not be free to drive the expression of the downstream element. For example, a genetic construct comprising an inducible promoter separated by a stop fragment from a downstream gene to which it is operably linked, will be primed by the removal of the stop fragment; however, the downstream element will not be expressed until it is activated or induced. Thus, activation of a blocked gene will require enabling it and activation of the promoter driving the gene.

"Production tissue" refers to mature, harvestable tissue consisting of non-dividing, terminally-differentiated cells. It excludes young, growing tissue consisting of germline cells, meristematic cells, and those cells that are not fully differentiated.

"Germline" refers to cells that are destined to be gametes. Thus, the genetic material of germline cells is heritable.

"Common germline" refers to all germline cells prior to their differentiation into the male and female germline cells and, thus, includes the germline cells of developing embryo, vegetative SAM, floral SAM, and flower. Thus, site-specific excision in common germline results in excision from both male and female gametes.

"Male germline" refers to cells of the sporophyte (e.g., anther primordia, anther, microspore mother cells) or gametophyte (e.g., microspore, pollen) that are destined to be male gametes (sperm) and the male gametes themselves.

"Female germline" refers to cells of the sporophyte (e.g., pistil primordial pistil, ovule, macrospore mother cells) or gametophyte (e.g., macrospore, egg cell) that are destined to be female gametes or the female gametes themselves.

"Somatic" cells are all other cells in the organism that are not germline cells.

"Common germline promoter" refers to a promoter that is activated in germline cells prior to their differentiation into the male and female germlines. It also refers to a promoter that is activated in both male and female germline cells and to a set of promoters, one specific to the male germline and the other to the female germline. Thus, site-specific excision in common germline results in excision from both male and female gametes.

"Floral common germline promoter" refers to a promoter of flower or flower primordia genes whose expression occurs in "common germlines". It does not include male germline or female germline promoters, which are also expressed in the flower.

"Male germline promoter" refers to a promoter whose expression occurs in male (but not female) germline in the flower.

"Female germline promoter" refers to a promoter whose expression occurs in female (but not male) germline in the flower.

"Flower-" or "floral-specific promoter" refers to a promoter whose expression occurs in the flower or flower primordia. These promoters include floral common germline, male germline, and female germline promoters.

"Seed-specific promoter" refers to a promoter that is expressed only in the seed.

"Plant developmental stage-specific promoter" refers to a promoter that is expressed not constitutively but at specific plant developmental stage or stages. Plant development goes through different stages. In the context of this invention, the germline goes through different developmental stages starting, say, from fertilization through development of embryo, vegetative shoot apical meristem, floral shoot apical meristem, anther and pistil primordia, anther and pistil, micro- and macrospore mother cells, and macrospore (egg) and microspore (pollen).

"Synthetic anther promoter" refers to G9/SGB6 hybrid promoter (U.S. Pat. Nos. 5,470,359 and 5,837,850).

"Pollen-specific promoter" refers to a promoter that is only expressed in pollen, such as LAT52 (Twell et al. *Trends in Plant Sciences* 3:305 (1998)).

"Genetically linked" refers to physical linkage of transgenes, such that they co-segregate in progeny.

"Genetically unlinked" refers to the lack of physical linkage of transgenes such that they do not co-segregate in progeny.

"Morphological trait" refers to traits of morphology, such as shoots, roots, calli, tumors, flowers, or leaves.

"Tumorigenic" genes refer to genes that cause plant tumors, such as the T-DNA genes of *Agrobacterium tumefaciens*.

"Root inducing" genes refers to genes (e.g., rol A, B, and C genes of *Agrobacterium rhizogenes*) that cause root formation.

"Conditional and transient expression" refers to expression of a trait gene only in the selected generation or two. In the context of this invention, expression is triggered in the first generation and upon useful trait expression, the trait gene is removed from the germline.

"Activating transgene" refers to expression of a transgene. In the context of this invention, it refers to both enabling a blocked gene or enabling a blocked gene followed by activation of its promoter.

"Transformation" refers to the transfer of a foreign gene into the genome of a host organism. Examples of methods of plant transformation include *Agrobacterium*-mediated transformation (De Blaere et al. *Meth. Enzymol.* 143:277 (1987)) and particle-accelerated or "gene gun" transformation technology (Klein et al. *Nature* (London) 327:70-73 (1987); U.S. Pat. No. 4,945,050). The terms "transformed", "transformant" and "transgenic" refer to plants or calli that have been through the transformation process and contain a foreign gene integrated into their chromosome. The term "untransformed" refers to normal plants that have not been through the transformation process.

"Stably transformed" refers to cells that have been selected and regenerated on a selection media following transformation.

"Genetically stable" and "heritable" refer to chromosomally-integrated genetic elements that are stably maintained in the plant and stably inherited by progeny through successive generations.

"Wild-type" refers to the normal gene, virus, or organism found in nature without any known mutation.

"Genome" refers to the complete genetic material of an organism.

"Genetic trait" means a genetically determined characteristic or condition, which is transmitted from one generation to another. "Homozygous" state means a genetic condition existing when identical alleles reside at corresponding loci on homologous chromosomes. In contrast, "heterozygous" state means a genetic condition existing when different alleles reside at corresponding loci on homologous chromosomes. A "hybrid" refers to any offspring of a cross between two genetically unlike individuals. "Inbred" or "inbred lines" or "inbred plants" means a substantially homozygous individual or variety. This results from the continued mating of closely related individuals, especially to preserve desirable traits in a stock.

The term "ortholog" or "orthologous genes" refer to genes related by common phylogenetic descent. Orthologous genes are those genes from one species which correspond to a gene in another species that is related via a common ancestral species (a homologous gene), but which has evolved to become different from the gene of the other species.

"Selfing" or "self fertilization" refers to the transfer of pollen from an anther of one plant to the stigma (a flower) of that same said plant.

"Vegetative shoot apical meristem" refers to the cells found in the shoot apex of vegetative shoots that give rise to leaves and shoots.

"Floral shoot apical meristem" refers to the cells found in the shoot apex of floral meristem shoots that give rise to flowers and inflorescenes.

The term "sporophyte" means the diploid phase or cells of a plant.

The term "gametophyte" means the haploid phase or cells of a plant. This is the stage in a plant's life cycle between meiosis and fertilization. The male gametophyte includes the haploid phase or cells of the pollen and the female gametophyte includes the haploid phase or cells of the egg cell.

The term "plant life cycle" means a complete sequence of developmental events in the life of a plant, such as from fertilization to the next fertilization or from flowering in one generation to the next.

"Primary transformant" and "$T_0$ generation" refer to transgenic plants that are of the same genetic generation as the tissue which was initially transformed (i.e., not having gone through meiosis and fertilization since transformation).

"Secondary transformants" and the "$T_1$, $T_2$, $T_3$, etc. generations" refer to transgenic plants derived from primary transformants through one or more meiotic and fertilization cycles. They may be derived by self-fertilization of primary or secondary transformants or by crosses of primary or secondary transformants with other transformed or untransformed plants.

The present invention provides constructs and methods for the conditional or regulated expression of site-specific recombinases by employing intein-mediated protein splicing of split recombinases expressed under the control of a variety of constitutive, inducible, tissue-specific or development-stage specific promoters. The invention makes use of two inactive recombinase elements, one encoding a translationally fused ssrN-IntN chimeric protein under the control of plant regulatory sequences and the other encodes a translationally fused IntC-ssrC chimeric protein under the control of plant regulatory sequences. The promoters expressing the two inactive recombinase elements are either constitutively expressed or regulated. Additionally, the promoter controlling expression of each inactive recombinase element may be the same promoter or different promoters but with overlapping expression profiles. The two fusion proteins lack recombinase activity alone but when present together can undergo intein-mediated trans-protein splicing to form an active recombinase.

The inactive recombinase elements and trait expression constructs are introduced into plants in a variety of combinations so as to provide for the conditional SSR that can be used for various applications, such as for activation or excision of specific genetic traits encoded by the transgenes. By matching promoters (responsive to various inducers, plant tissues or plant developmental states with the recombinase systems), stop fragments and transgenes, virtually any trait may be expressed or excised at any plant development stage or in any plant generation.

Inactive Recombinase Elements

The invention makes use of a variety of constructs referred to herein as inactive recombinase elements. Each inactive recombinase element comprises regulatory sequences required to express a gene in a cell (e.g., appropriate promoter and terminator sequences), an intein or a portion thereof, and an extein. Typically, inactive recombinase elements have structures P-ssrN-IntN, and P-IntC-ssrC, where ssrN and ssrC refer to the N-terminal and C-terminal domains of the recombinase protein.

Promoters

The present invention makes use of a variety of plant promoters to drive the expression of either an inactive recombinase element, a recombinase element, or a transgene in a trait expression construct.

Regulated expression of transgene expression is possible by placing the transgene or recombinase elements under the control of promoters that may be conditionally regulated. Any promoter functional in a plant will be suitable including, but not limited to: constitutive plant promoters, plant tissue-specific promoters, plant development-stage specific promoters, inducible plant promoters, viral promoters, male germline-specific promoters, female germline-specific promoters, flower-specific promoters, and vegetative shoot apical meristem-specific promoters.

Several tissue-specific regulated genes and/or promoters have been reported in plants. These include genes encoding the seed storage proteins (e.g., napin, cruciferin, β-conglycinin, and phaseolin), zein or oil body proteins (e.g., oleosin), or genes involved in fatty acid biosynthesis e.g., acyl carrier protein, stearoyl-ACP desaturase, and fatty acid desaturases (fad 2-1)), and other genes expressed during embryo development (e.g., Bce4 [see, for example, EP 255378 and Kridl et al., *Seed Science Research* 1:209-219 (1991)]). Particularly useful for seed-specific expression is the pea vicilin promoter (Czako et al., *Mol. Gen. Genet.* 235(1): 33-40 (1992)). Other useful promoters for expression in mature leaves are those that are switched on at the onset of senescence, such as the SAG promoter from *Arabidopsis* (Gan et al., *Science*(Washington, D.C.) 270 (5244): 1986-8 (1995)).

A class of fruit-specific promoters expressed at or during anthesis through fruit development, at least until the beginning of ripening, is discussed in U.S. Pat. No. 4,943,674, the disclosure of which is hereby incorporated by reference. cDNA clones that are preferentially expressed in cotton fiber have been isolated (John et al., *Proc. Natl. Acad. Sci. U.S.A.* 89(13): 5769-73 (1992)). cDNA clones from tomato displaying differential expression during fruit development have been isolated and characterized (Mansson et al., *Mol. Gen. Genet.* 200:356-361 (1985); Slater et al., *Plant Mol. Biol.* 5:137-147 (1985)). The promoter for polygalacturonase gene is active in fruit ripening. The polygalacturonase gene is described in U.S. Pat. Nos. 4,535,060, 4,769,061, 4,801,590, and 5,107,065, which disclosures are incorporated herein by reference.

Mature plastid mRNA for psbA (one of the components of photosystem II) reaches its highest level late in fruit development, in contrast to plastid mRNAs for other components of photosystem I and II which decline to nondetectable levels in chromoplasts after the onset of ripening (Piechulla et al., *Plant Mol. Biol.* 7:367-376 (1986)). Recently, cDNA clones representing genes apparently involved in tomato pollen (McCormick et al., *Tomato Biotechnology* (1987)

Alan R. Liss: New York) and pistil (Gasser et al., *Plant Cell* 1:15-24 (1989)) interactions have also been isolated and characterized.

Other examples of tissue-specific promoters include those that direct expression in leaf cells following damage to the leaf (e.g., from chewing insects), in tubers (e.g., patatin gene promoter), and in fiber cells (e.g., E6, a developmentally-regulated fiber cell protein [John et al., *Proc. Natl. Acad. Sci. U.S.A.* 89(13): 5769-73 (1992)]). The E6 gene is most active in fiber, although low levels of transcripts are found in leaf, ovule and flower.

The tissue-specificity of some "tissue-specific" promoters may not be absolute and may be tested by one skilled in the art using the *diphtheria* toxin sequence. One can also achieve tissue-specific expression with "leaky" expression by a combination of different tissue-specific promoters (Beals et al., *Plant Cell,* 9:1527-1545 (1997)). Other tissue-specific promoters can be isolated by one skilled in the art (see U.S. Pat. No. 5,589,379).

Germline-specific promoters, responsive to male, female, or both male-female specific cell lineages are also useful in the present invention. For instance, transgenes can be expressed or removed from pollen by site-specific recombinase expression under the control of male germline-specific genes in anther primordia genes (e.g., *Arabidopsis Apetalla* 3 and *Pistilata* (PI) or their orthologs from other plant species), in sporophytic anther tissue (eg., Bcp I and TA29 promoters) or gametophytic pollen. Similarly, transgenes can be expressed or removed from ovules by site-specific recombinase expression under the control of female germline-specific genes in ovule primordia. Transgene can be expressed or removed from both male- and female-specific germlines by expression of an active site-specific recombinase gene under the control of a promoter for genes common to both male and female lineages in flower (e.g., *Arabidopsis agamous* gene or its orthologs in other species), in floral meristem (e.g., *Arabidopsis Apetala* 1, Leafy, and Erecta or their orthologs from other species), and in vegetative shoot apical meristem (e.g., *Arabidopsis* WUSCHEL (WUS) and SHOOT MERISTEMLESS (STM) or their orthologs from other species). Promoters of shoot apical meristem are especially useful for removing or expressing transformation marker genes early in tissue-culture following selection or in planta following a transformation phenotype.

Similarly, several inducible promoters ("gene switches") have been reported. Many are described in the review by Gatz (*Current Opinion in Biotechnology,* 7:168-172 (1996); Gatz, C., *Annu. Rev. Plant Physiol. Plant Mol. Biol.* 48: 89-108 (1997)). These include: the tetracycline repressor system, Lac repressor system, copper-inducible systems, salicylate-inducible systems (such as the PR1a system), and glucocorticoid- (Aoyama T. et al., *N-H Plant Journal* 11:605-612 (1997)) and ecdysome-inducible systems. Also included are the benzene sulphonamide- (U.S. Pat. No. 5,364,780) and alcohol- (WO 97/06269 and WO 97/06268)-inducible systems and glutathione S-transferase promoters. Other studies have focused on genes inducibly regulated in response to environmental stress or stimuli such as increased salinity, drought, pathogen, and wounding (Graham et al., *J. Biol. Chem.* 260:6555-6560 (1985); Graham et al., *J. Biol. Chem.* 260:6561-6554 (1985)) (Smith et al., *Planta* 168:94-100 (1986)). Accumulation of a metallocarboxypeptidase-inhibitor protein has been reported in leaves of wounded potato plants (Graham et al., *Biochem Biophys Res Comm* 101:1164-1170 (1981)). Other plant genes that have been reported to be induced include: methyl jasmonate, elicitors, heat-shock, anerobic stress, or herbicide safeners.

Site-Specific Recombinase Systems and Site-Specific Recombinases as Exteins

The present invention provides site-specific recombinase systems for use in the regulated expression or excision of transgenes. This is possible by division of a single recombinase enzyme into two extein fragments, each of which is fused to a split intein (either IntN or IntC) to produce the fusion proteins ssrN-IntN and IntC-ssrC. Protein precursors that contain a fusion of split recombinase and split intein fragment are fully transcribed into mRNA and translated into protein. However, the protein precursors so produced are inactive recombinase proteins by themselves. Only upon intein-mediated protein splicing is an active recombinase produced, by the ligation of ssrN and ssrC. Upon activation by the ssrN-ssrC recombinase's promoter, the enzyme is then able to interact with the second component of a SSR system (see below) to thereby enable a variety of reactions that may be engineered in a cell. Of course, as apparent to one skilled in the art, this interaction between ssrN and ssrC is only useful when ssrN and ssrC are derived from the same functional recombinase enzyme (e.g., CreN-CreC or FlpN-FlpC and not CreN-FlpC).

A SSR system consists of two elements: (1) an enzyme that binds to the DNA sequence specifically and catalyzes the recombination between DNA sequences if two or more of the sequences exist (recombinase); and (2) recombination sites having a characteristic DNA sequence. When the two DNA sequences are oriented in the same direction at a given interval on the same DNA molecule, the region held by these DNA sequences is excised from the DNA molecule, such as a plasmid, chromosome or the like. When the two DNA sequences are oriented in opposite directions on the same DNA molecule, the region held by these DNA sequences is inverted.

The site-specific sequences and their cognate recombinase enzymes can be from any natural SSR system. Well-known examples include Cre-lox, FLP/FRT, R/RS, Gin/gix, a pSR1 system, a cer system, and a fim system (for example, N. L. Craig, *Annu Rev. Genet.,* 22:17 (1988); Odell et al., *Use of site-specific recombination systems in plants. Homologous Recomb. Gene Silencing Plants* (1994), pp 219-70. Paszkowski, J., Ed. Kluwer: Dordrecht, Germany). Additionally, SSR systems have been identified in microorganisms such as phage, bacterium (e.g., *E. coli*), yeast and the like. When the SSR system separated from these microorganisms with the use of a Cre/lox system derived from P1 phage (WO 93/01283) is introduced into organisms (including plants) different from the organism from which this system had been derived, it behaves in the same way as in the original organism. The SSR system of yeast (*Zygosaccharomyces rouxii*) (pSR1 system [H. Matsuzaki et al., *J. Bacteriol.,* 172: 610 (1990)]) can also be used in accordance with the present invention. This pSR1 system also maintains its inherent function in higher plants (H. Onouchi et al., *Nucleic Acid Res.,* 19: 6373 (1991)).

Since the levels of the recombinase enzyme required are not expected to be high, several "specific" promoters can be used that may otherwise be too weak to express the gene of interest. Furthermore, since SSR depends on a threshold level of the recombinase, there may be a tolerance for leaky transcription that results in sub-threshold levels of recombinase.

Furthermore, increased "tissue-selectivity" to available regulated promoters is provided by decreasing the efficiency of wild-type Cre-mediated recombination, raising the threshold of recombinase required by using either a mutant site for SSR and/or a mutant recombinase that are not proficient in recombination. Such mutants are well known, at least for the Cre-lox system. The applicants have shown previously that when using safener-inducible Cre expression to activate the expression of a transgene (35S:luciferase), the use of a mutant lox site (lox72) and a wild type lox P site in Cre-mediated activation of the transgene reduces the basal activity of the promoter compared to using both wild type lox P sites (Yadav et al., WO 01/36595 A2; WO 00/17365 A2; EP 1115870 A2).

The non-specificity of recombinase expression can be further reduced (i.e., its expression specificity further increased) by other post-transcriptional approaches including: 1) using a chimeric recombinase gene that is poorly translated (such as having a non-ideal context sequence around the initiation codon following Kozak's rule; or having additional short ORFs in the 5' untranslated region as in yeast GCN4 mRNA; or having 3' UTR sequences that makes the mRNA unstable, as described by Pamela Green (Dept. of Biochemistry, Michigan State University, East Lansing, Mich.); or 2) using a mutant recombinase that has less cellular stability (i.e., shorter half-life). Such mutants could be made by adding PEST sequences (Sekhar et al., *Jrl. Receptor Signal Transduction Res.* 18 (2-3): 113-132 (1998)).

Once a system is developed in a given crop, it can be easily adapted for conditional expression of a variety of target trait genes.

Inteins

The present invention provides intein-mediated transprotein splicing of recombinase precursor proteins for controlling recombinase activity. Protein precursors that contain a fusion of split recombinase and split intein fragment are fully transcribed into mRNA and translated into protein. However, the protein precursors so produced can not form an active recombinase protein. Only upon intein-mediated protein splicing is an active recombinase protein produced. Thus, only the co-expression of the inactive precursors permits production of the active transgenic protein.

Although only 140 putative inteins have been found thus far in prokaryotes (archaea and eubacteria) and single cell eukaryotes such as algae and yeast (Perler, F. B. *Nucl. Acids. Res.* 28:344-345 (2000)), it is expected that many more will be identified in future genome sequencing projects. The present invention is not limited by the choice of intein; instead, the invention embodies those natural or synthetic inteins which are capable of catalyzing trans-splicing from a protein precursor to yield an active protein. These inteins can be modified to contain preferred codons for a specific host organism, as in the present invention.

Split inteins, composed of an N-terminal portion (IntN) and a C-terminal portion (IntC), have been discovered naturally (e.g., the split DnaE genes of *Synechocystis* sp. PCC6803) and made synthetically (see Mills, K. V. *Proc. Natl. Acad. Sci. USA.* 95: 3543-3548 (1998); Southworth, M. W. etal. *EMBO.* 17:918-926 (1998); Wu, H. et al. *Biochimica et Biophysica Acta* 187:422-432 (1998); Yamazaki, T. et al. *J. Am. Chem. Soc.* 120:5591-5592 (1998)). The literature provides abundant knowledge demonstrating the critical motifs required for functional inteins. Thus, it is envisioned that a variety of mutated split inteins could be generated, that would still possess the ability to self-excise from a protein precursor.

Inteins can be modified to contain preferred codons for a specific host. The present invention provides sequences for a split intein containing plant preferred codons. It is well known in the art how to generate a split intein sequence containing preferred codons for a specific host plant, by following the teachings of the present invention. It is expected that once an intein system is developed in a given crop, it can be easily adapted for conditional activation of a variety of target trait genes.

In like manner to that discussed above, it is obvious to one skilled in the art that the creation of split inteins appropriate for any bacterial or animal host could readily be created, using the teachings of the present invention.

Trait Expression Constructs

In addition to inactive recombinase elements, the present invention also utilizes trait expression constructs. Each trait expression construct comprises a floxed portion of DNA (optionally comprising a blocking fragment) and a transgene (TG). The trait expression construct becomes functional according to a variety of factors, two of which involve the position and choice of promoter (as discussed above).

Transgenes

Transgenes of the present invention will be those that convey a desirable phenotype on the transformed plant, or those that encode markers useful in breeding. Particularly useful transgenes will include, but not be limited to: genes conveying a specific phenotype on a plant or plant cell, genes encoding a transformation marker, genes encoding a morphological trait, and hormone biosynthetic genes.

Transgenes can encode functional RNAs or foreign proteins. Functional RNAs include sequences capable of silencing host endogenous genes or transgenes (e.g., transgenes that form hairpin RNA or double-stranded RNA). Foreign proteins will typically encode proteins that may be foreign to plant hosts. Such foreign proteins will include, for example: enzymes for primary or secondary metabolism in plants, proteins that confer disease or herbicide resistance, commercially useful non-plant enzymes, and proteins with desired properties useful in animal feed or human food. Additionally, foreign proteins encoded by the transgenes will include seed storage proteins with improved nutritional properties, such as the high-sulfur 10 kD corn seed protein or high-sulfur zein proteins. Additional examples of a transgene suitable for use in the present invention include genes for disease resistance (e.g., gene for endotoxin of *Bacillus thuringiensis*, WO 92/20802)), herbicide resistance (mutant acetolactate synthase gene, WO 92/08794)), seed storage protein (e.g., glutelin gene, WO 93/18643)), fatty acid synthesis (e.g., acyl-ACP thioesterase gene, WO 92/20236)), cell wall hydrolysis (e.g., polygalacturonase gene [D. Grierson et al., *Nucl. Acids Res.,* 14:8595 (1986)]), anthocyanin biosynthesis (e.g., chalcone synthase gene [H. J. Reif et al., *Mol. Gen. Genet.,* 199:208 (1985)]), ethylene biosynthesis (e.g., ACC oxidase gene [A. Slater et al., *Plant Mol. Biol.,* 5:137 (1985)]), active oxygen-scavenging system (e.g., glutathione reductase gene [S. Greer & R. N. Perham, *Biochemistry,* 25:2736 (1986)]), and lignin biosynthesis (e.g., phenylalanine ammonia-lyase gene, cinnamyl alcohol dehydrogenase gene, o-methyltransferase gene, cinnamate 4-hydroxylase gene, 4-coumarate-CoA ligase gene, and cinnamoyl CoA reductase gene [A. M. Boudet et al., *New Phytol.,* 129:203 (1995)]).

Transgenes may function as transformation markers. Transformation markers include selectable genes (e.g., antibiotic or herbicide resistance genes, which are used to select transformed cells in tissue culture), non-destructive screenable reporters (e.g., green fluorescent and luciferase genes), or a morphological marker (e.g., "shooty", "rooty", or "tumorous" phenotypes).

Additionally, transgenes may encode proteins that affect plant morphology and thus may also be used as markers. Morphological transformation marker genes include cytokinin biosynthetic genes, such as the bacterial gene encoding isopentenyl transferase (IPT). IPT gene was proposed as a marker for transformation by Ebumina et al. (*Proc. Natl. Acad. Sci. USA* 94:2117-2121 (1997)) and Kunkel et al. (*Nat Biotechnol.* 17(9): 916-919 (1999)). In the former case, the IPT gene was inserted inside a transposable element, whose excision following transformation resulted in the loss of the transposable element and the IPT gene. However, this method is inefficient (see Kunkel et al., supra), especially because of its low frequency of loss (1% or less). Kunkel et al., supra) proposed the use of an inducible IPT gene. However, this is also undesirable, since the bacterial IPT gene is not lost following transformation and that could be of concern from a regulatory point of view. Furthermore, it does not allow its use for retransformation for trait stacking. Thus, there is a need for an efficient regulated removal of morphological markers. Other morphological markers include developmental genes that can induce ectopic shoots (e.g., *Arabidopsis* STM, KNAT 1, or AINTEGUMANTA; Lec 1; *Brassica* "Babyboom" gene; rice OSH1 gene; or *maize* Knotted (Kn1) genes). Yet other morphological markers are the wild type T-DNA of Ti and Ri plasmids of *Agrobacterium* that induce tumors or hairy roots, respectively, or their constituent T-DNA genes for distinct morphological phenotypes, such as shooty (e.g., cytokinin biosynthesis gene) or rooty phenotype (e.g. rol C gene). Use of a morphological transformation marker to identify transformed tissue/organ(s) and its subsequent removal (leaving behind the transgene of interest) restores normal morphology and development to transgenic tissues. This is especially useful for in planta transformation, where the morphological marker is used to obtain abnormal transgenic organs that are then corrected by site-specific recombination to form morphologically and developmentally normal transgenic plants without going through the time and labor intensive tissue culture methods for transformation.

Floxed Blocking Fragments and/or Floxed Transgenes

Transgenes of the present invention are typically proceeded by a floxed blocking fragment. In another words, a DNA fragment flanked by site-specific sequences that can block the transcription and/or the proper translation of a transgene coding sequence is typically upstream of the transgene. This results in an inactive transgene. Only when an active recombinase enzyme is present in the cell may DNA rearrangement by SSR restore transcription and/or proper translatability of the transgene. This rearrangement physically removes the blocking fragment from the DNA, leaving only a single site-specific recombinase sequence that allows transcription and/or proper translatability. However, it can also involve inversion of a DNA element flanked by inverted recombinase sites.

Figure 4:
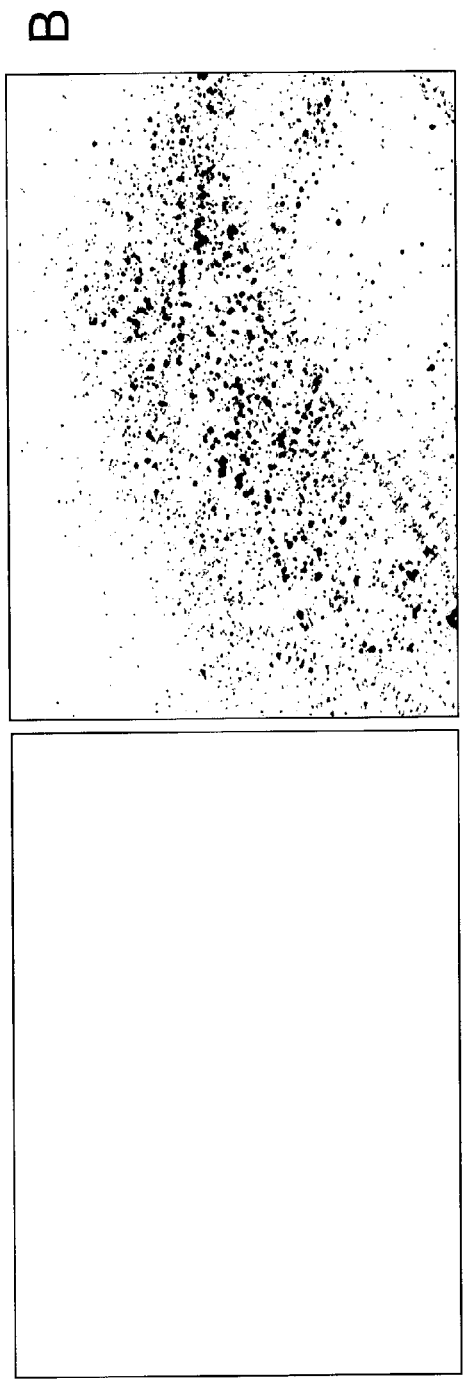
FIG. 4 shows transient co-expression of split Cre recombinase elements, resulting in SSR and activation of the GUS reporter gene.
Figure 4:
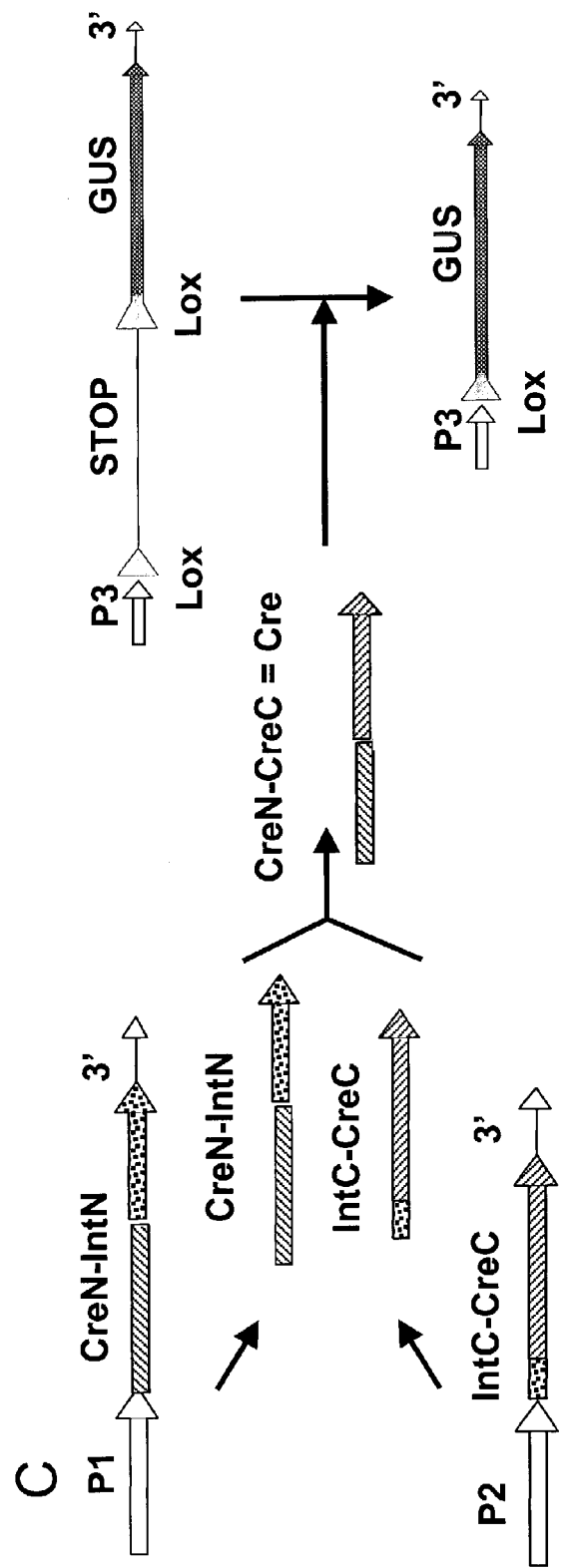

As apparent to one skilled in the art, it is also possible to incorporate other DNA between the site-specific recombinase sequences, which it is desirable to remove from the genome in a controlled manner according to activation of the recombinase enzyme. As illustrated in FIG. 4B (discussed below), for instance, it is possible to include the transgene itself within the floxed region and thereby remove the transgene from the plant genome at an appropriate time in the plant's development.

Plant Hosts

The present invention additionally provides plant hosts for transformation with the present constructs. Moreover, the host plant for use in the present invention is not particularly limited. Examples of herbaceous plant used as the host plant include: tobacco (*Tabacum* sp.), tomato (*Lycopersicom* sp), castor (*Ricinus* sp.), potato (*Solanum* sp.), carrot (*Dacus* sp.), oilseed rape (*Brassica* sp.), sunflower (*Helianthus* sp.), sugar beet (*Beta*), sugarcane (*Saccharium* sp.), cotton (*Gossypium* sp.), arabidopsis (*Arabidopsis* sp.), alfalfa (*Medicago* sp.), peas (*Pisum* sp.), soybean (*Glycine* sp.), rice (*Oryza* sp.), corn (*Zea* sp.), rye (*Secale* sp.), poplar (*Populus* sp.), eucalypti (*Eucalyptus*), and spruce (*Picea*).

Examples of arboreous plants used as the host plant include: poplar (*Populus*), eucalypti (*Eucalyptus*), acacia (*Acacia*), pear (*Pyrus*), apple (*Malus*), grape (*Vitis*), walnut (*Juglans*), plum (*Prunus*), rose (*Rosa*), and spruce (*Picea*). However, the host plants for use in the present invention are not limited thereto.

Plant Transformation

One skilled in the art recognizes that the expression level and regulation of a transgene in a plant can vary significantly from line to line. Thus, one has to test several lines to find one with the desired expression level and regulation. Once a line is identified with the desired regulation specificity of a chimeric inactive site-specific recombinase element, it can be crossed with lines carrying different inactive replicons or inactive transgenes for activation.

A variety of techniques are available and known to those skilled in the art for introduction of constructs into a plant cell host. These techniques include transformation with DNA employing *A. tumefaciens* or *A. rhizogenes* as the transforming agent, electroporation, particle acceleration, etc. (see, for example, EP 295959 and EP 138341). It is particularly preferred to use the binary type vectors of Ti and Ri plasmids of *Agrobacterium* spp. Ti-derived vectors transform a wide variety of higher plants, including monocotyledonous and dicotyledonous plants, such as soybean, cotton, rape, tobacco, and rice (Pacciotti et al., *Bio/Technology* 3:241 (1985); Byrne et al., *Plant Cell, Tissue and Organ Culture* 8:3 (1987); Sukhapinda et al., *Plant Mol. Biol.* 8:209-216 (1987); Lorz et al., *Mol. Gen. Genet.* 199:178 (1985); Potrykus, *Mol. Gen. Genet.* 199:183 (1985); Park et al., *J. Plant Biol.* 38(4):365-71 (1995); Hiei et al., *Plant J.* 6:271-282 (1994)). The use of T-DNA to transform plant cells has received extensive study and is amply described (EP 120516; Hoekema, In: *The Binary Plant Vector System*, Offset-drukkerij Kanters B. V.; Alblasserdam (1985), Chapter V; Knauf, et al., *Genetic Analysis of Host Range Expression by Agrobacterium*, In: *Molecular Genetics of the Bacteria-Plant Interaction*, Puhler, A. Ed., Springer-Verlag: New York, 1983, p 245; and An et al., *EMBO J.* 4:277-284 (1985)). For introduction into plants, the chimeric genes of the invention can be inserted into binary vectors as described in the Examples.

Other transformation methods are available to those skilled in the art, such as direct uptake of foreign DNA constructs (see EP 295959), techniques of electroporation (see Fromm et al. *Nature* (London) 319:791 (1986)) or high-velocity ballistic bombardment with metal particles coated with the nucleic acid constructs (see Kline et al. *Nature* (London) 327:70 (1987), and see U.S. Pat. No. 4,945,050). Once transformed, the cells can be regenerated by those skilled in the art. Of particular relevance are the recently described methods to transform foreign genes into commercially important crops, such as rapeseed (see De Block et al., *Plant Physiol.* 91:694-701 (1989)), sunflower (Everett et al., *Bio/Technology* 5:1201 (1987)), soybean (McCabe et al., *Bio/Technology* 6:923 (1988); Hinchee et al., *Bio/Technology* 6:915 (1988); Chee et al., *Plant Physiol.* 91:1212-1218 (1989); Christou et al., *Proc. Natl. Acad. Sci USA* 86:7500-7504 (1989); EP 301749), rice (Hiei et al., *Plant J.* 6:271-282 (1994)), and corn (Gordon-Kamm et al., *Plant Cell* 2:603-618 (1990); Fromm et al., *Biotechnology* 8:833-839 (1990)).

Transgenic plant cells are then placed in an appropriate selective medium for selection of transgenic cells that are then grown to callus. Shoots are grown from callus and plantlets generated from the shoot by growing in rooting medium. The various constructs normally will be joined to a marker for selection in plant cells. Conveniently, the marker may be resistance to a biocide (particularly an antibiotic such as kanamycin, G418, bleomycin, hygromycin, chloramphenicol, herbicide, or the like). The particular marker used will allow for selection of transformed cells as compared to cells lacking the DNA that has been introduced. Components of DNA constructs including transcription cassettes of this invention may be prepared from sequences which are native (endogenous) or foreign (exogenous) to the host. By "foreign" it is meant that the sequence is not found in the wild-type host into which the construct is introduced. Heterologous constructs will contain at least one region that is not native to the gene from which the transcription-initiation-region is derived.

To confirm the presence of the transgenes in transgenic cells and plants, a Southern blot analysis can be performed using methods known to those skilled in the art. Expression products of the transgenes can be detected in any of a variety of ways, depending upon the nature of the product (e.g., Western blot and enzyme assay). One particularly useful way to quantitate protein expression and to detect replication in different plant tissues is to use a reporter gene, such as GUS. Once transgenic plants have been obtained, they may be grown to produce plant tissues or parts having the desired phenotype. The plant tissue or plant parts may be harvested, and/or the seed collected. The seed may serve as a source for growing additional plants with tissues or parts having the desired characteristics.

DESCRIPTION OF THE PREFERRED EMBODIMENTS

The present invention enhances conditional expression of various genetic traits during specific times in an organism's life cycle, in specific tissues, or in a specific generation by tying the expression of these traits to split intein-mediated protein splicing site-specific recombinase systems. The two constructs of the invention are referred to as inactive recombinase elements and trait expression constructs. Each inactive recombinase element will comprise of 5' (including the promoter region) and 3' regulatory sequences operationally linked to the ORF for a chimeric ssrN-IntN fusion protein (N-inactive recombinase element) or IntC-ssrC fusion protein (C-inactive recombinase element). For example, if one desired to use the Cre recombinase for activation of a transgene, the necessary inactive recombinase elements would be P-CreN-IntN-3'UTR and P-IntC-CreC-3'UTR. The promoters (P) may be constitutive, inducible, tissue-specific or developmental stage-specific promoters. Furthermore, they can be the same or different but with overlapping expression profiles. Combinations of developmentally-regulated germline promoters are particularly useful. Transgenes of the present invention will express desirable genetic traits.

When N- and C-inactive recombinase elements are co-expressed in a cell following either chemical induction of one (or both) inactive recombinase element transgenes or a genetic cross, the recombinase activity is restored through split intein-mediated protein trans-splicing. This is diagramed in FIG. 1. First, an N- and a C-inactive recombinase element are present (represented as 35SPro-CreN-IntN-3' and 35SPro-IntC-CreC-3'). Upon activation of the 35S promoter within each construct, each inactive recombinase element is transcribed and translated, producing two inactive protein precursors (specifically, the CreN-IntN and IntC-CreC fusion proteins). Neither of these constructs are able to produce an active recombinase alone. However, upon co-expression of the two precursors in a cell, intein-mediated protein splicing is able to occur, thus producing an active recombinase in the form of a functional Cre recombinase protein.

There is great applicability for this invention in hybrid crops. For example, if one parent contains the N-inactive recombinase element and the other parent contains the C-inactive recombinase element, each inactive recombinase can be co-expressed in the F1 hybrid progeny under the control of the same or a different constitutive or regulated promoter (including chemically inducible promoters); if the promoters are different, however, they must have overlapping expression profiles. This results in the expression of a functional site-specific recombinase. The advantage of this strategy is that both parents can be homozygous for the inactive target trait locus and homozygous for the active trait locus in the hybrid progeny.

In another embodiment, at least one inactive recombinase element is flanked by site-specific sequences that are responsive to their functional recombinase, such that upon trait expression, the entire recombinase element is removed from the genome. The transgene expressing the other recombinase element can be under the same or a different promoter. This not only provides active recombinase containment but additionally prevents recombinase potential toxicity, when the threshold concentration of recombinase for recombination is lower than for recombinase potential toxicity.

Figure 2:
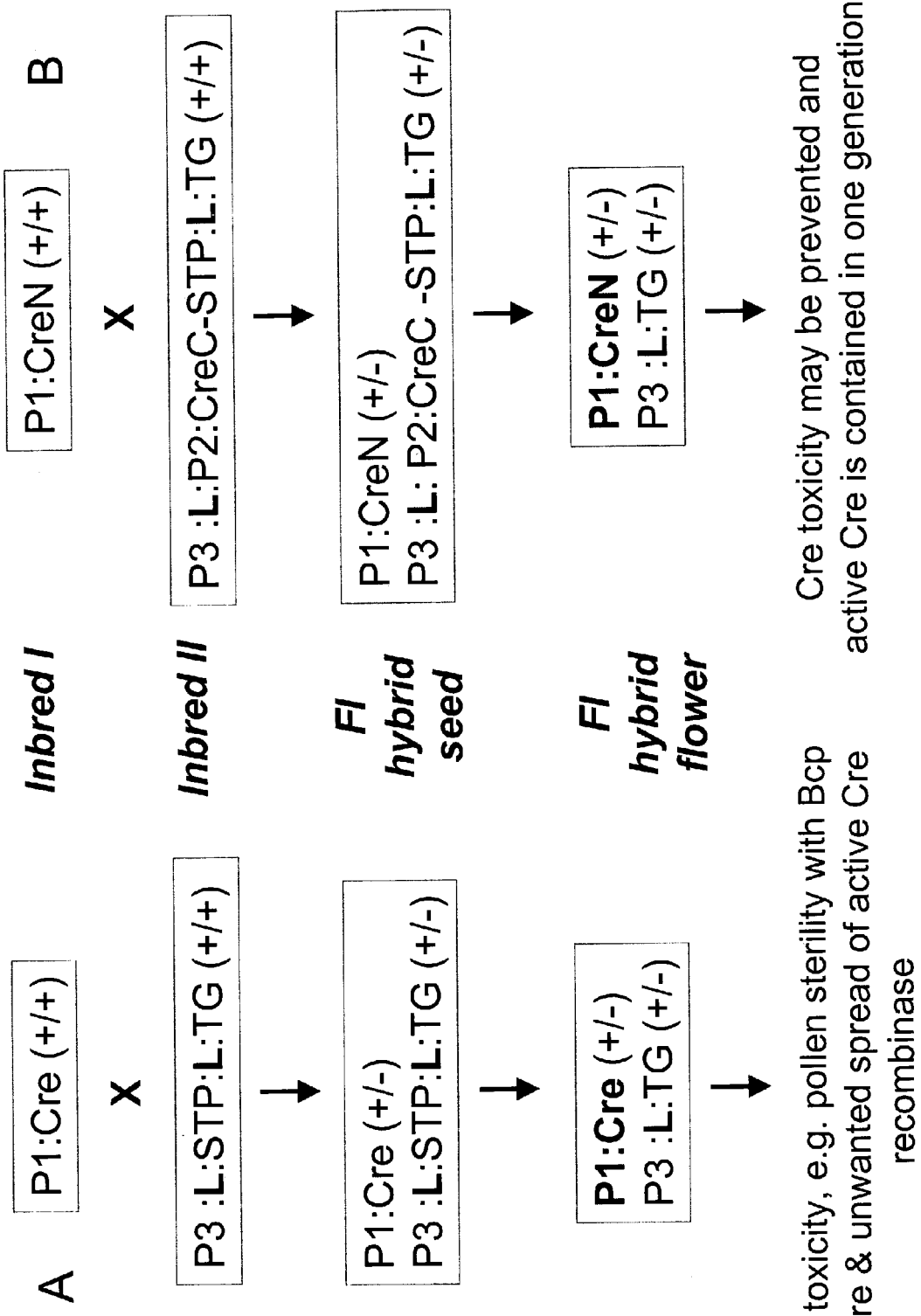
FIGS. 2 (A and B) are schematic diagrams illustrating the problems and solution concerning Cre potential toxicity and containment of active Cre, where the transgene remains in the F1 hybrid flower.
Figure 3:
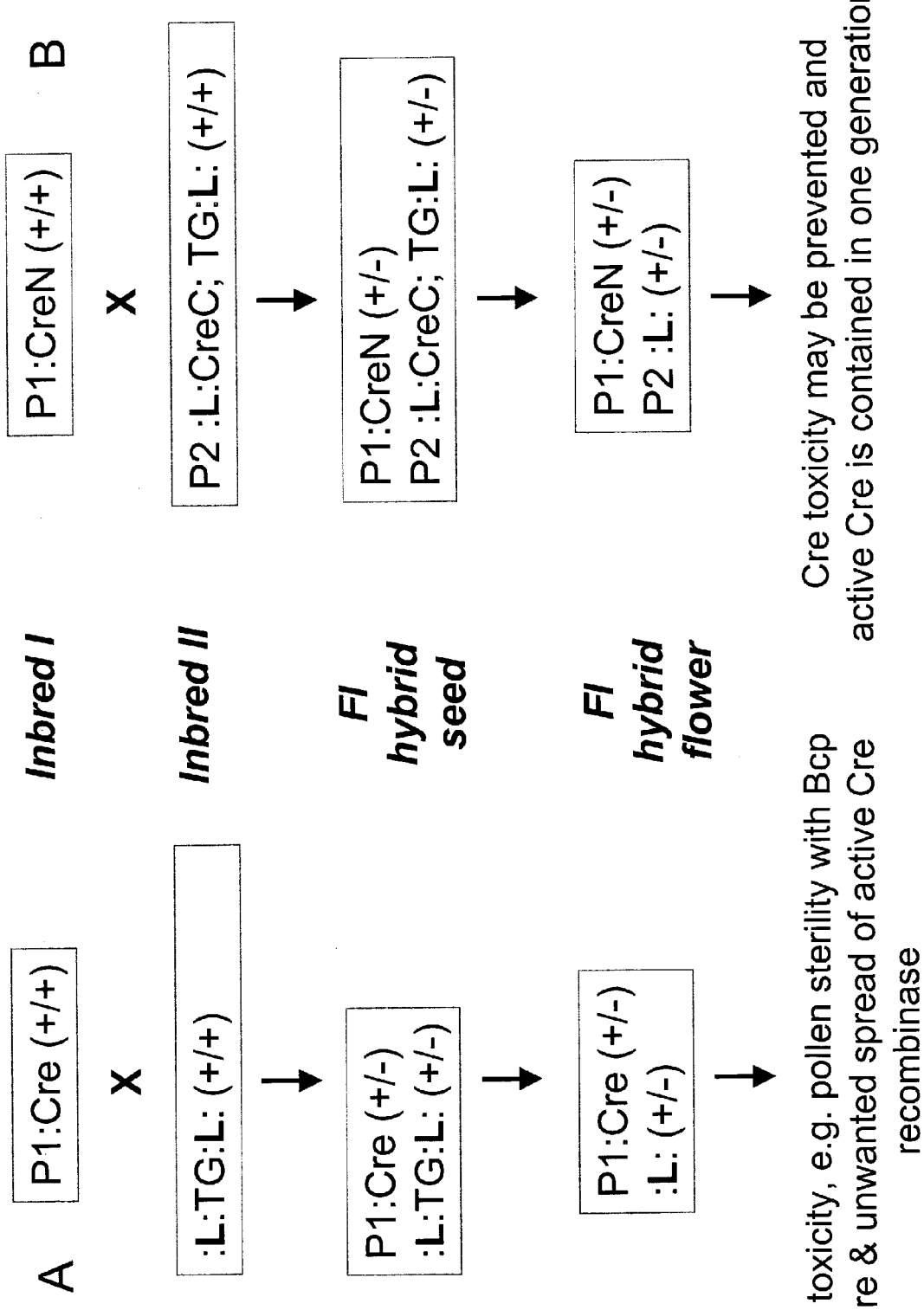
FIGS. 3 (A and B) are schematic diagrams illustrating the problems and solution concerning Cre potential toxicity and containment of active Cre, where the transgene is removed from the hybrid flower.

This is illustrated diagrammatically in FIGS. 2B and 3B, and contrasted to previous strategies (shown in FIGS. 2A and 3A, respectively). In both FIGS. 2 and 3, the transgenic constructs are identified for the first plant parent (identified as "Inbred I"), the other parent ("Inbred II"), the F1 hybrid seed, the F1 hybrid flower, and the F2 grain. A "+/+" following the description of the genetic construct indicates that the plant is homozygous for the locus, while a "+/−" indicates heterozygousity. Elements within each genetic construct which have not been previously defined are abbreviated according to the following:

P1—a promoter which controls expression of Cre (in FIGS. 2A and 3A) and CreN (in FIGS. 2B and 3B);

P2—a promoter that controls CreC;

P3—a promoter that controls TG when TG is unblocked;

CreN and CreC—encode chimeric protein fusions CreN-IntN and IntC-CreC, respectively;

L—Lox recombinase site responsive to the active Cre recombinase;

STP—a STOP fragment or blocking fragment;

TG—a trait gene or transgene; and

P3:L:STP:L:TG—an inactive TG, whose expression under the control of seed-specific P3 promoter is transcriptionally blocked by the presence of the STP DNA fragment.

In FIG. 2, the goal is to prevent Cre potential toxicity and contain active Cre within a single generation of the plant, while simultaneously maintaining the trait gene (TG) in the genome for all subsequent generations. P3:L:STP:L:TG is an inactive TG under the control of P3 promoter, whose expression is transcriptionally and/or translationally blocked by the presence of the 'blocking' or STOP (STP) DNA fragment. In FIG. 2A, P1 promoter controls expression of the Cre recombinase that removes the STP fragment to activate the TG. However, the Cre transgene under some plant promoters, such as that of the Bcp 1 gene, show Cre phytotoxicity even when they have the required regulation specificity. This results in pollen sterility with Bcp1:Cre and unwanted spread of active Cre recombinase in future generations. The problems mentioned above can be overcome, as illustrated in FIG. 2B, using the techniques of the present invention. P1 and P2 promoters control the expression of split recombinase elements, CreN and CreC, respectively, while promoter P3 controls the expression of TG. P1 and P2 promoters can be the same or different (but they must have sufficient overlap in their expression profiles to allow excision). P2:CreC and the STP fragment are flanked by Lox sites. Upon Cre activation (via intein-mediated protein splicing), the entire P2:CreC-STP construct is removed by SSR. This leaves TG to be expressed under the control of P3. Cre potential toxicity can be prevented using this strategy and active Cre is contained within a single generation.

In FIG. 3, the goal is to prevent Cre potential toxicity and contain active Cre within a single generation of the plant. In contrast to FIG. 2, however, where the TG is activated by SSR (by the inactive CreC element having its promoter within the Lox sites), the strategy illustrated in FIG. 3 permits trait gene removal by SSR. In FIG. 3A, showing previous methods well known in the art, :L:TG:L: is an active trait gene (TG) that is flanked by Lox sites and is removed from the genome by SSR. Promoter P1 controls the expression of Cre recombinase. As described above, however, the Cre transgene under some plant promoters (e.g., the Bcp 1 gene) show Cre potential toxicity even when they have the required regulation specificity, which can result in pollen sterility and unwanted spread of active Cre recombinase in future generations.

The solution to these difficulties is illustrated in FIG. 3B. P1 and P2 promoters control the expression of split recombinase elements, CreN and CreC, respectively. These P1 and P2 promoters can be the same or different (but must have sufficient overlap in their expression profiles to allow the excision). Upon Cre activation (via intein-mediated protein splicing), the entire :L:CreC; TG:L: construct is removed by SSR. This leaves only CreN in the plant genome, thereby preventing Cre potential toxicity, containing active Cre within one generation, and removing TG from the genome.

In another embodiment, one or both recombinase elements can be excised following expression of the active recombinase and trait transgene expression/excision to contain active recombinase activity in the desired generation as long the excision occurs after the desired SSR of the target transgene. In another embodiment, the transgenes of the two recombinase elements can be under the control of two different promoters with overlapping expression profiles to provide enhanced expression specificity or reduced Cre potential toxicity through more specific expression of Cre or lower level of Cre proteins made, respectively. For example, if a promoter is too strong for germline- or tissue specific-expression (e.g., AP3 in many cases), then expression of one recombinase element under a strong tissue-specific promoter and of the other recombinase element under a weaker, even if constitutive, promoter will result in lower and more specific Cre expression. Also, the two promoters having an overlapping expression profile can provide the required specificity and non-potential toxicity that they each individually cannot.

Conditionality to the first SSR is provided by either chemical application or a genetic cross. This results in co-expression of the inactive recombinase elements, which produces a functional recombinase in the presence of its cognate target gene/s. The latter is more amenable for hybrid crops. Chemical application on seeds or during germination is likely to overcome the chemical's cost and problems with its biokinetics into target cells. When chemically-induced, one or both of the inactive recombinase elements can be under the control of a chemically inducible promoter. Chemical application can also be done in the prior generation by using a relay of two or more SSR systems (WO 01/36595 A2). Thus, the chemical can be applied to germinating seeds in the last generation of seed production to induce one type of SSR. This would result in another type, say in late seed development of progeny seeds, that, in turn, results in a third type of SSR to express in early seeds, permitting removal of the trait locus. In another embodiment one or both inactive recombinase elements can be chemically repressible, such that the application of the chemical represses the site-specific recombinase to allow production of seeds with the transgenic trait. Here, in the absence of the chemical, such as in the farmers' field, the crop is genetically triggered to enable trait gene expression and/or its subsequent removal on cue.

The present invention has demonstrated intein-mediated trans-splicing of the Cre recombinase. Other cysteine residues in the Cre protein can be used. Similarly, Flp recombinase can be split at different cysteine residues and be fused to split inteins to function in the same way.

EXAMPLES

The present invention is further defined in the following Examples. These Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory: Cold Spring Harbor, N.Y. (1989) (Maniatis); by T. J. Silhavy, M. L. Bennan, and Enquist, L. W. Experiments with Gene Fusions, Cold Spring Harbor Laboratory: Cold Spring Harbor, N.Y. (1984); and by Ausubel, F. M. et al., Current Protocols in Molecular Biology, published. by Greene Publishing Assoc. and Wiley-Interscience (1987).

Restriction enzyme digestions, phosphorylations, ligations and transformations were done as described in Sambrook, J. et al., supra. Restriction enzymes were obtained from New England Biolabs (Boston, Mass.), GIBCO/BRL (Gaithersburg, Md.), or Promega (Madison, Wis.). Taq polymerase was obtained from Perkin Elmer (Branchburg, N.J.). Growth media was obtained from GIBCO/BRL (Gaithersburg, Md.).

The *Agrobacterium tumefaciens* strain LBA4404 was obtained from Dr. R. Schilperoot, Leiden (Hoekema et al. *Nature* 303:179-180 (1983)).

Transformation Protocols

Biolistic transformations were done essentially as described in U.S. Pat. No. 4,945,050, hereby incorporated by reference. Briefly, gold particles (1 mm in diameter) are coated with DNA using the following technique. Ten ug of plasmid DNAs are added to 50 uL of a suspension of gold particles (60 ug per uL). Calcium chloride (50 uL of a 2.5 M solution) and spermidine free base (20 uL of a 1.0 M solution) are added to the particles. The suspension is vortexed during the addition of these solutions. After 10 min, the tubes are briefly centrifuged (5 sec at 15,000 rpm) and the supernatant removed. The particles are resuspended in 200 uL of absolute ethanol, centrifuged again and the supernatant removed. The ethanol rinse is performed again and the particles resuspended in a final volume of 30 uL of ethanol. An aliquot (5 mL) of the DNA-coated gold particles can be placed in the center of a flying disc (Bio-Rad Labs, Medina, Ohio). The particles are then accelerated into the plant tissue with a PDS-1000/He (Bio-Rad Labs), using a helium pressure of 1000 psi, a gap distance of 0.5 cm, and a flying distance of 1.0 cm.

Where *Agrobacterium* transformations were done, the procedure was accomplished essentially as described Park et al. (*J. Plant Biol.* 38(4): 365-71 (1995)).

The meaning of abbreviations is as follows: "sec" means second(s), "min" means minute(s), "h" means hour(s), "d" means day(s), "μL" means microliter(s), "mL" means milliliter(s), "L" means liter(s), "μM" means micromolar, "mM" means millimolar, "M" means molar, "mmol" means millimole(s), "μmole" mean micromole(s), "g" means gram(s), "μg" means microgram(s), "ng" means nanogram(s), "U" means unit(s), "bp" means base pair(s), and "kB" means kilobase(s).

Example 1

Synthesis and Construction of Vectors Containing the Ssp DnaE Intein with Plant Preferred Codons This example describes the synthesis of the Ssp DnaE intein (IntN and IntC) using plant preferred codons. Then, the IntN and IntC were cloned into the pPCR-Script Amp plasmids to create vectors pPInt-n and pPInt-c.

Synthesis of SspE Intein Using Plant Preferred Codons

A naturally split intein has been identified in a split DnaE gene of *Synechocystis* sp. PCC6803 that mediates a protein trans-splicing reaction to produce a mature catalytic subunit of DNA polymerase III. Peptide sequences of the DnaE split intein are shown in Table 1.

TABLE 1

Peptide Sequences of the split intein DnaE from *Synechocystis* sp. PCC6803

| Intein | Length (AA) | Sequence* | SEQ ID NO |
|---|---|---|---|
| Int-n | 123 | CLSFGTEILTVEYGPLPIGKIVSEEINCSVYS VDPEGRVYTQAIAQWHDRGEQEVLEYELE DGSVIRATSDHRFLTTDYQLLAIEEIFARQL DLLTLENIKQTEEALDNH RLPFPLLDAGTIK | 1 |

TABLE 1-continued

Peptide Sequences of the split intein DnaE from *Synechocystis* sp. PCC6803

| Intein | Length (AA) | Sequence* | SEQ ID NO |
|---|---|---|---|
| Int-c | 36 | MVKVIGRRSLGVQRIFDIGLPQDHNFLLAN GAIAAN (C) | 2 |

*All four conserved motifs are underlined. Amino acid residues required for protein splicing are shown in bold text. A cysteine immediately downstream of Int-c (shown in parentheses) is also required for protein splicing.

To utilize this split intein in transgenic plants, synthetic genes of the split intein were synthesized and assembled.

At first, four groups of nucleotide oligomers were designed according to the peptide sequences of DnaE split intein *Synechocystis* sp. PCC6803 (Wu, H. et al. *Proc. Natl. Acad. Sci. USA*. 95:9226-9231 (1998)) and using the rules of genetic codon usage in plants (Murray, E. E., et al. *Nucl. Acids. Res.* 17:477-498 (1989)). These oligomers, catagorized into 5 different groups, are presented below in Table 2.

TABLE 2

Oligomers for Synthesis of the split intein DnaE from *Synechocystis* sp. PCC6803

| Group | Name | Length (bp) | Sequence (5'-3') | SEQ ID NO |
|---|---|---|---|---|
| 1 | IntN+1 | 75 | Tgcctttctttcggaactgagatcctt accgttgagtacggaccacttcctatt ggtaagatcgtttctgaggaa | 3 |
| 1 | IntN+2 | 75 | Attaactgctcagtgtactctgttgat ccagaaggaagagtttacactcaggct atcgcacaatggcacgatagg | 4 |
| 1 | IntN+3 | 75 | Ggtgaacaagaggttctcgagtacgag cttgaagatggatccgttattcgtgct acctctgaccatagattcttg | 5 |
| 1 | IntN+4 | 75 | Actacagattatcagcttctcgctatc gaggaaatctttgctaggcaacttgat ctccttactttggagaacatc | 6 |
| 1 | IntN+5 | 69 | Aagcagacagaagaggctcttgacaac cacagacttccattcccttttgctcgat gctggaaccatcaag | 7 |
| 2 | IntN-1 | 30 | Cttgatggttccagcatcgagcaaagg gaa | 8 |
| 2 | IntN-2 | 75 | Tggaagtctgtggttgtcaagagcctc ttctgtctgcttgatgttctccaaagt aaggagatcaagttgcctagc | 9 |
| 2 | IntN-3 | 75 | Aaagatttcctcgatagcgagaagctg ataatctgtagtcaagaatctatggtc agaggtagcacgaataacgga | 10 |
| 2 | IntN-4 | 75 | Tccatcttcaagctcgtactcgagaac ctcttgttcaccctatcgtgccattg tgcgatagcctgagtgtaaac | 11 |
| 2 | IntN-5 | 75 | Tcttccttctggatcaacagagtacac tgagcagttaatttcctcagaaacgat cttaccaataggaagtggtcc | 12 |

TABLE 2-continued

Oligomers for Synthesis of the split intein DnaE from *Synechocystis* sp. PCC6803

| Group | Name | Length (bp) | Sequence (5'-3') | SEQ ID NO |
|---|---|---|---|---|
| 2 | IntN-6 | 39 | Gtactcaacggtaaggatctcagttcc gaaagaaaggca | 13 |
| 3 | IntC+1 | 75 | Atggttaaggtgattggaagacgttct cttggtgttcaaaggatcttcgatatc ggattgccacaagaccacaac | 14 |
| 3 | IntC+2 | 36 | Tttcttctcgctaatggtgccatcgct gccaattgc | 15 |
| 4 | IntC-1 | 75 | Gcaattggcagcgatggcaccattagc gagaagaaagttgtggtcttgtggcaa tccgatatcgaagatcctttg | 16 |
| 4 | IntC-2 | 36 | Aacaccaagagaacgtcttccaatcac cttaaccat | 17 |
| 5 | Int-nN | 21 | Tgcctttctttcggaactgag | 18 |
| 5 | Int-nC | 24 | Tcacttgatggttccagcatcgag | 19 |
| 5 | Int-cN | 24 | Ccatggttaaggtgattggaagac | 20 |
| 5 | Int-cC | 21 | Gcaattggcagcgatggcacc | 21 |

Five oligomers in group 1 and six oligomers in group 2 were complemented and overlapped with one another. Group 1 oligomers were assembled to create the sense strand encoding Ssp DnaE Int-n, while Group 2 oligomers were assembled to create the antisense strand. Together, these two synthesized fragments yielded a double-stranded DNA sequence encoding Ssp DnaE Int-n, named as Plnt-n (nucleotide sequence presented as SEQ ID NO:22; amino acid sequence presented as SEQ ID NO:23). Similarly, two oligomers in group 3 and two oligomers in group 4 were also complemented and overlapped with one another, leading to assembly of a DNA fragment encoding Ssp DnaE Int-c with an additional C-terminal codon of cysteine. The DNA fragment was designated as Plnt-c (nucleotide sequence presented as SEQ ID NO:24; amino acid sequence presented as SEQ ID NO:25).

To assemble the DNA fragments, all oligomers in one group were pooled into a 100 µL phosphorylation reaction, which contained 200 pmole of each oligomer, 0.1 mM ATP, 20 units T4 polynucleotide kinase (Life Technologies, Rockville, Md.), and 1× forward reaction buffer (Life Technologies). After a 0.5 hr incubation at 37° C., the reaction was stopped and cleaned up using a Qiaquick Nucleotide Removal Kit (QIAGEN, Valencia, Calif.). The phosphorylated oligomers from groups 1 and 2 were then mixed and subjected to an annealing program on a GeneAmp PCR System 9600 (Perkin Elmer, Norwalk, Conn.), which included heating at 98° C. for 10 min followed by a 75° C. temperature drop at a slope of 1° C. per 5 min. The oligomers from groups 3 and 4 were mixed and subjected to the same annealing program. Finally, the annealed oligomers were ligated at 16° C. overnight in a 100 µL reaction containing 2 units of T4 DNA ligase (Life Technologies) and 1× ligase reaction buffer (Life Technologies). The reactions were cleaned up using QIAquick PCR Purification Kits (QIAGEN).

To amplify the correctly assembled DNA fragments, oligomers from Group 5 (SEQ ID NOs:18-21) were additionally synthesized and used as primers in two 50 µL PCR reactions. The reactions contained 0.25 mM of each dNTP, 2.5 units Pfu DNA polymerase (STRATAGENE, La Jolla, Calif.), and 1× Pfu buffer (STRATAGENE). In addition, one reaction included 25 pmole of oligomer Int-nN and Int-nC as primers (SEQ ID NOs:18 and 19, respectively) and 2 µL of Pint-n assembly reaction as template, while another included 25 nmole of oligomer Int-cN and Int-cC as primers (SEQ ID NOs:20 and 21, respectively) and 2 µL of Pint-c assembly reaction as template. The reactions were carried out on a GeneAmp PCR System 9600 for 35 cycles by following a program of denaturation at 94° C. (45 sec), annealing at 60° C. (45 sec), and 1 min amplification at 72° C. Oligomer int-nN and oligomer Int-nC amplified fragment Plnt-n and added a stop codon at its 3' end. Oligomer Int-cN and oligomer Int-cC amplified fragment Pint-C and created a NcoI site at its 5' end.

Creation of Vectors with IntN and IntC

Both PCR reactions were subjected to denatured agarose gel electrophoresis, gel isolation, and purification using a QIAquick Gel Extract Kit (QIAGEN). These Plnt-n and Plnt-c fragments were subcloned into pPCR-Script Amp plasmids, according to the manufacturer's instructions (PCR-Script Cloning Kit, STRATAGENE). This resulted in new plasmids pPlnt-n and pPlnt-c. Plasmid DNA was then generated and isolated from XL10-Gold *E. coli* cells (STRATAGENE) by using a QIAprep Miniprep Kit (QIAGEN). Plasmids pplnt-n and pPlnt-c were subjected to sequencing to confirm correct synthesis of Plnt-n and Plnt-c fragments.

Example 2

Construction Of Cre Recombinase-Intein Elements

Example 2 describes the construction of plasmids containing in-frame fusions of CreN-IntN and IntC-CreC.

The IntN and IntC of the Ssp DnaE split intein containing plant preferred codons (as prepared in Example 1) were each respectively fused to an artificially Created N-terminal and C-terminal portion of the bacterial Cre protein, yielding IntN-CreN and IntC-CreC, respectively. The starting plasmid for making both IntN-CreN and IntC-CreC genes was pNY102, which contains a plant gene encoding a modified bacterial Cre.

Construction of Plasmid pNY102 pNY102 was made by converting the XbaI site in pSK (Stratagene) into an Asp718 site and cloning an Asp718 fragment containing the chimeric transgene, 35S promoter: Cre ORF:3' octopine synthase (OCS) region, which encodes a functional Cre recombinase.

The 1411 bp region between Asp718 and the initiation codon of Cre ORF contains (5' to 3'):

18 bp polylinker sequence, 5'-GGTACCCGATCCAAT-TCC-3' (SEQ ID NO:26);

1334 bp of 35S promoter that is similar to nucleotides 3114 to 4453 in cloning vector pKANNIBAL [Genbank Accession No. AJ311873; Wesley, V. S., et al. *Plant J.* 27 (6): 581-590 (2001)]; and 60 bp 5' UTR of Petunia gene for chlorophyll a/b binding protein cab 22L [nucleotides 171-230 Genbank Accession No. X02359; Dunsmuir, P. *Nucleic Acids Res.* 13(7): 2503-2518 (1985)].

The Cre ORF is for bacteriophage P1 Cre gene for recombinase protein (Genbank Accession No. X03453 and in Sternberg, N. et al. *J. Mol. Biol.* 187(2): 197-212) except for a single base pair change (T to G) that was made at the fourth base of the ORF in order to introduce a Nco I site at the ATG, i,e., CCATGG, where the ATG is the initiation codon for Cre ORF, and resulting in a single amino acid substitution [Ser to Ala] at the second amino acid of the encoded Cre protein.

The 3' OCS region [complement of nucleotides 12541-11835 in Genbank Accession No. X00493 J05108 X00282; Barker, R.F., et al. *Plant Mol. Biol.* 2: 335-350 (1983)] is flanked by Sal 1/Xba I sites at the 5' end and Asp718 site at its 3' end.

Construction of Plasmid pGV947 Containing the Chimeric Gene Encoding the CreN-IntN Protein Fusion A 483 bp PCR product encoding the N-terminal 155 amino acid sequence (M to C) of the modified bacterial Cre protein described above was made using upper primer SEQ ID NO:27 and lower primer SEQ ID NO:28 on pNY102. Upper primer SEQ ID NO:27 contains a Nco I site with an ATG codon that serves as the translation initiation methionine of the Cre ORF. The 5' end of lower primer SEQ ID NO:28 contains a 13 bp sequence that is complementary to the 5' end of the DNA sequence encoding IntN ORF.

A 394 bp PCR product encoding the 123 amino acid sequence (C to K) of IntN protein was made by using upper primer SEQ ID NO:29 and lower primer SEQ ID NO:30 on plasmid PInt-n containing the IntN gene described above. The 5' end of SEQ ID NO:29 contains 14 bp of the sequence that is complementary to the 3' end of the CreN region described above and that overlaps SEQ ID NO:28. The 3' end of primer SEQ ID NO:30 contains a Sal I site.

A 849 bp PCR product encoding the complete 278 amino acid sequence of the CreN-IntN fusion protein was made by using upper primer SEQ ID NO:27 and lower primer SEQ ID NO:30 on a mixture of the 483 bp and 394 bp PCR products. The 3' end of the 483 bp fragment and the 5' end of the 394 bp fragment had a 27 bp sequence overlap. The 849 bp PCR product was cloned into pGEMT Easy vector (Stratagene) to yield plasmid pGV942, in which the Sal I site from the PCR product is adjacent to the Spe I site in the vector and its sequence was confirmed.

The 839 bp Nco I-Spe I fragment containing the CreN-IntN ORF was isolated from pGV942 and cloned into pNY1 02 to replace the Nco I-Xba I fragment containing full length Cre ORF to yield pGV947. Thus, pGV947 contains the chimeric 35S promoter: CreN-IntN ORF: 3' ocs transgene in a 3034 bp Asp718 fragment (SEQ ID NO:31) that is comprised of (5' to 3'):

18 bp (nucleotides 1-18) polylinker sequence, 5'-GGTAC-CCGATCCAATTCC-3' (SEQ ID NO:26);

1334 bp (nucleotides 19-1352) of 35S promoter that is similar to nucleotides 3114 to 4453 in cloning vector pKANNIBAL [Genbank Accession No. AJ311873; Wesley, V. S., et al. *Plant J.* 27(6): 581-590 (2001)];

60 bp (nucleotides 1353-1412) 5' UTR of Petunia gene for chlorophyll a/b binding protein cab 22L [nucleotides 171-230 Genbank Accession No. X02359; Dunsmuir, P. *Nucleic Acids Res.* 13(7): 2503-2518 (1985)];

837 bp (nucleotides 1413-2249) CreN-IntN ORF;

17 bp (nucleotides 2250-2266) sequence, 5'-GTCGA-CATAATCACTAG-3' (SEQ ID NO:32);

708 bp (nucleotides 2267-2974) 3' OCS region [complement of nucleotides 12541-11835 in Genbank Accession No. X00493 J05108 X00282; Barker, R. F., et al. *Plant Mol. Biol.* 2: 335-350 (1983)]; and 60 bp (nucleotides 2975-3034) polylinker sequence, 5'-CAGGACCTGCAGGCAT GCAAGCTTATC-GATACCGTCGACCTCGAGGGGGGGGCCCGGTA CC-3' (SEQ ID NO:33).

Construction of Plasmid pGV951 Containing the Chimeric Gene Encoding the IntC-CreC Protein Fusion A 128 bp PCR product encoding the 111 amino acid sequence of IntC ORF was made by using upper primer SEQ ID NO:34 and lower primer SEQ ID NO:35 on plasmid pint-c containing the IntC gene described above. Upper primer SEQ ID NO:34 contains a Nco I site with an ATG codon that serves as the translation initiation methionine of the IntC ORF. The 5' end of the lower primer SEQ ID NO:35 contains a 13 bp sequence that is complementary to the 5' end of the DNA sequence encoding the C-terminal portion of the Cre protein (see below).

A 588 bp PCR product (CreC) encoding the 564 amino acid sequence (Q to D) of the C-terminal portion of the bacterial Cre protein was made by using primers SEQ ID NO:36 and SEQ ID NO:37 on plasmid pNY102. The 5' end of SEQ ID NO:36 contains 13 bp of the sequence that is complementary to the 3' end of the IntC ORF and overlaps primer SEQ ID NO:35. The 3' end of SEQ ID NO:37 contains a Sal I site outside (i.e., 3' to) the CreC ORF.

A 688 bp PCR product containing the 225 amino acid sequence of the IntC-CreC fusion protein was made by using upper primer SEQ ID NO:30 and lower primer SEQ ID NO:33 on a mixture of the 128 bp and 588 bp PCR products. The 3' end of the 128 bp and the 5' end of the 588 bp fragments had a 26 bp sequence overlap. The 688 bp PCR product was cloned into pGEMT Easy vector (Stratagene) to yield plasmid pGV943 in which the Sal I site in the PCR product was adjacent to the Spe I site in the vector and its sequence was confirmed.

The 680 bp Nco I-Spe I fragment containing the CreN-IntN ORF was isolated from pGV943 and cloned into pNY102 to replace the Nco I-Xba I fragment containing full length Cre ORF to yield pGV951. pGV951 contains the chimeric 35S promoter: IntC-CreC ORF: 3' ocs transgene in a 2868 bp Asp718 fragment described by the 2873 bp sequence in SEQ ID No. 38 that is comprised of (5' to 3'):

18 bp (nucleotides 1-18) polylinker sequence, 5'-GGTAC-CCGATCCAATTCC-3' (SEQ ID NO:26);

1334 bp (nucleotides 19-1352) of 35S promoter that is similar to nucleotides 3114 to 4453 in cloning vector pKANNIBAL [Genbank Accession No. AJ311873; Wesley, V. S., et al. *Plant J.* 27(6), 581-590 (2001)];

60 bp (nucleotides 1353-1412) 5' UTR of Petunia gene for chlorophyll a/b binding protein cab 22L [nucleotides 171-230 Genbank Accession No. X02359; Dunsmuir, P. *Nucleic Acids Res.* 13(7): 2503-2518 (1985)];

678 bp (nucleotides 1413-2090) IntC-CreC ORF;

15 bp (nucleotides 2091-2105) sequence, 5'-GTCGAC-TATCACTAG-3' (SEQ ID NO:39);

708 bp (nucleotides 2106-2813) 3' OCS region [complement of nucleotides 12541-11835 in Genbank Accession No. X00493 J05108 X00282; Barker, R. F., et al. *Plant Mol. Biol.* 2: 335-350 (1983)]; and

• 60 bp (nucleotides 2814-2873) polylinker sequence,
5'-CAGGACCTGCAGGCATGCAAGCTTATCGATACCGTCGACCTCGAGGGGGGGCCCGGTACC-3'. (SEQ ID NO:33)

Example 3

Making Reporter Plasmid pGV801 as a Trait Expression Construct

Example 3 describes the construction of a trait expression construct, containing the reporter gene encoding β-glucuronidase, in plasmid pGV801.

A reporter plasmid construct pGV801 was made containing a 35S promoter: LoxP:nos:npt II:3'nos:LoxP:GUS ORF: 3' nos cassette. In it, the plant kanamycin resistance gene (nos:nptII:3'nos is a chimeric noplaine synthase (nos) promoter: neomycin phosphotransferase:3' nos transgene) flanked by loxP sites is inserted as a blocking fragment between a 35S promoter and the β-glucuronidase (GUS) coding region. The blocking fragment blocks the translation of GUS by interrupting the GUS coding sequence. However, upon Cre-lox excision, there is a single copy of loxP site left behind as a translational fusion with the GUS ORF thereby allowing glucuronidase expression.

The reporter plasmid construct, named pGV801, harbors the 5449 bp Sal I-Hind III fragment (SEQ ID NO:40), which contains the blocked reporter construct, 35S promoter: LoxP:nos:npt 11:3'nos:LoxP:GUS ORF:3' nos, and is comprised of (5' to 3'):

24 bp (nucleotides 1-24) polylinker sequence, 5'-GTCGACTCTAGAGGATCCAA TTCC-3' (SEQ ID NO:41);

1334 bp (nucleotides 25-1358) of 35S promoter (similar to nucleotides 3120 to 4453 in cloning vector pKANNIBAL [Genbank Accession No. AJ311873), although with a unique Bgl II site at position 405-410;

60 bp (nucleotides 1359-1418) 5' UTR of Petunia gene for chlorophyll a/b binding protein (corresponding to nucleotides 171-230, Genbank Accession No. X02359);

3 bp (nucleotides 1419-1421) of initiation codon ATG;

34 bp (nucleotides 1422-1455) Lox P sequence (5'-ATAACTTCGTATAGCATAC ATTATACGAAGTTAT -3') (SEQ ID NO:42);

5 bp (nucleotides 1456-1460), 5'-CCTAG-3' (part of Avr II site);

1776 bp (nucleotides 1461-3236) nos:npt II:3'nos sequence (complement of nucleotides 7483 to 9259 of pBin19, Gen Bank Accession No. U09365);

9 bp (nucleotides 3237-3245) 5'-CCTAGGTAA-3';

34 bp (nucleotides 3246-3279) Lox P sequence, 5'-ATAACTTCGTATAGCATAC ATTATACGAAGT-TAT -3' (SEQ ID NO:42);

3 bp (nucleotides 3280-3282) 5'-TAG-3';

1848 bp (nucleotides 3283-5130) corresponding to nucleotides 2555 to 4402 of pBI01, Genbank Accession No. U12639, starting from the 5th bp of the ORF encoding 1805 bp. Upon linkage with the upstream TAG, it modifies the GUS ORF such that the initiation codon is missing, the ORF is extended at the 5' end resulting in a 12-amino acid (ITSYSIHYTKLL; SEQ ID NO:58) N-terminal amino acid extension, and a changed $2^{nd}$ codon (from TTA to GTA) and $2^{nd}$ amino acid (from L to V) in the original GUS protein. Since the initiation Met is missing, this protein is not translatable;

22 bp (nucleotides 5131-5152) polylinker sequence, 5'-TGGGGAATTCCCCGG GGGTAC C-3' (SEQ ID NO:43);

279 bp (nucleotides 5153-5431) 3' region of nos (nucleotides 1824-2102 of nos gene, Genbank Accession No's. V00087, J01541); and 18 bp (nucleotides 5432-5449) polylinker sequence, 5'-GTCGACTCTAGAAA GCTT-3' (SEQ ID NO:44).

Upon Cre-mediated SSR, the blocking fragment flanked by the Lox P sites is removed from pGV801 and pBE801 (see below), leaving behind a single Lox P site. In the case of pBE801, the 3221 bp Bgl II-Hind III fragment containing the residual reporter, 35S promoter: LoxP:GUS ORF:3'nos cassette, is comprised of (5' to 3'):

954 bp (nucleotides 1-954) of 35S promoter (nucleotides 3500 to 4453 in cloning vector pKANNIBAL [Genbank Accession No. AJ31 1873]);

60 bp (nucleotides 955-1015) 5' UTR of Petunia gene for chlorophyll a/b binding protein (nucleotides 171-230, Genbank Accession No. X02359);

3 bp (nucleotides 1015-1017) of initiation codon ATG;

34 bp (nucleotides 1018-1051) Lox P sequence (5'-ATAACTTCGTATAGCATAC ATTATACGAAGTTAT -3') (SEQ ID NO:42);

3 bp (nucleotides 1052-1054) 5'-TAG-3';

1848 bp (nucleotides 1055-2902) corresponding to nucleotides 2555 to 4402 of pBI101, Genbank Accession No. U12639, starting from the $5^{th}$ bp of the ORF encoding 1805 bp. SSR restores a translatable GUS ORF by linking an initiation codon (ATG) to the 5' extended ORF. This results in a GUS fusion protein with a 13 N-terminal amino acid extension (MITSYSIHYTKLL; SEQ ID NO:59) and a changed amino acid (from L to V) in the $2^{nd}$ residue of the original GUS protein. This GUS fusion protein is active for β-glucuronidase enzyme activity;

22 bp (nucleotides 2903-2924) polylinker sequence, 5'-TGGGGAATTCCCCGG GGGTACC-3' (SEQ ID NO:43);

279 bp (nucleotides 2925-3203) 3' region of nos (nucleotides 1824-2102 of nos gene, Genbank Accession Nos. V00087, J01541); and 18 bp (nucleotides 3204-3221) polylinker sequence, 5'-GTCGACTCTAGAAA GCTT-3' (SEQ ID NO:44).

Example 4

Assay To Test Split Intein-Mediated Restoration Of Cre Recombinase Activity via Co-Bombardment This Example describes the transformation of inactive recombinase elements containing CreN-IntN and IntC-CreC and a trait expression construct containing GUS (from Examples 2 and 3) into tobacco leaves. When all three constructs were co-bombarded into the cells, positive GUS activity was observed.

Leaves of 2 month old wild type tobacco (var. Xanthi) plants were detached and placed on MS agar medium in petri dishes. Each leaf was bombarded with one of three DNA samples, with bombardment occurring in the following order:

| Order | Plasmid bombarded |
|---|---|
| 1. | 5 ug plasmid DNA without any GUS gene ('dummy' DNA) |
| 2. | 5 ug pGV801 reporter alone |
| 3. | 1 ug of pGV801 + pGV951 (35S: IntC-CreC:3'nos) + pGV947 (35S: CreN-IntN:3'nos) |

One day after bombardment the leaves were stained for GUS activity. FIG. 4A is a photograph of a GUS stained leaf bombarded with inactive reporter pGV801 alone. No GUS stain was observed with the 'dummy' DNA control (not shown) and with pGV801 alone (although, an occasional stained spot was seen that most likely represents homologous recombination between the Lox sites or contamination). In contrast, FIG. 4B is a photograph of a GUS stained leaf bombarded with the mixture of inactive reporter pGV801, pGV951, and pGV947. Significant positive GUS stained spots were observed in FIG. 4B. Specifically, GUS spots were seen only when pGV801 was co-bombarded with pGV951 and pGV947 in the manner of the positive control, i.e. pGV801 plus pNY102 (not shown).

The schematic shown in FIG. 4C graphically illustrates the molecular events that must occur for intein-mediated protein splicing of the Cre recombinase, which thereby permits excision of the blocking fragment and expression of the GUS reporter. First, two different inactive recombinase elements are present within a cell (represented as P1-CreN-IntN and P2-IntC-CreC). Upon activation of the promoter within each construct (which can be constitutive or regulated), each recombinase element is transcribed and translated, producing an inactive protein precursor (CreN-IntN and IntC-CreC). When both protein precursors are simultaneously present within the cell, intein-mediated protein splicing occurs to excise each intein fragment and form a peptide bond between CreN and CreC, thus producing an active and functional Cre protein. With the expression of Cre, the blocking STOP fragment in the P3:Lox:STP:Lox:Gus construct is excised by SSR, thereby allowing transcription and translation of the GUS transgene when P3 is activated.

Example 5

Constructs and Assay to Test Split Intein-Mediated Restoration of Cre Recombinase Activity via Parental Crossing This Example describes the creation of alternative inactive recombinase elements containing IntN-CreN and IntC-CreC and an alternative trait expression construct containing GUS (as compared to those of Examples 2 and 3). These constructs are necessary when the inactive recombinase elements are separately transformed into an N- and C-plant host, and then the progeny of those plants are tested for restoration of Cre recombinase activity leading to positive GUS expression.

Preparation of CreN-IntN and IntC-CreC Fusion Proteins

To demonstrate that functional Cre is made by co-expressing the CreN-IntN and IntC-CreC fusion proteins in stably transformed plants, three constructs were made: pBE801 containing a blocked GUS reporter gene, pBE952 containing 35S promoter:CreN-IntN ORF:3'ocs, and pBE953 containing 35S promoter: IntC-CreC ORF: 3' ocs transgene.

First, plasmid pBE801 was prepared according to the following methodology. The 5045 bp Bgl II-Hind III fragment corresponding to nucleotides 405 to 5449 of pGV801 described in Example 3 above was isolated and cloned into Bam HI-Hind II cut pBIB (D Becker. *Nucl. Acids. Res.* 18: 203 (1990)) binary vector to result in binary plasmid pBE801 in which the only selectable marker is the Kanamycin resistance gene in the blocking fragment. pBIB is derived from pBinl9 by deleting the nos:npt 11:3' nos selectable transgene. The 5045 bp Bgl II-Hind III fragment containing the reporter construct in pBE801 is comprised of (5' to 3'):

- 954 bp (nucleotides 1-954) of 35S promoter (nucleotides 3500 to 4453 in cloning vector pKANNIBAL [Genbank Accession No. AJ311873]);
- 60 bp (nucleotides 955-1015) 5' UTR of Petunia gene for chlorophyll a/b binding protein (nucleotides 171-230, Genbank Accession No. X02359);
- 3 bp (nucleotides 1015-1017) of initiation codon ATG;
- 34 bp (nucleotides 1018-1051) Lox P sequence (5'-ATAACTTCGTATAGCATAC ATTATACGAAGTTAT -3') (SEQ ID NO:42);
- 5 bp (nucleotides 1052-1056), 5'-CCTAG-3' (part of Avr II site);
- 1776 bp (nucleotides 1057-2832) nos:npt 11:3'nos sequence (complement of nucleotides 7483 to 9259, pBinl9, Genbank Accession No. U09365);
- 9 bp (nucleotides 2833-2841) 5'-CCTAGGTAA-3';
- 34 bp (nucleotides 2842-2875) Lox P sequence, 5'-ATAACTTCGTATAGCATAC ATTATACGAAGT-TAT -3' (SEQ ID NO:42);
- 3 bp (nucleotides 2876-2878) 5'-TAG-3';
- 1848 bp (nucleotides 2879-4726) corresponding to nucleotides 2555 to 4402 of pBI101, Genbank Accession No. U12639, starting from the $5^{th}$ bp of the ORF encoding 1805 bp. Upon linkage with the upstream TAG, it modifies the GUS ORF such that the initiation codon is missing, the ORF is extended at the 5' end resulting in a 12-amino acid (ITSYSIHYTKLL; SEQ ID NO:58) N-terminal amino acid extension, and a changed $2^{nd}$ codon (from TTA to GTA) and $2^{nd}$ amino acid (from L to V) in the original GUS protein. Since the initiation Met is missing, this protein is not translatable;
- 22 bp (nucleotides 4727-4748) polylinker sequence, 5' -TGGGGAATTCCCCGG GGGTAC C-3' (SEQ ID NO:43);
- 279 bp (nucleotides 4749-5027) 3' region of nos (nucleotides 1824-2102 of nos gene, Genbank Accession Nos. V00087, J01541); and
- 18 bp (nucleotides 5028-5045) polylinker sequence, 5'-GTCGACTCTAGAAA GCTT-3' (SEQ ID NO:44).

Plasmid pBE952 was created as described below. The 2594 bp Bgl II-Hind III fragment (the Bgl II site is at nucleotides 399-404 in the Asp718 fragment in pGV947 described above) containing the chimeric 35S promoter:CreN-IntN ORF: 3' ocs transgene was isolated from pGV947 and cloned into the pBE673 binary vector. The resultant binary plasmid, named pBE952, contained the chimeric transgene, 35S promoter:CreN-IntN ORF:3' ocs.

pBE673 was derived from pBinl9 (Genbank Accession No. U09365) by replacing the 1836 bp Bsu36a-Cla I fragment of pBin19 containing 3' end of nopaline synthase (nos) promoter, npt II (kanamycin resistance) ORF, and 3' nos region with a 949 bp Bsu36l-Cla I fragment containing (5' to 3'):

- 106 bp 3' end of nos promoter (nucleotides 468-574, Genbank Accession Nos. V00087 J01541; and Bevan, M., et al. *Nucleic Acids Res.* 11(2): 369-385 (1983));
- 5 bp GATCC sequence;

551 bp of *Streptomyces hygroscopicus* phosphothricin acetyl transferase (bar or basta resistance) ORF (Genbank Accession No. X 17220) except that the termination codon was changed from TGA to TAG;

8 bp TCCGTACC sequence; and 279 bp 3' nos region (nucleotides 1824-2102, Genbank Accession Nos. V00087 J01541 described above).

Finally, binary plasmid pBE953 was synthesized according to the following: 2868 bp Asp718 fragment containing the chimeric 35S promoter: IntC-CreC ORF: 3' ocs transgene (described above) was isolated from pGV951 and cloned into Asp718 digested pZBL11 binary vector [U.S. Pat. No. 5,968,793; EP 1003891; and WO 9859062] that contains a 35S:sulfonylurea resistant acetolactate synthase (ALS) transgene that confers resistance to sulfonylurea herbicide and serves as the plant selectable marker. The resultant binary plasmid, pBE953, contained the 35S promoter: IntC-CreC ORF: 3' ocs transgene in an orientation that is divergently transcribed compared to the 35S:ALS selection marker.

Stable Transformations

The binary plasmid pBE801 was introduced into *Agrobacterium* strain LBA4404 and used to transform wild type *Arabidopsis*. Kanamycin resistant transformants, designated 801 transformants, were selected and homozygous lines obtained that were tested positive for their ability to undergo Cre-mediated excision.

The binary plasmids pBE952 and pBE953 were introduced into *Agrobacterium* strain LBA4404 and used to transform into kanamycin resistant 801 (inactive reporter) *Arabidopsis* homozygous for the GUS reporter either separately or by co-transformation. 801 transformants co-transformed with both will be selected on sulfonylurea and bar and tested for GUS activation. 801 transformants carrying pBE952 alone and pBE953 alone will be crossed to each other and the GUS activation in the parent and crossed progeny will be analyzed.

Example 6

Construction of Flp Recombinase-Intein Elements

In a similar manner to that applied in Example 2, the present Example describes the construction of in-frame fusions of FlpN-IntN and IntC-FlpC, respectively. The IntN and IntC portion of the Ssp DnaE split intein containing plant preferred codons (from Example 1) will be each respectively fused to an artificially created N-terminal and C-terminal portion of the *maize*-optimized Flp protein, yielding IntN-FlpN and IntC-FlpC, respectively.

Construction of Chimeric Genes Encoding FlpN-IntN Protein

Flp ORF sequences were derived from plasmid pHP12891, which contains the chimeric SCP promoter:Flp ORF:3' PIN region transgene encoding a functional Flp recombinase. The SCP promoter is described in Bowen, Benjamin A., et al. (U.S. Pat. No. 6,072,050 A1). pHP12891 contains the chimeric SCP promoter:Flp ORF: 3' Pin transgene in a 2189 bp Bg I-Hind III fragment (SEQ ID NO:45) that is comprised of (5' to 3'):

21 bp (nucleotides 1-21) polylinker sequence, 5'-AGA TCT GAG CTT CTA GAG ATC-3' (SEQ ID NO:46);

498 bp (nucleotides 22-519) of synthetic promoter SCP, nucleotides 1-499 in Bowen, Benjamin A., et al. (U.S. Pat. No. 6,072,050 A1);

76 bp (nucleotides 520-595) including 5'UTR, 5'-ACA ATT ACC AAC AAC AAC AAA CAA CAA ACA ACA TTA CAA TTA CTA TTT ACA ATT ACA GTC GAC CCG GGA TCC AAC A-3' (SEQ ID NO:47);

1272 bp (nucleotides 596-1867) Flp ORF that was optimized for expression in maize (U.S. Pat. No. 5,929,301—see nucleotides 1-1272 of SEQ ID No: 1];

6 bp (nucleotides 1868-1873) sequence, 5'-GTT AAC-3';

310 bp (nucleotides 1874-2183) 3' UTR region of Potato gene for proteinase inhibitor II [similar to nucleotides 1525 to 1832, Genbank Accession No. X04118; Keil, M., et al. *Nucleic Acids Res.* 14 (14):5641-5650 (1986)]; and 6 bp (nucleotides 2184-2189), Eco RI site.

A 604 bp PCR product encoding the N-terminal 155 amino acid sequence (M to C) of maize-optimized Flp protein will be made using upper primer FlpN-UP (SEQ ID NO:48) and lower primer FlpN-LP (SEQ ID NO:49) on pHP12891. The SEQ ID NO:48 contains a Bam HI site in 5' UTR. The 5' end of SEQ ID NO:49 contains a 13 bp sequence that is complementary to the 5' end of the DNA sequence encoding split IntN.

A 395 bp PCR product encoding the 123 amino acid split IntN protein (C to K) was made by using upper primer IntN-UP (SEQ ID NO:50) and lower primer IntN-LP (SEQ ID NO:51) on plasmid pGV947 containing IntN ORF (described above in Example 2). The 5' end of SEQ ID NO:50 contains 14 bp of the sequence that is complementary to the 3' end of the FlpN ORF(described above). The 3' end of SEQ ID NO:51 contains an Asp718 site.

A 972 bp PCR product containing the complete 312 amino acid open reading frame of FlpN-IntN fusion protein was made by using primers SEQ ID NO:48 and SEQ ID NO:51 on a mixture of the 604 bp and 395 bp PCR products. The two PCR products had a 27 bp sequence overlap. The 950 bp Bam HI-Asp7l8 bp fragment was isolated from the 972 bp PCR product and cloned into pHP12891 cut with Bam HI and Asp 718 sites to yield plasmid pSCP-FlpN-IntN-3'Pin.

Thus, pSCP-FlpN-IntN-3' Pin contains the SCP promoter: FlpN-IntN ORF: 3' Pin transgene in a 1933 bp Bgl II-Eco RI fragment (SEQ ID NO:52) that is comprised of (5' to 3'):

21 bp (nucleotides 1-21) polylinker sequence, 5'-AGA TCT GAG CTT CTA GAG ATC -3' (SEQ ID NO:46);

498 bp (nucleotides 22-519) of synthetic promoter, SCP, nucleotides 1-499 in Bowen, Benjamin A., et al. (U.S. Pat. No. 6,072,050 A1);

76 bp (nucleotides 520-595) including 5'UTR, 5'-ACA ATT ACC AAC AAC AAC AAA CAA CAA ACA ACA TTA CAA TTA CTA TTT ACA ATT ACA GTC GAC CCG GGA TCC AAC A-3' (SEQ ID NO:47);

938 bp (nucleotides 596-1534) FlpN-IntN ORF;

77 bp (nucleotides 1535-1611) 3' end of Fip ORF in pHP12891;

6 bp (nucleotides 1612-1617) sequence, 5'-GTTMC-3';

310 bp (nucleotides 1618-1927) 3' UTR region of Potato gene for proteinase inhibitor 11 [similar to nucleotides 1525 to 1832, Genbank Accession No. X04118; Keil, M., et al. *Nucleic Acids Res.* 14 (14):

5641-5650 (1986)]; and 6 bp (nucleotides 1928-1933), Eco RI site.

Construction of a Chimeric Genes Encoding IntC-FlpC Protein

A 734 bp PCR product containing the 111 amino acid of IntC ORF was made by using upper primer IntC-UP (SEQ ID NO:53) and lower primer IntC-LP (SEQ ID NO:54) on plasmid pGV951 containing the IntC ORF. Primer IntC-UP contains the Nsi I site in 35S promoter. The 5' end of primer IntC-LP contains a 13 bp sequence that is complementary to the 5' end of the DNA sequence encoding the C-terminal portion of the Flp protein (see below).

A 729 bp PCR product encoding the 234 amino acid C-terminal portion of the maize optimized Flp protein (FlpC) was made by using primers FlpC-UP (SEQ ID NO:55) and FlpC-LP (SEQ ID NO:56) on plasmid pH12891. The 5' end of SEQ ID NO:55 contains 13 bp of the sequence that is complementary to the 3' end of the IntC ORF. The 3' end of SEQ ID NO:56 contains an Xba I site outside the Flp ORF.

A 1437 bp PCR product containing the 271 amino acid complete open reading frames of IntC-FlpC fusion protein will be made by using SEQ ID NO:53 and SEQ ID NO:56 on a mixture of the two PCR products that have a 26 bp sequence overlap. A 1416 bp Nsi I-Xba I fragment from the 1437 bp PCR product was isolated and cloned into pNY102 to yield plasmid p35S-IntC-FlpC-3'ocs.

Thus, p35S-IntC-FlpC-3'ocs contains the chimeric 35S promoter:IntC-FlpC ORF: 3' ocs transgene in a 3002 bp Asp718 fragment (SEQ ID NO:57) that is comprised of (5' to 3'):

18 bp (nucleotides 1-18) polylinker sequence, 5'-GGTAC-CCGATCCAATTCC-3' (SEQ ID NO:26);

1334 bp (nucleotides 19-1352) of 35S promoter that is similar to nucleotides 3114 to 4453 in cloning vector pKANNIBAL [Genbank Accession No. AJ311873; Wesley, V. S., et al. *Plant J.* 27 (6):581-590 (2001)];

60 bp (nucleotides 1353-1412) 5' UTR of Petunia gene for chlorophyll a/b binding protein cab 22L [nucleotides 171-230 Genbank Accession No. X02359; Dunsmuir, P. *Nucleic Acids Res.* 13 (7):2503-2518 (1985)];

816 bp (nucleotides 1413-2228) IntC-FlpC ORF;

6 bp (nucleotides 2229-2234) sequence, 5'-GTCTAG-3';

708 bp (nucleotides 2235-2942) 3' OCS region [complement of nucleotides 12541-11835 in Genbank Accession No. X00493 J05108 X00282; Barker, R. F., et al. *Plant Mol. Biol.* 2: 335-350 (1983)]; and 60 bp (nucleotides 2943-3002) polylinker sequence, 5'-CAGGACCTGCAGGCATGCAAGCTTATC-GATACCGTCGACCTC GAGGGGGGGCCCGG-TACC-3' (SEQ ID NO:33).

The two elements will be tested for function in plants as described above for Cre-intein elements, except that the GUS reporter will be blocked by a STOP fragment flanked by Frt sites.

What is claimed is:

1. An inactive recombinase element selected from the group consisting of:
   a) a DNA construct having the general structure in a 5' to 3' orientation comprising: P1-ssrN-IntN, wherein:
      (i) P1 is a promoter;
      (ii) ssrN encodes the N-terminal portion of a site-specific recombinase; and
      (iii) IntN encodes the N-terminal portion of a *Synechocystis* sp. PCC6803 naturally split intein wherein at least a portion of the IntN contains plant preferred codons;
   wherein each of P1, ssrN, and IntN are operably linked such that activation of the promoter results in the expression of the ssrN-IntN fusion protein lacking recombinase activity; and
   b) a DNA construct having the general structure in a 5' to 3' orientation comprising: P2-IntC-ssrC, wherein:
      (i) P2 is a promoter;
      (ii) ssrC encodes the C-terminal portion of a site-specific recombinase; and
      (iii) IntC encodes the C-terminal portion of a *Synechocystis* sp. PCC6803 naturally split intein wherein at least a portion of the IntC contains plant preferred codons;
   wherein each of P2, ssrC, and IntC are operably linked such that activation of the promoter results in the expression of the IntC-ssrC fusion protein lacking recombinase activity, and wherein the inactive recombinase elements of (a) and (b) when present together in a cell will form an active recombinase protein by intein-mediated trans-protein splicing.

2. An inactive recombinase element of claim 1, optionally flanked by repeated cognate recombinase sites, said cognate recombinase sites responsive to the active recombinase protein.

3. An inactive recombinase element according to either of claims 1 or 2, wherein ssrN and ssrC together form an active site-specific recombinase protein selected from the group consisting of Cre and Flp.

4. An inactive recombinase element according to either of claims 1 or 2, wherein P1 and P2 are the same.

5. An inactive recombinase element according to either of claims 1 or 2, wherein P1 and P2 are different.

6. An inactive recombinase element according to claim 1, wherein either P1 or P2 are independently selected from the group consisting of:
   a) constitutive promoters;
   b) tissue-specific promoters;
   c) developmental stage-specific promoters;
   d) inducible promoters;
   e) viral promoters;
   f) male germline promoters;
   g) female germline promoters;
   h) common germline promoters;
   i) chemically inducible promoters;
   j) plant floral common germline promoters;
   k) plant vegetative shoot apical meristem promoters; and
   l) plant floral shoot apical meristem promoters.

7. An intein-mediated site-specific recombination system comprising:
   a) an inactive recombinase element selected from the group consisting of:
      1) a DNA construct having the general structure in a 5' to 3' orientation comprising: P1-ssrN-IntN, wherein:
         (i) P1 is a promoter;
         (ii) ssrN encodes the N-terminal portion of a site-specific recombinase; and
         (iii) IntN encodes the N-terminal portion of a *Synechocystis* sp. PCC6803 naturally split intein wherein at least a portion of the IntN contains plant preferred codons;
      wherein each of P1, ssrN, and IntN are operably linked such that activation of the promoter results in the expression of the ssrN-IntN fusion protein lacking recombinase activity; and
      2) a DNA construct having the general structure in a 5' to 3' orientation comprising: P2-IntC-ssrC, wherein:
         (i) P2 is a promoter;
         (ii) ssrC encodes the C-terminal portion of a site-specific recombinase; and
         (iii) IntC encodes the C-terminal portion of a *Synechocystis* sp. PCC6803 naturally split intein wherein at least a portion of the IntC contains plant preferred codons;
      wherein each of P2, ssrC, and IntC are operably linked such that activation of the promoter results in the expression of the IntC-ssrC fusion protein lacking recombinase activity, and wherein the inactive recombinase elements of (1) and (2) when present together in a cell, will form an active recombinase protein by intein-mediated trans-protein splicing; and
   b) a site-specific recombinase DNA substrate, wherein said substrate undergoes site-specific recombination in the presence of the active recombinase.

8. An intein-mediated site-specific recombination system of claim 7, wherein the site-specific recombinase DNA substrate is a trait expression construct having the general structure in a 5' to 3' orientation: P3-RS-X-RS-TG, wherein:
   (i) P3 is a trait gene promoter;
   (ii) TG is a trait gene;

(iii) RS are directly repeated recombinase sites responsive to the recombinase;
(iv) X is a DNA fragment containing a stop fragment and optionally either:
   A) a DNA fragment encoding the N-terminal portion of a *Synechocystis* sp. PCC6803 naturally split intein; or
   B) a DNA fragment encoding the C-terminal portion of a *Synechocystis* sp. PCC6803 naturally split intein; or
   C) a transgene promoter capable of driving the transgene;
wherein the X DNA fragment is removed from the trait expression construct in the presence of the active recombinase, operably linking the P3 promoter and the trait gene, resulting in the expression of the trait gene under the control of the P3 promoter.

9. An intein-mediated site-specific recombination system of claim 8, wherein X comprises:
   (i) a stop fragment; and
   (ii) an inactive recombinase element of claim 1;
wherein the X DNA fragment is removed from the trait expression construct in the presence of the active recombinase.

10. An intein-mediated site-specific recombination system of claim 8, wherein the site-specific recombinase DNA substrate is a trait expression construct having the general structure in a 5' to 3' orientation: RS-X-RS, wherein:
   (i) RS are directly repeated recombinase sites responsive to the recombinase;
   (ii) X is a DNA fragment containing a trait gene and optionally one or all of the following:
      A) a stop fragment; or
      B) a promoter which drives a gene outside the repeated recombinase sites;
wherein the X DNA fragment is removed from the trait expression construct in the presence of the active recombinase.

11. An intein-mediated site-specific recombination system of claim 10, wherein X comprises:
   (i) a stop fragment; and
   (ii) an inactive recombinase element of claim 1;
wherein the X DNA fragment is removed from the trait expression construct in the presence of the active recombinase.

12. An intein-mediated site-specific recombination system according to any one of claims 7-11, wherein P1, P2, P3 and trait gene promoters are independently selected from the group consisting of:
   a) constitutive promoters;
   b) tissue-specific promoters;
   c) developmental stage-specific promoters;
   d) inducible promoters;
   e) viral promoters;
   f) male germline promoters;
   g) female germline promoters;
   h) common germline promoters;
   i) plant floral common germline promoters;
   j) plant vegetative shoot apical meristem promoters;
   k) plant floral shoot apical meristem promoters; and
   l) chemically inducible promoters.

13. An intein-mediated site-specific recombination system according to any one of claims 7-11, wherein the trait gene is selected from the group consisting of:
   a) genes encoding a transformation marker;
   b) genes encoding a morphological trait;
   c) genes encoding a site-specific recombinase,
   d) genes encoding a silencing construct, and
   e) genes conveying a specific phenotype on an organism or cell.

14. An intein-mediated site-specific recombination system according to any one of claims 7-11, wherein the active recombinase protein is independently selected from the group consisting of Cre and Flp.

15. An intein-mediated site-specific recombination system according to claim 14, wherein the recombinase sites are independently selected from the group consisting of wild type or mutant Lox and Frt sites.

16. An intein-mediated site-specific recombination system according to any one of claims 7-11, wherein the inactive recombinase elements and the trait expression construct may be genetically linked or unlinked.

17. An intein-mediated site-specific recombination system according to claim 16, wherein the inactive recombinase elements and the trait expression construct may be genetically unlinked and reside in different sexually compatible plants.

18. A method for regulating the expression of a trait gene in a plant cell comprising:
   a) providing a plant cell comprising an intein-mediated protein splicing site-specific recombination system of any one of claims 7-11; and
   b) growing the plant cell under conditions whereby site-specific recombination in the presence of the active recombinase results in activation or removal of trait gene(s).

19. A method for conditionally activating a trait gene in a hybrid plant comprising:
   a) providing an intein-mediated site-specific recombination system comprising:
      1) an inactive recombinase element having the general structure P1-ssrN-IntN, wherein:
         (i) P1 is a promoter;
         (ii) ssrN encodes the N-terminal portion of a site-specific recombinase; and
         (iii) IntN encodes the N-terminal portion of a *Synechocystis* sp. PCC6803 naturally split intein;
      2) an inactive recombinase element having the general structure P2-IntC-ssrC, wherein:
         (i) P2 is a promoter that may be the same or different than P1;
         (ii) ssrC encodes the C-terminal portion of a site-specific recombinase; and
         (iii) IntC encodes the C-terminal portion of a *Synechocystis* sp. PCC6803 naturally split intein;
      3) a trait expression construct having the general structure in a 5' to 3' orientation: P3-RS-STP-RS-TG, wherein:
         (i) P3 is a promoter;
         (ii) TG is a trait gene;
         (iii) RS is a recombinase site responsive to the recombinase; and
         (iv) STP is a stop fragment;
   b) providing a first transgenic plant comprising the inactive recombinase element of (a)(1) and the trait expression construct of (a)(3);
   c) providing a second transgenic plant comprising the inactive recombinase element of (a)(2) and the trait expression construct of (a)(3); and
   d) crossing the first and second plants to produce a hybrid plant such that:
      (i) co-expression of ssrN-intN and IntC-ssrC fusion proteins in the first generation hybrid plant results in intein-mediated protein splicing to generate a functional active recombinase; and
    (ii) excision of the stop fragment by the action of the active recombinase on the recombinase sites operably links P3 and the trait gene, resulting in the expression of the trait gene in the hybrid plant.

20. A method for conditionally removing a trait gene in a hybrid plant comprising:
    a) providing an intein-mediated site-specific recombination system comprising:
        1) an inactive recombinase element having the general structure P1-ssrN-IntN, wherein:
            (i) P1 is a promoter;
            (ii) ssrN encodes the N-terminal portion of a site-specific recombinase; and
            (iii) IntN encodes the N-terminal portion of a *Synechocystis* sp. PCC6803 naturally split intein;
        2) an inactive recombinase element having the general structure P1-IntC-ssrC, wherein:
            (i) P2 is a promoter that may be the same or different than P1;
            (ii) ssrC encodes the C-terminal portion of a site-specific recombinase; and
            (iii) IntC encodes the C-terminal portion of a *Synechocystis* sp. PCC6803 naturally split intein; and
        3) a trait expression construct having a foxed trait gene: RS-TG-RS, wherein:
            (i) TG is a trait gene; and
            (ii) RS are directly repeated recombinase sites responsive to the recombinase;
    b) providing a first transgenic plant comprising the inactive recombinase element of (a)(1) and the trait expression construct of (a)(3);
    c) providing a second transgenic plant comprising the inactive recombinase element of (a)(2) and the trait expression construct of (a)(3); and
    d) crossing the first and second plants to produce a hybrid plant such that:
        (i) co-expression of ssrN-intN and IntC-ssrC fusion proteins in the first generation hybrid plant results in intein-mediated protein splicing to generate a functional active recombinase; and
        (ii) excision of the trait gene results from the action of the active recombinase.

21. A method for regulating the expression of a trait gene in a plant cell comprising:
    I) providing a plant cell comprising an intein-mediated protein splicing site-specific recombination system of any one of claims 7-11; and
    II) growing the plant cell under conditions whereby site-specific recombination in the presence of the active recombinase results in activation or removal of trait gene(s),
    wherein any of the promoters are selected from the group consisting of:
    a) constitutive plant promoters;
    b) plant tissue-specific promoters;
    c) plant developmental stage-specific promoters;
    d) inducible plant promoters;
    e) viral promoters;
    f) male germline promoters;
    g) female germline promoters;
    h) common germline promoters;
    i) floral common germline promoters;
    j) vegetative shoot apical meristem promoters;
    k) floral shoot apical meristem promoters; and
    l) chemically-inducible promoters.

22. A method for regulating the expression of a trait gene in a plant cell comprising:
    I) providing a plant cell comprising an intein-mediated protein splicing site-specific recombination system of any one of claims 7-11; and
    II) growing the plant cell under conditions whereby site-specific recombination in the presence of the active recombinase results in activation or removal of trait gene(s),
    wherein the active recombinase protein is independently selected from the group consisting of Cre and Flp.

23. A method for regulating the expression of a trait gene in a plant cell comprising:
    I) providing a plant cell comprising an intein-mediated protein splicing site-specific recombination system of any one of claims 7-11; and
    II) growing the plant cell under conditions whereby site-specific recombination in the presence of the active recombinase results in activation or removal of trait gene(s),
    wherein the recombinase sites are independently selected from the group consisting of Lox and Frt.

24. A method for regulating the expression of a trait gene in a plant cell comprising:
    I) providing a plant cell comprising an intein-mediated protein splicing site-specific recombination system of any one of claims 7-11; and
    II) growing the plant cell under conditions whereby site-specific recombination in the presence of the active recombinase results in activation or removal of trait gene(s),
    wherein the inactive recombinase elements and the trait expression construct may be genetically linked or unlinked.

25. A method for regulating the expression of a trait gene in a plant cell comprising:
    I) providing a plant cell comprising an intein-mediated protein splicing site-specific recombination system of any one of claims 7-11; and
    II) growing the plant cell under conditions whereby site-specific recombination in the presence of the active recombinase results in activation or removal of trait gene(s),
    wherein the inactive recombinase elements and the trait expression construct may be genetically unlinked and reside in different plants.

26. A method for regulating the expression of a trait gene in a plant cell comprising:
    I) providing a plant cell comprising an intein-mediated protein splicing site-specific recombination system of any one of claims 7-11; and
    II) growing the plant cell under conditions whereby site-specific recombination in the presence of the active recombinase results in activation or removal of trait gene(s),
    wherein the plant is selected from the group consisting of: tobacco (*Tabacum* sp.), tomato (*Lycopersicom* sp), castor (*Ricinus* sp.), potato (*Solanum* sp.), carrot (*Dacus* sp.), oilseed rape (*Brassica* sp.), sunflower (*Helianthus* sp.), sugar beet (*Beta* sp.), sugarcane (*Saccharum* sp.), cotton (*Gossypium* sp.), arabidopsis (*Arabidopsis* sp.), alfalfa (*Medicago* sp.), peas (*Pisum* sp.), soybean (*Glycine* sp.), rice (*Oryza* sp.), corn (*Zea* sp.), rye (*Secale* sp.), poplar (*Populus* sp.), eucalypti (*Eucalyptus* sp.), and spruce (*Picea* sp.).

27. The method according to either of claims 19 or 20, wherein any of the promoters are selected from the group consisting of:
   a) constitutive plant promoters;
   b) plant tissue-specific promoters;
   c) plant developmental stage-specific promoters;
   d) inducible plant promoters;
   e) viral promoters;
   f) male germline promoters;
   g) female germlIne promoters;
   h) common germline promoters;
   i) floral common germline promoters;
   j) vegetative shoot apical meristem promoters;
   k) floral shoot apical meristem promoters; and
   l) chemically-inducible promoters.

28. The method according to either of claims 19 or 20, wherein the active recombinase protein is independently selected from the group consisting of Cre and Flp.

29. The method according to either of claims 19 or 20, wherein the recombinase sites are independently selected from the group consisting of Lox and Frt.

30. The method according to either of claims 19 or 20, wherein the inactive recombinase elements and the trait expression construct may be genetically linked or unlinked.

31. The method according to either of claims 19 or 20, wherein the inactive recombinase elements and the trait expression construct may be genetically unlinked and reside in different plants.

32. The method according to either of claims 19 or 20, wherein the plant is selected from the group consisting of: tobacco (*Tabacum* sp.), tomato (*Lycopersicom* sp), castor (*Ricinus* sp.), potato (*Solanum* sp.), carrot (*Dacus* sp.), oilseed rape (*Brassica* sp.), sunflower (*Helianthus* sp.), sugar beet (*Beta* sp.), sugarcane (*Saccharum* sp.), cotton (*Gossypium* sp.), arabidopsis (*Arabidopsis* sp.), alfalfa (*Medicago* sp.), peas (*Pisum* sp.), soybean (*Glycine* sp.), rice (*Oryza* sp.), corn (*Zea* sp.), rye (*Secale* sp.), poplar (*Populus* sp.), eucalypti (*Eucalyptus* sp.), and spruce (*Picea* sp.).

* * * * *

SEQUENCE LISTING

```
<160> NUMBER OF SEQ ID NOS: 59

<210> SEQ ID NO 1
<211> LENGTH: 123
<212> TYPE: PRT
<213> ORGANISM: Synechocystis sp. PCC6803

<400> SEQUENCE: 1

Cys Leu Ser Phe Gly Thr Glu Ile Leu Thr Val Glu Tyr Gly Pro Leu
1               5                   10                  15

Pro Ile Gly Lys Ile Val Ser Glu Glu Ile Asn Cys Ser Val Tyr Ser
            20                  25                  30

Val Asp Pro Glu Gly Arg Val Tyr Thr Gln Ala Ile Ala Gln Trp His
        35                  40                  45

Asp Arg Gly Glu Gln Glu Val Leu Glu Tyr Glu Leu Glu Asp Gly Ser
    50                  55                  60

Val Ile Arg Ala Thr Ser Asp His Arg Phe Leu Thr Thr Asp Tyr Gln
65                  70                  75                  80

Leu Leu Ala Ile Glu Glu Ile Phe Ala Arg Gln Leu Asp Leu Leu Thr
                85                  90                  95

Leu Glu Asn Ile Lys Gln Thr Glu Glu Ala Leu Asp Asn His Arg Leu
            100                 105                 110

Pro Phe Pro Leu Leu Asp Ala Gly Thr Ile Lys
        115                 120

<210> SEQ ID NO 2
<211> LENGTH: 37
<212> TYPE: PRT
<213> ORGANISM: Synechocystis sp. PCC6803

<400> SEQUENCE: 2

Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
```

```
            20                  25                  30
Ile Ala Ala Asn Cys
        35
```

<210> SEQ ID NO 3
<211> LENGTH: 75
<212> TYPE: DNA
<213> ORGANISM: Artificial Sequence
<220> FEATURE:
<223> OTHER INFORMATION: Modified from Synechocystis sp. PCC6803, to
      contain plant preferred codons

<400> SEQUENCE: 3
tgcctttctt tcggaactga gatccttacc gttgagtacg gaccacttcc tattggtaag    60
atcgtttctg aggaa                                                    75

<210> SEQ ID NO 4
<211> LENGTH: 75
<212> TYPE: DNA
<213> ORGANISM: Artificial Sequence
<220> FEATURE:
<223> OTHER INFORMATION: Modified from Synechocystis sp. PCC6803, to
      contain plant preferred codons

<400> SEQUENCE: 4
attaactgct cagtgtactc tgttgatcca gaaggaagag tttacactca ggctatcgca    60
caatggcacg atagg                                                    75

<210> SEQ ID NO 5
<211> LENGTH: 75
<212> TYPE: DNA
<213> ORGANISM: Artificial Sequence
<220> FEATURE:
<223> OTHER INFORMATION: Modified from Synechocystis sp. PCC6803, to
      contain plant
      preferred codons

<400> SEQUENCE: 5
ggtgaacaag aggttctcga gtacgagctt gaagatggat ccgttattcg tgctacctct    60
gaccatagat tcttg                                                    75

<210> SEQ ID NO 6
<211> LENGTH: 75
<212> TYPE: DNA
<213> ORGANISM: Artificial Sequence
<220> FEATURE:
<223> OTHER INFORMATION: Modified from Synechocystis sp. PCC6803, to
      contain plant preferred codons

<400> SEQUENCE: 6
actacagatt atcagcttct cgctatcgag gaaatctttg ctaggcaact tgatctcctt    60
actttggaga acatc                                                    75

<210> SEQ ID NO 7
<211> LENGTH: 69
<212> TYPE: DNA
<213> ORGANISM: Artificial Sequence
<220> FEATURE:
<223> OTHER INFORMATION: Modified from Synechocystis sp. PCC6803, to
      contain plant preferred codons

<400> SEQUENCE: 7
aagcagacag aagaggctct tgacaaccac agacttccat tccctttgct cgatgctgga    60

-continued accatcaag 69

<210> SEQ ID NO 8
<211> LENGTH: 30
<212> TYPE: DNA
<213> ORGANISM: Artificial Sequence
<220> FEATURE:
<223> OTHER INFORMATION: Modified from Synechocystis sp. PCC6803, to
      contain plant preferred codons

<400> SEQUENCE: 8
cttgatggtt ccagcatcga gcaaagggaa 30

<210> SEQ ID NO 9
<211> LENGTH: 75
<212> TYPE: DNA
<213> ORGANISM: Artificial Sequence
<220> FEATURE:
<223> OTHER INFORMATION: Modified from Synechocystis sp. PCC6803, to
      contain plant preferred codons

<400> SEQUENCE: 9
tggaagtctg tggttgtcaa gagcctcttc tgtctgcttg atgttctcca aagtaaggag 60
atcaagttgc ctagc 75

<210> SEQ ID NO 10
<211> LENGTH: 75
<212> TYPE: DNA
<213> ORGANISM: Artificial Sequence
<220> FEATURE:
<223> OTHER INFORMATION: Modified from Synechocystis sp. PCC6803, to
      contain plant preferred codons

<400> SEQUENCE: 10
aaagatttcc tcgatagcga gaagctgata atctgtagtc aagaatctat ggtcagaggt 60
agcacgaata acgga 75

<210> SEQ ID NO 11
<211> LENGTH: 75
<212> TYPE: DNA
<213> ORGANISM: Artificial Sequence
<220> FEATURE:
<223> OTHER INFORMATION: Modified from Synechocystis sp. PCC6803, to
      contain plant preferred codons

<400> SEQUENCE: 11
tccatcttca agctcgtact cgagaacctc ttgttcaccc tatcgtgcc attgtgcgat 60 agcctgagtg taaac 75

<210> SEQ ID NO 12
<211> LENGTH: 75
<212> TYPE: DNA
<213> ORGANISM: Artificial Sequence
<220> FEATURE:
<223> OTHER INFORMATION: Modified from Synechocystis sp. PCC6803, to
      contain plant preferred codons

<400> SEQUENCE: 12
tcttccttct ggatcaacag agtacactga gcagttaatt tcctcagaaa cgatcttacc 60
aataggaagt ggtcc 75

<210> SEQ ID NO 13
<211> LENGTH: 39
<212> TYPE: DNA

```
<213> ORGANISM: Artificial Sequence
<220> FEATURE:
<223> OTHER INFORMATION: Modified from Synechocystis sp. PCC6803,
      to contain plant preferred codons

<400> SEQUENCE: 13
gtactcaacg gtaaggatct cagttccgaa agaaaggca                              39

<210> SEQ ID NO 14
<211> LENGTH: 75
<212> TYPE: DNA
<213> ORGANISM: Artificial Sequence
<220> FEATURE:
<223> OTHER INFORMATION: Modified from Synechocystis sp. PCC6803, to
      contain plant preferred codons

<400> SEQUENCE: 14
atggttaagg tgattggaag acgttctctt ggtgttcaaa ggatcttcga tatcggattg      60
ccacaagacc acaac                                                       75

<210> SEQ ID NO 15
<211> LENGTH: 36
<212> TYPE: DNA
<213> ORGANISM: Artificial Sequence
<220> FEATURE:
<223> OTHER INFORMATION: Modified from Synechocystis sp. PCC6803, to
      contain plant preferred codons

<400> SEQUENCE: 15
tttcttctcg ctaatggtgc catcgctgcc aattgc                                36

<210> SEQ ID NO 16
<211> LENGTH: 75
<212> TYPE: DNA
<213> ORGANISM: Artificial Sequence
<220> FEATURE:
<223> OTHER INFORMATION: Modified from Synechocystis sp. PCC6803, to
      contain plant preferred codons

<400> SEQUENCE: 16
gcaattggca gcgatggcac cattagcgag aagaaagttg tggtcttgtg gcaatccgat      60
atcgaagatc ctttg                                                       75

<210> SEQ ID NO 17
<211> LENGTH: 36
<212> TYPE: DNA
<213> ORGANISM: Artificial Sequence
<220> FEATURE:
<223> OTHER INFORMATION: Modified from Synechocystis sp. PCC6803, to
      contain plant preferred codons

<400> SEQUENCE: 17
aacaccaaga gaacgtcttc caatcacctt aaccat                                36

<210> SEQ ID NO 18
<211> LENGTH: 21
<212> TYPE: DNA
<213> ORGANISM: Artificial Sequence
<220> FEATURE:
<223> OTHER INFORMATION: Modified from Synechocystis sp. PCC6803, to
      contain plant preferred codons

<400> SEQUENCE: 18
tgcctttctt tcggaactga g                                                21
```

<210> SEQ ID NO 19
<211> LENGTH: 24
<212> TYPE: DNA
<213> ORGANISM: Artificial Sequence
<220> FEATURE:
<223> OTHER INFORMATION: Modified from Synechocystis sp. PCC6803, to contain plant preferred codons

<400> SEQUENCE: 19
tcacttgatg gttccagcat cgag                                         24

<210> SEQ ID NO 20
<211> LENGTH: 24
<212> TYPE: DNA
<213> ORGANISM: Artificial Sequence
<220> FEATURE:
<223> OTHER INFORMATION: Modified from Synechocystis sp. PCC6803, to contain plant preferred codons

<400> SEQUENCE: 20
ccatggttaa ggtgattgga agac                                         24

<210> SEQ ID NO 21
<211> LENGTH: 21
<212> TYPE: DNA
<213> ORGANISM: Artificial Sequence
<220> FEATURE:
<223> OTHER INFORMATION: Modified from Synechocystis sp. PCC6803, to contain plant preferred codons

<400> SEQUENCE: 21
gcaattggca gcgatggcac c                                            21

<210> SEQ ID NO 22
<211> LENGTH: 369
<212> TYPE: DNA
<213> ORGANISM: Artificial Sequence
<220> FEATURE:
<223> OTHER INFORMATION: Modified from Synechocystis sp. PCC6803 SspE, to contain plant preferred codons
<220> FEATURE:
<221> NAME/KEY: CDS
<222> LOCATION: (1)..(369)
<223> OTHER INFORMATION: Modified from Synechocystis sp. PCC6803 SspE, to contain plant preferred codons

<400> SEQUENCE: 22

```
tgc ctt tct ttc gga act gag atc ctt acc gtt gag tac gga cca ctt      48
Cys Leu Ser Phe Gly Thr Glu Ile Leu Thr Val Glu Tyr Gly Pro Leu
1               5                   10                  15 cct att ggt aag atc gtt tct gag gaa att aac tgc tca gtg tac tct      96
Pro Ile Gly Lys Ile Val Ser Glu Glu Ile Asn Cys Ser Val Tyr Ser
            20                  25                  30 gtt gat cca gaa gga aga gtt tac act cag gct atc gca caa tgg cac     144
Val Asp Pro Glu Gly Arg Val Tyr Thr Gln Ala Ile Ala Gln Trp His
        35                  40                  45 gat agg ggt gaa caa gag gtt ctc gag tac gag ctt gaa gat gga tcc     192
Asp Arg Gly Glu Gln Glu Val Leu Glu Tyr Glu Leu Glu Asp Gly Ser
    50                  55                  60 gtt att cgt gct acc tct gac cat aga ttc ttg act aca gat tat cag     240
Val Ile Arg Ala Thr Ser Asp His Arg Phe Leu Thr Thr Asp Tyr Gln
65                  70                  75                  80 ctt ctc gct atc gag gaa att ttt gct agg caa ctt gat ctc ctt act     288
Leu Leu Ala Ile Glu Glu Ile Phe Ala Arg Gln Leu Asp Leu Leu Thr
                85                  90                  95 ttg gag aac att aag cag aca gaa gag gct ctt gac aac cac aga ctt     336
```

```
Leu Glu Asn Ile Lys Gln Thr Glu Glu Ala Leu Asp Asn His Arg Leu
            100                 105                 110 cca ttc cct ttg ctc gat gct gga acc atc aag                          369
Pro Phe Pro Leu Leu Asp Ala Gly Thr Ile Lys
        115                 120

<210> SEQ ID NO 23
<211> LENGTH: 123
<212> TYPE: PRT
<213> ORGANISM: Artificial Sequence
<220> FEATURE:
<223> OTHER INFORMATION: Modified from Synechocystis sp. PCC6803 SspE,
      to contain plant preferred codons

<400> SEQUENCE: 23

Cys Leu Ser Phe Gly Thr Glu Ile Leu Thr Val Glu Tyr Gly Pro Leu
1               5                   10                  15

Pro Ile Gly Lys Ile Val Ser Glu Glu Ile Asn Cys Ser Val Tyr Ser
            20                  25                  30

Val Asp Pro Glu Gly Arg Val Tyr Thr Gln Ala Ile Ala Gln Trp His
        35                  40                  45

Asp Arg Gly Glu Gln Glu Val Leu Glu Tyr Glu Leu Glu Asp Gly Ser
    50                  55                  60

Val Ile Arg Ala Thr Ser Asp His Arg Phe Leu Thr Thr Asp Tyr Gln
65                  70                  75                  80

Leu Leu Ala Ile Glu Glu Ile Phe Ala Arg Gln Leu Asp Leu Leu Thr
                85                  90                  95

Leu Glu Asn Ile Lys Gln Thr Glu Glu Ala Leu Asp Asn His Arg Leu
            100                 105                 110

Pro Phe Pro Leu Leu Asp Ala Gly Thr Ile Lys
        115                 120

<210> SEQ ID NO 24
<211> LENGTH: 111
<212> TYPE: DNA
<213> ORGANISM: Artificial Sequence
<220> FEATURE:
<223> OTHER INFORMATION: Modified from Synechocystis sp. PCC6803 SspE,
      to contain plant preferred codons
<220> FEATURE:
<221> NAME/KEY: CDS
<222> LOCATION: (1)..(111)
<223> OTHER INFORMATION: Modified from Synechocystis sp. PCC6803 SspE,
      to contain plant preferred codons

<400> SEQUENCE: 24 atg gtt aag gtg att gga aga cgt tct ctt ggt gtt caa agg atc ttc       48
Met Val Lys Val Ile Gly Arg Arg Ser Leu Gly Val Gln Arg Ile Phe
1               5                   10                  15 gat atc gga ttg cca caa gac cac aac ttt ctt ctc gct aat ggt gcc       96
Asp Ile Gly Leu Pro Gln Asp His Asn Phe Leu Leu Ala Asn Gly Ala
            20                  25                  30 atc gct gca aat tgc                                                  111
Ile Ala Ala Asn Cys
        35

<210> SEQ ID NO 25
<211> LENGTH: 37
<212> TYPE: PRT
<213> ORGANISM: Artificial Sequence
<220> FEATURE:
<223> OTHER INFORMATION: Modified from Synechocystis sp. PCC6803 SspE,
      to contain plant preferred codons
```

```
<400> SEQUENCE: 25

Met Val Lys Val Ile Gly Arg Arg Ser Leu Gly Val Gln Arg Ile Phe
1               5                  10                  15

Asp Ile Gly Leu Pro Gln Asp His Asn Phe Leu Leu Ala Asn Gly Ala
            20                  25                  30

Ile Ala Ala Asn Cys
        35

<210> SEQ ID NO 26
<211> LENGTH: 18
<212> TYPE: DNA
<213> ORGANISM: Artificial Sequence
<220> FEATURE:
<223> OTHER INFORMATION: 18 bp polylinker

<400> SEQUENCE: 26
ggtacccgat ccaattcc                                                 18

<210> SEQ ID NO 27
<211> LENGTH: 26
<212> TYPE: DNA
<213> ORGANISM: Artificial Sequence
<220> FEATURE:
<223> OTHER INFORMATION: Primer

<400> SEQUENCE: 27
gaccatggcc aatttactga ccgtac                                        26

<210> SEQ ID NO 28
<211> LENGTH: 27
<212> TYPE: DNA
<213> ORGANISM: Artificial Sequence
<220> FEATURE:
<223> OTHER INFORMATION: Primer

<400> SEQUENCE: 28
cgaaagaaag gcagcagcga tcgctat                                       27

<210> SEQ ID NO 29
<211> LENGTH: 29
<212> TYPE: DNA
<213> ORGANISM: Artificial Sequence
<220> FEATURE:
<223> OTHER INFORMATION: Primer

<400> SEQUENCE: 29
atagcgatcg ctgctgcctt tctttcgga                                     29

<210> SEQ ID NO 30
<211> LENGTH: 27
<212> TYPE: DNA
<213> ORGANISM: Artificial Sequence
<220> FEATURE:
<223> OTHER INFORMATION: Primer

<400> SEQUENCE: 30
atgtcgactc acttgatggt tccagca                                       27

<210> SEQ ID NO 31
<211> LENGTH: 3034
<212> TYPE: DNA
<213> ORGANISM: Artificial Sequence
<220> FEATURE:
<223> OTHER INFORMATION: Sequence of 3034 bp Asp 718  fragment
      containing 35S-CreN-IntN-3'ocs gene in plasmid pGV947
```

<400> SEQUENCE: 31

```
ggtacccgat ccaattccaa tcccacaaaa atctgagctt aacagcacag ttgctcctct      60
cagagcagaa tcgggtattc aacaccctca tatcaactac tacgttgtgt ataacggtcc     120
acatgccggt atatacgatg actggggttg tacaaaggcg gcaacaaacg gcgttcccgg     180
agttgcacac aagaaatttg ccactattac agaggcaaga gcagcagctg acgcgtacac     240
aacaagtcag caaacagaca ggttgaactt catccccaaa ggagaagctc aactcaagcc     300
caagagcttt gctaaggccc taacaagccc accaaagcaa aaagcccact ggctcacgct     360
aggaaccaaa aggcccagca gtgatccagc cccaaaagag atctcctttg ccccggagat     420
tacaatggac gatttcctct atctttacga tctaggaagg aagttcgaag gtgaaggtga     480
cgacactatg ttcaccactg ataatgagaa ggttagcctc ttcaatttca gaaagaatgc     540
tgacccacag atggttagag aggcctacgc agcaggtctc atcaagacga tctacccgag     600
taacaatctc caggagatca ataccttcc caagaaggtt aaagatgcag tcaaaagatt      660
caggactaat tgcatcaaga acacagaaa agacatattt ctcaagatca gaagtactat      720
tccagtatgg acgattcaag gcttgcttca taaaccaagg caagtaatag agattggagt     780
ctctaaaaag gtagttccta ctgaatctaa ggccatgcat ggagtctaag attcaaatcg     840
aggatctaac agaactcgcc gtgaagactg gcgaacagtt catacagagt cttttacgac     900
tcaatgacaa gaagaaaatc ttcgtcaaca tggtggagca cgacactctg gtctactcca     960
aaaatgtcaa agatacagtc tcagaagacc aaagggctat tgagactttt caacaaagga    1020
taatttcggg aaacctcctc ggattccatt gcccagctat ctgtcacttc atcgaaagga    1080
cagtagaaaa ggaaggtggc tcctacaaat gccatcattg cgataaagga aaggctatca    1140
ttcaagatgc ctctgccgac agtggtccca agatggacc cccacccacg aggagcatcg    1200
tggaaaaaga agacgttcca accacgtctt caaagcaagt ggattgatgt gacatctcca    1260
ctgacgtaag ggatgacgca caatcccact atccttcgca agacccttcc tctatataag    1320
gaagttcatt tcatttggag aggacacgct cgagctcatt tctctattac ttcagccata    1380
acaaaagaac tcttttctct tcttattaaa ccatggccaa tttactgacc gtacaccaaa    1440
atttgcctgc attaccggtc gatgcaacga gtgatgaggt tcgcaagaac ctgatggaca    1500
tgttcaggga tcgccaggcg ttttctgagc atacctggaa aatgcttctg tccgtttgcc    1560
ggtcgtgggc ggcatggtgc aagttgaata accggaaatg gtttcccgca gaacctgaag    1620
atgttcgcga ttatcttcta tatcttcagg cgcgcggtct ggcagtaaaa actatccagc    1680
aacatttggg ccagctaaac atgcttcatc gtcggtccgg gctgccacga ccaagtgaca    1740
gcaatgctgt ttcactagtt atgcggcgga tccgaaaaga aaacgttgat gccggtgaac    1800
gtgcaaaaca ggctctagcg ttcgaacgca ctgatttcga ccaggttcgt tcactcatgg    1860
aaaatagcga tcgctgctgc ctttctttcg gaactgagat ccttaccgtt gagtacggac    1920
cacttcctat tggtaagatc gtttctgagg aaattaactg ctcagtgtac tctgttgatc    1980
cagaaggaag agtttacact caggctatcg cacaatggca cgatagggt gaacaagagg    2040
ttctcgagta cgagcttgaa gatggatccg ttattcgtgc tacctctgac catagattct    2100
tgactacaga ttatcagctt ctcgctatcg aggaaatctt tgctaggcaa cttgatctcc    2160
ttactttgga gaacatcaag cagacagaag aggctcttga caaccacaga cttccattcc    2220
ctttgctcga tgctggaacc atcaagtgag tcgacataat cactagagtc ctgctttaat    2280
```

-continued

```
gagatatgcg agacgcctat gatcgcatga tatttgctttt caattctgtt gtgcacgttg    2340
taaaaaacct gagcatgtgt agctcagatc cttaccgccg gtttcggttc attctaatga    2400
atatatcacc cgttactatc gtatttttat gaataatatt ctccgttcaa tttactgatt    2460
gtaccctact acttatatgt acaatattaa aatgaaaaca atatattgtg ctgaataggt    2520
ttatagcgac atctatgata gagcgccaca ataacaaaca attgcgtttt attattacaa    2580
atccaatttt aaaaaagcg gcagaaccgg tcaaacctaa aagactgatt acataaatct    2640
tattcaaatt tcaaaaggcc ccaggggcta gtatctacga cacaccgagc ggcgaactaa    2700
taacgttcac tgaagggaac tccggttccc cgccggcgcg catgggtgag attccttgaa    2760
gttgagtatt ggccgtccgc tctaccgaaa gttacgggca ccattcaacc cggtccagca    2820
cggcggccgg gtaaccgact tgctgccccg agaattatgc agcatttttt tggtgtatgt    2880 gggcccccaaa tgaagtgcag gtcaaacctt gacagtgacg acaaatcgtt gggcgggtcc    2940
agggcgaatt ttgcgacaac atgtcgaggc tcagcaggac ctgcaggcat gcaagcttat    3000
cgataccgtc gacctcgagg gggggcccgg tacc                                 3034
```

<210> SEQ ID NO 32
<211> LENGTH: 17
<212> TYPE: DNA
<213> ORGANISM: Artificial Sequence
<220> FEATURE:
<223> OTHER INFORMATION: 17 bp linker sequence

<400> SEQUENCE: 32

```
gtcgacataa tcactag                                                     17
```

<210> SEQ ID NO 33
<211> LENGTH: 60
<212> TYPE: DNA
<213> ORGANISM: Artificial Sequence
<220> FEATURE:
<223> OTHER INFORMATION: 60 bp polylinker

<400> SEQUENCE: 33

```
caggacctgc aggcatgcaa gcttatcgat accgtcgacc tcgagggggg gcccggtacc    60
```

<210> SEQ ID NO 34
<211> LENGTH: 27
<212> TYPE: DNA
<213> ORGANISM: Artificial Sequence
<220> FEATURE:
<223> OTHER INFORMATION: Primer

<400> SEQUENCE: 34

```
gaccatggtt aaggtgattg gaagacg                                          27
```

<210> SEQ ID NO 35
<211> LENGTH: 30
<212> TYPE: DNA
<213> ORGANISM: Artificial Sequence
<220> FEATURE:
<223> OTHER INFORMATION: Primer

<400> SEQUENCE: 35

```
tacgtatatc ctggcaattg gcagcgatgg                                       30
```

<210> SEQ ID NO 36
<211> LENGTH: 31
<212> TYPE: DNA
<213> ORGANISM: Artificial Sequence

```
<220> FEATURE:
<223> OTHER INFORMATION: Primer

<400> SEQUENCE: 36
cgctgccaat tgccaggata tacgtaatct g                                        31

<210> SEQ ID NO 37
<211> LENGTH: 28
<212> TYPE: DNA
<213> ORGANISM: Artificial Sequence
<220> FEATURE:
<223> OTHER INFORMATION: Primer

<400> SEQUENCE: 37
agtcgaccta atcgccatct tccagcag                                            28

<210> SEQ ID NO 38
<211> LENGTH: 2873
<212> TYPE: DNA
<213> ORGANISM: Artificial Sequence
<220> FEATURE:
<223> OTHER INFORMATION: Sequence of 2873 bp Asp 718 bp fragment
      containing 35S:IntC-CreC:3'ocs in plasmid pGV951

<400> SEQUENCE: 38
ggtacccgat ccaattccaa tcccacaaaa atctgagctt aacagcacag ttgctcctct       60
cagagcagaa tcgggtattc aacaccctca tatcaactac tacgttgtgt ataacggtcc      120
acatgccggt atatacgatg actggggttg tacaaaggcg gcaacaaacg gcgttcccgg      180
agttgcacac aagaaatttg ccactattac agaggcaaga gcagcagctg acgcgtacac      240
aacaagtcag caaacagaca ggttgaactt catccccaaa ggagaagctc aactcaagcc      300
caagagcttt gctaaggccc taacaagccc accaaagcaa aaagcccact ggctcacgct      360
aggaaccaaa aggcccagca gtgatccagc cccaaaagag atctcctttg ccccggagat      420
tacaatggac gatttcctct atctttacga tctaggaagg aagttcgaag gtgaaggtga      480
cgacactatg ttcaccactg ataatgagaa ggttagcctc ttcaatttca gaaagaatgc      540
tgacccacag atggttagag aggcctacgc agcaggtctc atcaagacga tctacccgag      600
taacaatctc caggagatca aataccttcc caagaaggtt aaagatgcag tcaaaagatt      660
caggactaat tgcatcaaga acacagaaa agacatattt ctcaagatca gaagtactat      720
tccagtatgg acgattcaag gcttgcttca taaaccaagg caagtaatag agattggagt      780
ctctaaaaag gtagttccta ctgaatctaa ggccatgcat ggagtctaag attcaaatcg      840
aggatctaac agaactcgcc gtgaagactg gcgaacagtt catacagagt cttttacgac      900
tcaatgacaa gaagaaaatc ttcgtcaaca tggtggagca cgacactctg gtctactcca      960
aaaatgtcaa agatacagtc tcagaagacc aaagggctat tgagactttt caacaaagga     1020
taatttcggg aaacctcctc ggattccatt gcccagctat ctgtcacttc atcgaaagga     1080
cagtagaaaa ggaaggtggc tcctacaaat gccatcattg cgataaagga aaggctatca     1140
ttcaagatgc ctctgccgac agtggtccca agatggaccc ccacccacg aggagcatcg     1200 tggaaaaaga agacgttcca accacgtctt caaagcaagt ggattgatgt gacatctcca     1260
ctgacgtaag ggatgacgca caatcccact atccttcgca agacccttcc tctatataag     1320
gaagttcatt tcatttggag aggacacgct cgagctcatt tctctattac ttcagccata     1380
acaaaagaac tcttttctct tcttattaaa ccatggttaa ggtgattgga agacgttctc     1440
ttggtgttca aaggatcttc gatatcggat tgccacaaga ccacaacttt cttctcgcta     1500
```

-continued

```
atggtgccat cgctgccaat tgccaggata tacgtaatct ggcatttctg gggattgctt      1560
ataacaccct gttacgtata gccgaaattg ccaggatcag ggttaaagat atctcacgta      1620
ctgacggtgg gagaatgtta atccatattg gcagaacgaa aacgctggtt agcaccgcag      1680
gtgtagagaa ggcacttagc ctgggggtaa ctaaactggt cgagcgatgg atttccgtct      1740
ctggtgtagc tgatgatccg aataactacc tgttttgccg ggtcagaaaa aatggtgttg      1800
ccgcgccatc tgccaccagc cagctatcaa ctcgcgccct ggaagggatt tttgaagcaa      1860
ctcatcgatt gatttacggc gctaaggatg actctggtca gagatacctg cctggtctg      1920 gacacagtgc ccgtgtcgga gccgcgcgag atatggcccg cgctggagtt tcaataccgg      1980
agatcatgca agctggtggc tggaccaatg taaatattgt catgaactat atccgtaacc      2040
tggatagtga aacaggggca atggtgcgcc tgctggaaga tggcgattag gtcgactatc      2100
actagagtcc tgctttaatg agatatgcga gacgcctatg atcgcatgat atttgctttc      2160
aattctgttg tgcacgttgt aaaaaacctg agcatgtgta gctcagatcc ttaccgccgg      2220
tttcggttca ttctaatgaa tatatcaccc gttactatcg tattttatg aataatattc      2280 tccgttcaat ttactgattg taccctacta cttatatgta caatattaaa atgaaaacaa      2340
tatattgtgc tgaataggtt tatagcgaca tctatgatag agcgccacaa taacaaacaa      2400
ttgcgtttta ttattacaaa tccaattta aaaaaagcgg cagaaccggt caaacctaaa       2460
agactgatta cataaatctt attcaaattt caaaaggccc caggggctag tatctacgac      2520
acaccgagcg gcgaactaat aacgttcact gaagggaact ccggttcccc gccggcgcgc      2580
atgggtgaga ttccttgaag ttgagtattg gccgtccgct ctaccgaaag ttacgggcac      2640
cattcaaccc ggtccagcac ggcggccggg taaccgactt gctgccccga gaattatgca      2700 gcatttttt ggtgtatgtg ggccccaaat gaagtgcagg tcaaaccttg acagtgacga      2760
caaatcgttg ggcgggtcca gggcgaattt tgcgacaaca tgtcgaggct cagcaggacc      2820
tgcaggcatg caagcttatc gataccgtcg acctcgaggg ggggcccggt acc            2873
```

<210> SEQ ID NO 39
<211> LENGTH: 15
<212> TYPE: DNA
<213> ORGANISM: Artificial Sequence
<220> FEATURE:
<223> OTHER INFORMATION: 15 bp linker

<400> SEQUENCE: 39

```
gtcgactatc actag                                                        15
```

<210> SEQ ID NO 40
<211> LENGTH: 5449
<212> TYPE: DNA
<213> ORGANISM: Artificial Sequence
<220> FEATURE:
<223> OTHER INFORMATION: Sequence of 5449 bp Sal I-Hind III fragment
      containing the blocked GUS reporter gene for Cre-Lox excision in
      plasmid pGV801

<400> SEQUENCE: 40

```
gtcgactcta gaggatccaa ttccaatccc acaaaaatct gagcttaaca gcacagttgc        60
tcctctcaga gcagaatcgg gtattcaaca ccctcatatc aactactacg ttgtgtataa       120
cggtccacat gccggtatat acgatgactg gggttgtaca aaggcggcaa caaacggcgt       180
tcccggagtt gcacacaaga aatttgccac tattacagag gcaagagcag cagctgacgc       240
```

```
gtacacaaca agtcagcaaa cagacaggtt gaacttcatc cccaaaggag aagctcaact    300
caagcccaag agctttgcta aggccctaac aagcccacca aagcaaaaag cccactggct    360
cacgctagga accaaaaggc ccagcagtga tccagcccca aaagagatct cctttgcccc    420
ggagattaca atggacgatt tcctctatct ttacgatcta ggaaggaagt tcgaaggtga    480
aggtgacgac actatgttca ccactgataa tgagaaggtt agcctcttca atttcagaaa    540
gaatgctgac ccacagatgg ttagagaggc ctacgcagca ggtctcatca agacgatcta    600
cccgagtaac aatctccagg agatcaaata ccttcccaag aaggttaaag atgcagtcaa    660
aagattcagg actaattgca tcaagaacac agagaaagac atatttctca agatcagaag    720
tactattcca gtatggacga ttcaaggctt gcttcataaa ccaaggcaag taatagagat    780
tggagtctct aaaaggtag ttcctactga atctaaggcc atgcatggag tctaagattc    840
aaatcgagga tctaacagaa ctcgccgtga agactggcga acagttcata cagagtcttt    900
tacgactcaa tgcaagaag aaaatcttcg tcaacatggt ggagcacgac actctggtct    960
actccaaaaa tgtcaaagat acagtctcag aagaccaaag ggctattgag acttttcaac   1020
aaaggataat ttcgggaaac ctcctcggat tccattgccc agctatctgt cacttcatcg   1080
aaaggacagt agaaaaggaa ggtggctcct acaaatgcca tcattgcgat aaaggaaagg   1140
ctatcattca agatgcctct gccgacagtg gtcccaaaga tggaccccca cccacgagga   1200
gcatcgtgga aaagaagac gttccaacca cgtcttcaaa gcaagtggat tgatgtgaca   1260
tctccactga cgtaagggat gacgcacaat cccactatcc ttcgcaagac ccttcctcta   1320
tataaggaag ttcatttcat tggagagga cacgctcgag ctcatttctc tattacttca   1380
gccataacaa aagaactctt ttctcttctt attaaaccat gataacttcg tatagcatac   1440
attatacgaa gttatcctag gatcatgagc ggagaattaa gggagtcacg ttatgacccc   1500
cgccgatgac gcgggacaag ccgttttacg tttggaactg acagaaccgc aacgttgaag   1560
gagccactca gccgcgggtt tctggagttt aatgagctaa gcacatacgt cagaaaccat   1620
tattgcgcgt tcaaaagtcg cctaaggtca ctatcagcta gcaaatattt cttgtcaaaa   1680
atgctccact gacgttccat aaattcccct cggtatccaa ttagagtctc atattcactc   1740
tcaatccaaa taatctgcac cggatctgga tcgtttcgca tgattgaaca agatggattg   1800
cacgcaggtt ctccggccgc ttgggtggag aggctattcg gctatgactg ggcacaacag   1860
acaatcggct gctctgatgc cgccgtgttc cggctgtcag cgcaggggcg cccggttctt   1920
tttgtcaaga ccgacctgtc cggtgccctg aatgaactgc aggacgaggc agcgcggcta   1980
tcgtggctgg ccacgacggg cgttccttgc gcagctgtgc tcgacgttgt cactgaagcg   2040
ggaagggact ggctgctatt gggcgaagtg ccggggcagg atctcctgtc atctcacctt   2100
gctcctgccg agaaagtatc catcatggct gatgcaatgc ggcggctgca tacgcttgat   2160
ccggctacct gcccattcga ccaccaagcg aaacatcgca tcgagcgagc acgtactcgg   2220
atggaagccg gtcttgtcga tcaggatgat ctggacgaag agcatcaggg gctcgcgcca   2280
gccgaactgt tcgccaggct caaggcgcgc atgcccgacg gcgatgatct cgtcgtgacc   2340
catggcgatg cctgcttgcc gaatatcatg gtggaaaatg gccgcttttc tggattcatc   2400
gactgtggcc ggctgggtgt ggcggaccgc tatcaggaca tagcgttggc tacccgtgat   2460
attgctgaag agcttggcgg cgaatgggct gaccgcttcc tcgtgcttta cggtatcgcc   2520
gctcccgatt cgcagcgcat cgccttctat cgccttcttg acgagttctt ctgagcggga   2580
ctctggggtt cgaaatgacc gaccaagcga cgcccaacct gccatcacga gatttcgatt   2640
```

```
ccaccgccgc cttctatgaa aggttgggct tcggaatcgt tttccgggac gccggctgga   2700
tgatcctcca gcgcggggat ctcatgctgg agttcttcgc ccacgggatc tctgcggaac   2760
aggcggtcga aggtgccgat atcattacga cagcaacggc cgacaagcac aacgccacga   2820
tcctgagcga caatatgatc gggcccggcg tccacatcaa cggcgtcggc ggcgactgcc   2880
caggcaagac cgagatgcac cgcgatatct tgctgcgttc ggatattttc gtggagttcc   2940
cgccacagac ccggatgatc cccgatcgtt caaacatttg gcaataaagt ttcttaagat   3000
tgaatcctgt tgccggtctt gcgatgatta tcatataatt tctgttgaat tacgttaagc   3060
atgtaataat taacatgtaa tgcatgacgt tatttatgag atgggttttt atgattagag   3120
tcccgcaatt atacatttaa tacgcgatag aaaacaaaat atagcgcgca aactaggata   3180
aattatcgcg cgcggtgtca tctatgttac tagatcgggc ctcctgtcaa tgctggccta   3240
ggtaaataac ttcgtatagc atacattata cgaagttatt agtacgtcct gtagaaaccc   3300
caacccgtga aatcaaaaaa ctcgacggcc tgtgggcatt cagtctggat cgcgaaaact   3360
gtggaattga tcagcgttgg tgggaaagcg cgttacaaga aagccgggca attgctgtgc   3420
caggcagttt taacgatcag ttcgccgatg cagatattcg taattatgcg ggcaacgtct   3480
ggtatcagcg cgaagtcttt ataccgaaag gttgggcagg ccagcgtatc gtgctgcgtt   3540
tcgatgcggt cactcattac ggcaaagtgt gggtcaataa tcaggaagtg atggagcatc   3600
agggcggcta tacgccattt gaagccgatg tcacgccgta tgttattgcc gggaaaagtg   3660
tacgtatcac cgtttgtgtg aacaacgaac tgaactggca gactatcccg ccgggaatgg   3720
tgattaccga cgaaaacggc aagaaaaagc agtcttactt ccatgatttc tttaactatg   3780
ccggaatcca tcgcagcgta atgctctaca ccacgccgaa cacctgggtg acgatatca   3840
ccgtggtgac gcatgtcgcg caagactgta accacgcgtc tgttgactgg caggtggtgg   3900
ccaatggtga tgtcagcgtt gaactgcgtg atgcggatca acaggtggtt gcaactggac   3960
aaggcactag cgggactttg caagtggtga atccgcacct ctggcaaccg ggtgaaggtt   4020
atctctatga actgtgcgtc acagccaaaa gccagacaga gtgtgatatc tacccgcttc   4080
gcgtcggcat ccggtcagtg gcagtgaagg ccaacagtt cctgattaac cacaaaccgt   4140
tctactttac tggctttggt cgtcatgaag atgcggactt acgtggcaaa ggattcgata   4200
acgtgctgat ggtgcacgac cacgcattaa tggactggat tggggccaac tcctaccgta   4260
cctcgcatta cccttacgct gaagagatgc tcgactgggc agatgaacat ggcatcgtgg   4320
tgattgatga aactgctgct gtcggcttta acctctcttt aggcattggt ttcgaagcgg   4380
gcaacaagcc gaaagaactg tacagcgaag aggcagtcaa cggggaaact cagcaagcgc   4440
acttacaggc gattaaagag ctgatagcgc gtgacaaaaa ccacccaagc gtggtgatgt   4500
ggagtattgc caacgaaccg gatacccgtc cgcaagtgca cgggaatatt tcgccactgg   4560
cggaagcaac gcgtaaactc gacccgacgc gtccgatcac ctgcgtcaat gtaatgttct   4620
gcgacgctca caccgatacc atcagcgatc tctttgatgt gctgtgcctg aaccgttatt   4680
acggatggta tgtccaaagc ggcgatttgg aaacggcaga aaggtactg gaaaaagaac   4740
ttctggcctg gcaggagaaa ctgcatcagc cgattatcat caccgaatac ggcgtggata   4800
cgttagccgg gctgcactca atgtacaccg acatgtggag tgaagagtat cagtgtgcat   4860
ggctggatat gtatcaccgc gtctttgatc gcgtcagcgc cgtcgtcggt gaacaggtat   4920
ggaatttcgc cgattttgcg acctcgcaag gcatattgcg cgttggcggt aacaagaaag   4980
```

```
ggatcttcac tcgcgaccgc aaaccgaagt cggcggcttt tctgctgcaa aaacgctgga      5040
ctggcatgaa cttcggtgaa aaaccgcagc agggaggcaa acaatgaatc aacaactctc      5100
ctggcgcacc atcgtcggct acagcctcgg tggggaattc cccggggta cctaaagaag       5160 gagtgcgtcg aagcagatcg ttcaaacatt tggcaataaa gtttcttaag attgaatcct     5220
gttgccggtc ttgcgatgat tatcatataa tttctgttga attacgttaa gcatgtaata     5280
attaacatgt aatgcatgac gttatttatg agatgggttt ttatgattag agtcccgcaa     5340
ttatacattt aatacgcgat agaaaacaaa atatagcgcg caaactagga taaattatcg     5400
cgcgcggtgt catctatgtt actagatcga tgtcgactct agaaagctt                 5449
```

```
<210> SEQ ID NO 41
<211> LENGTH: 24
<212> TYPE: DNA
<213> ORGANISM: Artificial Sequence
<220> FEATURE:
<223> OTHER INFORMATION: 24 bp polylinker

<400> SEQUENCE: 41
gtcgactcta gaggatccaa ttcc                                              24

<210> SEQ ID NO 42
<211> LENGTH: 34
<212> TYPE: DNA
<213> ORGANISM: Artificial Sequence
<220> FEATURE:
<223> OTHER INFORMATION: Lox P sequence

<400> SEQUENCE: 42
ataacttcgt atagcataca ttatacgaag ttat                                   34

<210> SEQ ID NO 43
<211> LENGTH: 22
<212> TYPE: DNA
<213> ORGANISM: Artificial Sequence
<220> FEATURE:
<223> OTHER INFORMATION: 22 bp polylinker

<400> SEQUENCE: 43
tggggaattc cccgggggta cc                                                22

<210> SEQ ID NO 44
<211> LENGTH: 18
<212> TYPE: DNA
<213> ORGANISM: Artificial Sequence
<220> FEATURE:
<223> OTHER INFORMATION: 18 bp polylinker

<400> SEQUENCE: 44
gtcgactcta gaaagctt                                                     18

<210> SEQ ID NO 45
<211> LENGTH: 2189
<212> TYPE: DNA
<213> ORGANISM: Artificial Sequence
<220> FEATURE:
<223> OTHER INFORMATION: Sequence of 2189 bp Bgl II-Hind III fragment
      containing SCP:Flp:3'pin gene in plasmid pPH12891

<400> SEQUENCE: 45
agatctgagc ttctagagat ccgtcaacat ggtggagcac gacactctcg tctactccaa      60
gaatatcaaa gatacagtct cagaagacca aagggctatt gagactttc aacaaagggt       120
```

-continued

```
aatatcggga aacctcctcg gattccattg cccagctatc tgtcacttca tcaaaaggac      180
agtagaaaag gaaggtggca cctacaaatg ccatcattgc gataaaggaa aggctatcgt      240
tcaagatgcc tctgccgaca gtggtcccaa agatggaccc ccacccacga ggagcatcgt      300
ggaaaaagaa gacgttccaa ccacgtcttc aaagcaagtg gattgatgtg atgatcctat      360
gcgtatggta tgacgtgtgt tcaagatgat gacttcaaac ctacctatga cgtatggtat      420
gacgtgtgtc gactgatgac ttagatccac tcgagcggct ataaatacgt acctacgcac      480
cctgcgctac catccctaga gctgcagctt attttttacaa caattaccaa caacaacaaa      540
caacaaacaa cattacaatt actatttaca attacagtcg acccgggatc caacaatgcc      600
ccagttcgac atcctctgca agaccccccc caaggtgctc gtgaggcagt tcgtggagag      660
gttcgagagg ccctccggcg agaagatcgc cctctgcgcc gccgagctca cctacctctg      720
ctggatgatc acccacaacg gcaccgccat taagagggcc accttcatgt catacaacac      780
catcatctcc aactccctct ccttcgacat cgtgaacaag tccctccagt tcaaatacaa      840
gacccagaag gccaccatcc tcgaggcctc cctcaagaag ctcatccccg cctgggagtt      900
caccatcatc ccctactacg gccagaagca ccagtccgac atcaccgaca tcgtgtcatc      960
cctccagctt cagttcgagt cctccgagga ggctgacaag ggcaactccc actccaagaa     1020
gatgctgaag gccctcctct ccgagggcga gtccatctgg gagatcaccg agaagatcct     1080
caactccttc gagtacacct ccaggttcac taagaccaag accctctacc agttcctctt     1140
cctcgccacc ttcatcaact gcggcaggtt ctcagacatc aagaacgtgg accccaagtc     1200
cttcaagctc gtgcagaaca agtacctcgg cgtgatcatc cagtgcctcg tgaccgagac     1260
caagacctcc gtgtccaggc acatctactt ctttctccgct cgcggcagga tcgacccccct     1320 cgtgtacctc gacgagttcc tcaggaactc agagcccgtg ctcaagaggg tgaacaggac     1380
cggcaactcc tcctccaaca agcaggagta ccagctcctc aaggacaacc tcgtgaggtc     1440
ctacaacaag gccctcaaga gaacgccccc ctactccatc ttcgccatca gaacggccc      1500 caagtcccac atcggtaggc acctcatgac ctccttcctc tcaatgaagg gcctcaccga     1560
gctcaccaac gtggtgggca actggtccga caagagggcc tccgccgtgg ccaggaccac     1620
ctacacccac cagatcaccg ccatccccga ccactacttc gccctcgtgt caaggtacta     1680
cgcctacgac cccatctcca aggagatgat cgccctcaag gacgagacta accccatcga     1740
ggagtggcag cacatcgagc agctcaaggg ctccgccgag gctccatcca ggtaccccgc     1800
ctggaacggc atcatctccc aggaggtgct cgactacctc tcctcctaca tcaacaggag     1860
gatctgagtt aacctagact tgtccatctt ctggattggc caacttaatt aatgtatgaa     1920
ataaaaggat gcacacatag tgacatgcta atcactataa tgtgggcatc aaagttgtgt     1980
gttatgtgta attactagtt atctgaataa aagagaaaga gatcatccat atttcttatc     2040
ctaaatgaat gtcacgtgtc tttataattc tttgatgaac cagatgcatt tcattaacca     2100
aatccatata catataaata ttaatcatat ataattaata tcaattgggt tagcaaaaca     2160
aatctagtct aggtgtgttt tgcgaattc                                        2189
```

<210> SEQ ID NO 46
<211> LENGTH: 21
<212> TYPE: DNA
<213> ORGANISM: Artificial Sequence
<220> FEATURE:
<223> OTHER INFORMATION: 21 bp polylinker

<400> SEQUENCE: 46
agatctgagc ttctagagat c                                              21

<210> SEQ ID NO 47
<211> LENGTH: 76
<212> TYPE: DNA
<213> ORGANISM: Artificial Sequence
<220> FEATURE:
<223> OTHER INFORMATION: 76 bp including 5'UTR

<400> SEQUENCE: 47
acaattacca acaacaacaa acaacaaaca acattacaat tactatttac aattacagtc   60
gacccgggat ccaaca                                                    76

<210> SEQ ID NO 48
<211> LENGTH: 25
<212> TYPE: DNA
<213> ORGANISM: Artificial Sequence
<220> FEATURE:
<223> OTHER INFORMATION: Primer

<400> SEQUENCE: 48
ttacagtcga cccgggatcc aacaa                                          25

<210> SEQ ID NO 49
<211> LENGTH: 28
<212> TYPE: DNA
<213> ORGANISM: Artificial Sequence
<220> FEATURE:
<223> OTHER INFORMATION: Primer

<400> SEQUENCE: 49
cgaaagaaag gcagcagttg atgaaggt                                       28

<210> SEQ ID NO 50
<211> LENGTH: 29
<212> TYPE: DNA
<213> ORGANISM: Artificial Sequence
<220> FEATURE:
<223> OTHER INFORMATION: Primer

<400> SEQUENCE: 50
ccttcatcaa ctgctgcctt tctttcgga                                      29

<210> SEQ ID NO 51
<211> LENGTH: 28
<212> TYPE: DNA
<213> ORGANISM: Artificial Sequence
<220> FEATURE:
<223> OTHER INFORMATION: Primer

<400> SEQUENCE: 51
cggggtacct cacttgatgg ttccagca                                       28

<210> SEQ ID NO 52
<211> LENGTH: 1933
<212> TYPE: DNA
<213> ORGANISM: Artificial Sequence
<220> FEATURE:
<223> OTHER INFORMATION: Sequence of 1933 bp Bgl II-Eco RI fragment
      containing SCP:FlpN-IntN:3'pin gene in plasmid pSCP:FlpN-IntN:3'
      pin

<400> SEQUENCE: 52
agatctgagc ttctagagat ccgtcaacat ggtggagcac gacactctcg tctactccaa   60

```
gaatatcaaa gatacagtct cagaagacca aagggctatt gagactttc aacaaagggt      120 aatatcggga aacctcctcg gattccattg cccagctatc tgtcacttca tcaaaaggac      180
agtagaaaag gaaggtggca cctacaaatg ccatcattgc gataaaggaa aggctatcgt      240
tcaagatgcc tctgccgaca gtggtcccaa agatggaccc ccacccacga ggagcatcgt      300
ggaaaaagaa gacgttccaa ccacgtcttc aaagcaagtg gattgatgtg atgatcctat      360
gcgtatggta tgacgtgtgt tcaagatgat gacttcaaac ctacctatga cgtatggtat      420
gacgtgtgtc gactgatgac ttagatccac tcgagcggct ataaatacgt acctacgcac      480
cctgcgctac catccctaga gctgcagctt attttttacaa caattaccaa caacaacaaa      540
caacaaacaa cattacaatt actatttaca attacagtcg acccgggatc caacaatgcc      600
ccagttcgac atcctctgca agaccccccc caaggtgctc gtgaggcagt tcgtggagag      660
gttcgagagg ccctccggcg agaagatcgc cctctgcgcc gccgagctca cctacctctg      720
ctggatgatc acccacaacg caccgccat taagagggcc accttcatgt catacaacac      780
catcatctcc aactccctct ccttcgacat cgtgaacaag tccctccagt tcaaatacaa      840
gacccagaag gccaccatcc tcgaggcctc cctcaagaag ctcatccccg cctgggagtt      900
caccatcatc ccctactacg gccagaagca ccagtccgac atcaccgaca tcgtgtcatc      960
cctccagctt cagttcgagt cctccgagga ggctgacaag ggcaactccc actccaagaa     1020
gatgctgaag gccctcctct ccgagggcga gtccatctgg gagatcaccg agaagatcct     1080
caactccttc gagtacacct ccaggttcac taagaccaag accctctacc agttcctctt     1140
cctcgccacc ttcatcaact gctgcctttc tttcggaact gagatcctta ccgttgagta     1200
cggaccactt cctattggta agatcgtttc tgaggaaatt aactgctcag tgtactctgt     1260
tgatccagaa ggaagagttt acactcaggc tatcgcacaa tggcacgata ggggtgaaca     1320
agaggttctc gagtacgagc ttgaagatgg atccgttatt cgtgctacct ctgaccatag     1380
attcttgact acagattatc agcttctcgc tatcgaggaa atctttgcta ggcaacttga     1440
tctccttact ttggagaaca tcaagcagac agaagaggct cttgacaacc acagacttcc     1500 attcccttg ctcgatgctg gaaccatcaa gtgaggtacc ccgcctggaa cggcatcatc     1560
tcccaggagg tgctcgacta cctctcctcc tacatcaaca ggaggatctg agttaaccta     1620
gacttgtcca tcttctggat tggccaactt aattaatgta tgaaataaaa ggatgcacac     1680
atagtgacat gctaatcact ataatgtggg catcaaagtt gtgtgttatg tgtaattact     1740
agttatctga ataaaagaga aagagatcat ccatatttct tatcctaaat gaatgtcacg     1800
tgtctttata attctttgat gaaccagatg catttcatta accaaatcca tatacatata     1860
aatattaatc atatataatt aatatcaatt gggttagcaa aacaaatcta gtctaggtgt     1920
gttttgcgaa ttc                                                        1933
```

<210> SEQ ID NO 53
<211> LENGTH: 27
<212> TYPE: DNA
<213> ORGANISM: Artificial Sequence
<220> FEATURE:
<223> OTHER INFORMATION: Primer

<400> SEQUENCE: 53
gaatctaagg ccatgcatgg agtctaa                                          27

<210> SEQ ID NO 54
<211> LENGTH: 30

<210> SEQ ID NO 54
<211> LENGTH: 30 (implied)
<212> TYPE: DNA
<213> ORGANISM: Artificial Sequence
<220> FEATURE:
<223> OTHER INFORMATION: Primer

<400> SEQUENCE: 54
ctgagaacct gccgcaattg gcagcgatgg        30

<210> SEQ ID NO 55
<211> LENGTH: 31
<212> TYPE: DNA
<213> ORGANISM: Artificial Sequence
<220> FEATURE:
<223> OTHER INFORMATION: Primer

<400> SEQUENCE: 55
cgctgccaat tgcggcaggt tctcagacat c        31

<210> SEQ ID NO 56
<211> LENGTH: 29
<212> TYPE: DNA
<213> ORGANISM: Artificial Sequence
<220> FEATURE:
<223> OTHER INFORMATION: Primer

<400> SEQUENCE: 56
ggactctaga ctcagatcct cctgttgat        29

<210> SEQ ID NO 57
<211> LENGTH: 3002
<212> TYPE: DNA
<213> ORGANISM: Artificial Sequence
<220> FEATURE:
<223> OTHER INFORMATION: Sequence of 3002 bp Asp 718 fragment containing
     35S:IntC-FlpC:3'ocs gene in plasmid p35S:IntC-FlpC:3'ocs

<400> SEQUENCE: 57
ggtacccgat ccaattccaa tcccacaaaa atctgagctt aacagcacag ttgctcctct        60
cagagcagaa tcgggtattc aacaccctca tatcaactac tacgttgtgt ataacggtcc       120
acatgccggt atatacgatg actggggttg tacaaaggcg gcaacaaacg gcgttcccgg       180
agttgcacac aagaaatttg ccactattac agaggcaaga gcagcagctg acgcgtacac       240
aacaagtcag caaacagaca ggttgaactt catccccaaa ggagaagctc aactcaagcc       300
caagagcttt gctaaggccc taacaagccc accaaagcaa aaagcccact ggctcacgct       360
aggaaccaaa aggcccagca gtgatccagc cccaaaagag atctcctttg ccccggagat       420
tacaatggac gatttcctct atctttacga tctaggaagg aagttcgaag gtgaaggtga       480
cgacactatg ttcaccactg ataatgagaa ggttagcctc ttcaatttca gaaagaatgc       540
tgacccacag atggttagag aggcctacgc agcaggtctc atcaagacga tctacccgag       600
taacaatctc caggagatca aataccttcc caagaaggtt aaagatgcag tcaaaagatt       660
caggactaat tgcatcaaga acacagagaa agacatattt ctcaagatca gaagtactat       720
tccagtatgg acgattcaag gcttgcttca taaaccaagg caagtaatag agattggagt       780
ctctaaaaag gtagttccta ctgaatctaa ggccatgcat ggagtctaag attcaaatcg       840
aggatctaac agaactcgcc gtgaagactg gcgaacagtt catacagagt cttttacgac       900
tcaatgacaa gaagaaaatc ttcgtcaaca tggtggagca cgacactctg gtctactcca       960
aaaatgtcaa agatacagtc tcagaagacc aagggctatg agactttt caacaaagga      1020
taatttcggg aaacctcctc ggattccatt gcccagctat ctgtcacttc atcgaaagga      1080

-continued

```
cagtagaaaa ggaaggtggc tcctacaaat gccatcattg cgataaagga aaggctatca    1140
ttcaagatgc ctctgccgac agtggtccca agatggacc cccacccacg aggagcatcg     1200
tggaaaaaga agacgttcca accacgtctt caaagcaagt ggattgatgt gacatctcca    1260
ctgacgtaag ggatgacgca caatcccact atccttcgca agacccttcc tctatataag    1320
gaagttcatt tcatttggag aggacacgct cgagctcatt tctctattac ttcagccata    1380
acaaaagaac tcttttctct tcttattaaa ccatggttaa ggtgattgga agacgttctc    1440
ttggtgttca aaggatcttc gatatcggat tgccacaaga ccacaacttt cttctcgcta    1500
atggtgccat cgctgccaat tgcggcaggt tctcagacat caagaacgtg gaccccaagt    1560
ccttcaagct cgtgcagaac aagtacctcg gcgtgatcat ccagtgcctc gtgaccgaga    1620
ccaagacctc cgtgtccagg cacatctact tcttctccgc tcgcggcagg atcgaccccc    1680
tcgtgtacct cgacgagttc ctcaggaact cagagcccgt gctcaagagg gtgaacagga    1740
ccggcaactc ctcctccaac aagcaggagt accagctcct caaggacaac ctcgtgaggt    1800
cctacaacaa ggccctcaag aagaacgccc cctactccat cttcgccatc aagaacggcc    1860
ccaagtccca catcggtagg cacctcatga cctccttcct ctcaatgaag ggcctcaccg    1920
agctcaccaa cgtggtgggc aactggtccg caagagggc ctccgccgtg ccaggaccca    1980
cctacaccca ccagatcacc gccatccccg accactactt cgccctcgtg tcaaggtact    2040
acgcctacga ccccatctcc aaggagatga tcgccctcaa ggacgagact aaccccatcg    2100
aggagtggca gcacatcgag cagctcaagg gctccgccga gggctccatc aggtaccccg    2160
cctggaacgg catcatctcc caggaggtgc tcgactacct ctcctcctac atcaacagga    2220
ggatctgagt ctagagtcct gctttaatga gatatgcgag acgcctatga tcgcatgata    2280
tttgctttca attctgttgt gcacgttgta aaaacctga gcatgtgtag ctcagatcct    2340
taccgccggt ttcggttcat tctaatgaat atatcacccg ttactatcgt attttttatga   2400 ataatattct ccgttcaatt tactgattgt accctactac ttatatgtac aatattaaaa    2460
tgaaaacaat atattgtgct gaataggttt atagcgacac ctatgataga gcgccacaat    2520
aacaaacaat tgcgttttat tattacaaat ccaatttaa aaaagcggc agaaccggtc      2580 aaacctaaaa gactgattac ataaatctta ttcaaatttc aaaaggcccc aggggctagt    2640
atctacgaca caccgagcgg cgaactaata acgttcactg aagggaactc cggttccccg    2700
ccggcgcgca tgggtgagat tccttgaagt tgagtattgg ccgtccgctc taccgaaagt    2760
tacgggcacc attcaacccg gtccagcacg gcggccgggt aaccgacttg ctgccccgag    2820
aattatgcag catttttttg gtgtatgtgg gccccaaatg aagtgcaggt caaaccttga    2880
cagtgacgac aaatcgttgg gcgggtccag ggcgaatttt gcgacaacat gtcgaggctc    2940
agcaggacct gcaggcatgc aagcttatcg ataccgtcga cctcgagggg gggcccggta    3000
cc                                                                   3002
```

<210> SEQ ID NO 58
<211> LENGTH: 12
<212> TYPE: PRT
<213> ORGANISM: Artificial Sequence
<220> FEATURE:
<223> OTHER INFORMATION: 12 N-terminal amino acid extension to GUS ORF

<400> SEQUENCE: 58

Ile Thr Ser Tyr Ser Ile His Tyr Thr Lys Leu Leu
1               5                   10

<210> SEQ ID NO 59
<211> LENGTH: 13
<212> TYPE: PRT
<213> ORGANISM: Artificial Sequence
<220> FEATURE:
<223> OTHER INFORMATION: 13 N-terminal amino acid extension to GUS ORF

<400> SEQUENCE: 59

Met Ile Thr Ser Tyr Ser Ile His Tyr Thr Lys Leu Leu
1               5                   10